United States Patent
Stokes et al.

(10) Patent No.: US 11,708,530 B2
(45) Date of Patent: Jul. 25, 2023

(54) ORGANIC LIGANDS FOR TEMPLATABLE MESOSCALE NANOCAPSULES

(71) Applicant: The Regents Of The University Of California, Oakland, CA (US)

(72) Inventors: Benjamin J. Stokes, Merced, CA (US); Amir Keshavarz, Merced, CA (US)

(73) Assignee: The Regents of the University of California, Oakland, CA (US)

( * ) Notice: Subject to any disclaimer, the term of this patent is extended or adjusted under 35 U.S.C. 154(b) by 195 days.

(21) Appl. No.: 16/758,685

(22) PCT Filed: Oct. 30, 2018

(86) PCT No.: PCT/US2018/058271
§ 371 (c)(1),
(2) Date: Apr. 23, 2020

(87) PCT Pub. No.: WO2019/089638
PCT Pub. Date: May 9, 2019

(65) Prior Publication Data
US 2021/0179939 A1    Jun. 17, 2021

Related U.S. Application Data

(60) Provisional application No. 62/579,720, filed on Oct. 31, 2017.

(51) Int. Cl.
| | |
|---|---|
| C09K 19/12 | (2006.01) |
| C07C 213/08 | (2006.01) |
| C09K 11/56 | (2006.01) |
| C09K 11/88 | (2006.01) |
| C09K 19/20 | (2006.01) |
| B82Y 20/00 | (2011.01) |
| B82Y 30/00 | (2011.01) |
| B82Y 40/00 | (2011.01) |
| C07C 217/20 | (2006.01) |

(52) U.S. Cl.
CPC ............ *C09K 19/12* (2013.01); *C07C 213/08* (2013.01); *C09K 11/565* (2013.01); *C09K 11/883* (2013.01); *C09K 19/20* (2013.01); *B82Y 20/00* (2013.01); *B82Y 30/00* (2013.01); *B82Y 40/00* (2013.01); *C07C 217/20* (2013.01); *C09K 2019/123* (2013.01); *C09K 2219/15* (2013.01)

(58) Field of Classification Search
CPC .. C09K 19/12; C09K 19/20; C09K 2019/123; C09K 2219/15; C09K 11/565; C09K 11/883; C07C 213/08; C07C 217/20; B82Y 20/00; B82Y 30/00; B82Y 40/00
See application file for complete search history.

(56) References Cited

U.S. PATENT DOCUMENTS

| | | |
|---|---|---|
| 4,792,570 A | 12/1988 | Nelson et al. |
| 7,531,106 B2 | 5/2009 | Kirsch et al. |
| 10,774,262 B2 * | 9/2020 | Hirst ............... C07C 217/22 |
| 2013/0182202 A1 | 7/2013 | Graziano et al. |
| 2020/0239781 A1 * | 7/2020 | Hirst ............... C09K 19/12 |

FOREIGN PATENT DOCUMENTS

| | | |
|---|---|---|
| EP | 0157652 | 10/1985 |

OTHER PUBLICATIONS

Keshavarz et al., "New Promesogenic Ligands for Host Medium Microencapsulation by Quantum Dots via Liquid Crystal Phase Transition Templating", ACS Appl. Nano Mater, vol. 2., pp. 2542-2547. (Year: 2019).*
Keshavarz et al., "New Modular Calamitic Ligands for Self-Assembly of Thermostable Quantum Dot Microcapsules via Nematic Templating", ChemRxiv (2018), 1-5 (Year: 2018).*
National Center for Biotechnology Information. PubChem Database 2005 "2-(2-Phenylphenoxy)ethanamine" Pubchem-CID: 542001 Create Date: Mar, 27, pp. 1-15.

* cited by examiner

*Primary Examiner* — Geraldina Visconti
(74) *Attorney, Agent, or Firm* — Rudy J. Ng; Michael J. Blessent; Bozicevic, Field & Francis LLP

(57) ABSTRACT

Organic ligands and methods for preparing a variety of organic ligands are provided. The subject methods provide for the preparation of organic ligands in high yield and purity for use as ligands for attachment to nanoparticles to enable the formation of three dimensional nanocapsules of stably associated organic ligand-functionalized nanoparticles. Compositions that include these nanocapsules, as well as methods of making the nanocapsules are also provided.

15 Claims, 5 Drawing Sheets

ORGANIC LIGANDS FOR TEMPLATABLE MESOSCALE NANOCAPSULES

CROSS-REFERENCE

This application claims the benefit of U.S. Provisional Patent Application No. 62/579,720, filed Oct. 31, 2017, which application is incorporated herein by reference in its entirety.

STATEMENT REGARDING FEDERALLY SPONSORED RESEARCH

This invention was made with government support under Grant Number 1507551 awarded by the National Science Foundation, Chemical, Bioengineering, Environmental, and Transport Systems (CBET). The government has certain rights in the invention.

INTRODUCTION

The unique electronic, magnetic, and optical properties of nanoparticles (NPs) distinguish them from bulk materials. By combining these properties with the huge diversity of available compositions and morphologies, many new NP applications have been developed in optoelectronics, photovoltaics, nanomedicines, and cosmetics, to name but a few. One of the most exciting frontiers in nanoscience is the use of nanoscale building blocks to generate new meta-materials, wherein novel properties emerge as nanoparticle-based materials are assembled from the ground up. Recent developments include materials for electromagnetic cloaking, optical band gap structures, and localized plasmon resonance.

Liquid crystal (LC) phase transition dynamics can be used as a powerful tool to control the assembly of dispersed nanoparticles. Tailored organic ligands can both enhance and tune particle dispersion in the liquid crystal phase to create novel liquid crystal nanocomposites, such as nanocapsules. Soft nanocomposites have recently risen to prominence for their potential usage in a variety of industrial applications such as photovoltaics, photonic materials, and the liquid crystal laser. Further development of stable organic ligands for use in functionalizing nanoparticles to form new micron-scale structures, such as nanocapsule materials, is of interest.

SUMMARY

Organic ligands and methods for preparing a variety of organic ligands are provided. The subject methods provide for the preparation of organic ligands in high yield and purity for use as ligands for attachment to nanoparticles to enable the formation of three dimensional nanocapsules of stably associated organic ligand-functionalized nanoparticles. Compositions that include these nanocapsules, as well as methods of making the nanocapsules are also provided. The nanocapsules, compositions and methods find use in a variety of applications, such as light emitting devices (e.g., video displays, lights, etc.), inks, photonics and encapsulation technologies.

Aspects of the present disclosure include an organic ligand of formula (I):

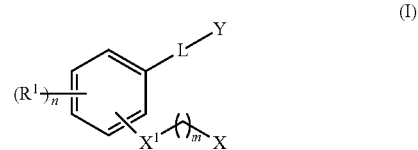

wherein:
L is selected from phenyl, substituted phenyl, biphenyl and substituted biphenyl;
Y is selected from H, halogen, hydroxyl, azido, phenyl, substituted phenyl, biphenyl, substituted biphenyl, alkoxy, substituted alkoxy, alkyl, substituted alkyl, amino, substituted amino, cycloalkyl, substituted cycloalkyl, heterocycloalkyl, and substituted heterocycloalkyl;
$R^1$ are each independently selected from H, halogen, hydroxyl, azido, alkyl, substituted alkyl, alkenyl, substituted alkenyl, alkynyl, substituted alkynyl, alkoxy, substituted alkoxy, amino, and substituted amino;
X is an amine or a thiol group;
$X^1$ is selected from O, NR', CR'$_2$ and S, wherein each R' is independently selected from H, alkyl, substituted alkyl, alkenyl, substituted alkenyl, aryl, substituted aryl;
n is an integer from 1 to 4; and
m is an integer from 1 to 14.

In some embodiments of the organic ligand of formula (I), L is:

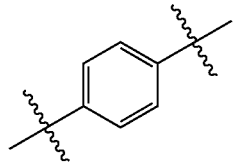 [SMILES: *c1ccc(*)cc1]

In other embodiments of the organic ligand of formula (I), Y is selected from:

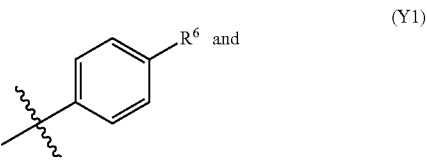

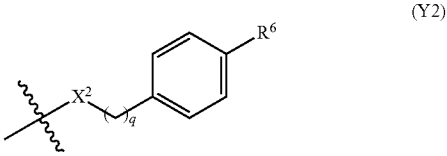

wherein, $R^6$ is selected from H, halogen, hydroxyl, azido, alkyl, substituted alkyl, alkenyl, substituted alkenyl, alkynyl, substituted alkynyl, alkoxy, substituted alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol;

$X^2$ is selected from O, NR', CR'$_2$ and S, wherein each R' is independently selected from H, alkyl, substituted alkyl, alkenyl, substituted alkenyl, aryl, substituted aryl; and q is an integer from 1 to 14.

In embodiments of the organic ligand of formula (I), $R^1$ and $R^6$ are $C_1$-$C_{12}$ alkoxy and n is 1.

Embodiments of the present disclosure include an organic ligand of formula (II):

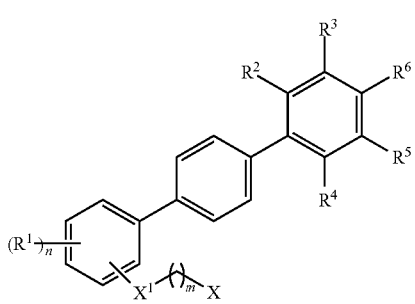

(II)

wherein:

$R^1$ are each independently selected from H, halogen, hydroxyl, azido, alkyl, substituted alkyl, alkenyl, substituted alkenyl, alkynyl, substituted alkynyl, alkoxy, substituted alkoxy, amino, and substituted amino;

$R^2$, $R^3$, $R^4$, $R^5$, and $R^6$ are each independently selected from H, halogen, hydroxyl, azido, alkyl, substituted alkyl, alkenyl, substituted alkenyl, alkynyl, substituted alkynyl, alkoxy, substituted alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol;

X is an amine or a thiol group;

$X^1$ is selected from O, NR', CR'$_2$ and S, wherein each R' is independently selected from H, alkyl, substituted alkyl, alkenyl, substituted alkenyl, aryl, substituted aryl;

n is an integer from 1 to 4; and m is an integer from 1 to 14.

In certain embodiments, the organic ligand of formula (II) has a structure according to formula (III):

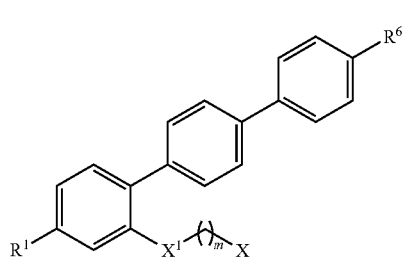

(III)

wherein:

$R^1$ is selected from halogen, hydroxyl, azido, alkyl, substituted alkyl, alkenyl, substituted alkenyl, alkynyl, substituted alkynyl, alkoxy, substituted alkoxy, amino, and substituted amino;

$R^6$ is selected from H, halogen, hydroxyl, azido, alkyl, substituted alkyl, alkenyl, substituted alkenyl, alkynyl, substituted alkynyl, alkoxy, substituted alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol;

X is an amine or a thiol group;

$X^1$ is selected from O, NR', CR'$_2$ and S, wherein each R' is independently selected from H, alkyl, substituted alkyl, alkenyl, substituted alkenyl, aryl, substituted aryl; and m is an integer from 1 to 14.

Embodiments of the present disclosure include an organic ligand of formula (IV):

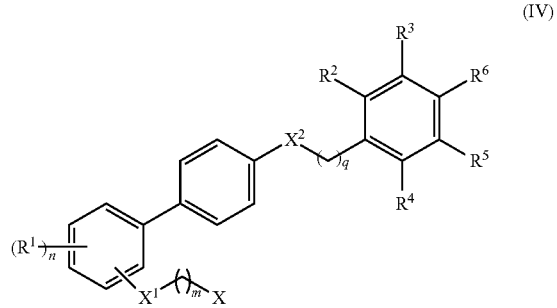

(IV)

wherein:

$R^1$ are each independently selected from H, halogen, hydroxyl, azido, alkyl, substituted alkyl, alkenyl, substituted alkenyl, alkynyl, substituted alkynyl, alkoxy, amino, and substituted amino;

$R^2$, $R^3$, $R^4$, $R^5$, and $R^6$ are each independently selected from H, halogen, hydroxyl, azido, alkyl, substituted alkyl, alkenyl, substituted alkenyl, alkynyl, substituted alkynyl, alkoxy, substituted alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol;

X is an amine or a thiol group;

$X^1$ is selected from O, NR', CR'$_2$ and S, wherein each R' is independently selected from H, alkyl, substituted alkyl, alkenyl, substituted alkenyl, aryl, substituted aryl;

$X^2$ is selected from O, NR', CR'$_2$ and S, wherein each R' is independently selected from H, alkyl, substituted alkyl, alkenyl, substituted alkenyl, aryl, substituted aryl;

n is an integer from 1 to 4; and m and q are each independently an integer from 1 to 14.

In certain embodiments, the organic ligand of formula (IV) has a structure according to formula (V):

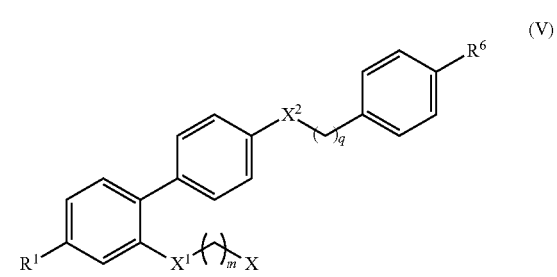

(V)

wherein:

R¹ is selected from halogen, hydroxyl, azido, alkyl, substituted alkyl, alkenyl, substituted alkenyl, alkynyl, substituted alkynyl, alkoxy, substituted alkoxy, amino, and substituted amino;

R⁶ is selected from H, halogen, hydroxyl, azido, alkyl, substituted alkyl, alkenyl, substituted alkenyl, alkynyl, substituted alkynyl, alkoxy, substituted alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol;

X is an amine or a thiol group;

$X^1$ is selected from O, NR', CR'$_2$ and S, wherein each R' is independently selected from H, alkyl, substituted alkyl, alkenyl, substituted alkenyl, aryl, substituted aryl;

$X^2$ is selected from O, NR', CR'$_2$ and S, wherein each R' is independently selected from H, alkyl, substituted alkyl, alkenyl, substituted alkenyl, aryl, substituted aryl; and m and q are each independently an integer from 1 to 14.

In some embodiments of the subject organic ligand, R¹ is $C_1$-$C_{12}$ alkoxy. In some embodiments of the subject organic ligands, R⁶ is $C_1$-$C_{12}$ alkoxy.

In some embodiments of the subject organic ligand, X is an amine group. In other embodiments of the subject organic ligand, X is a thiol group.

In certain embodiments, the subject organic ligand is selected from the group:

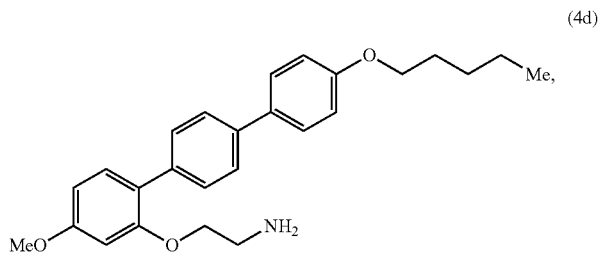

(4d)

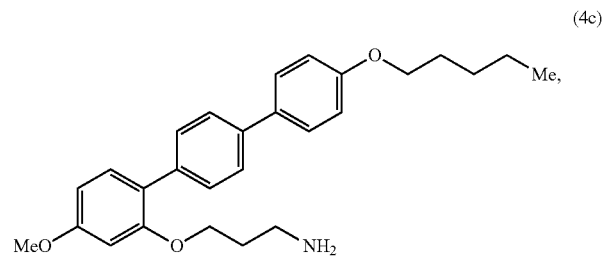

(4c)

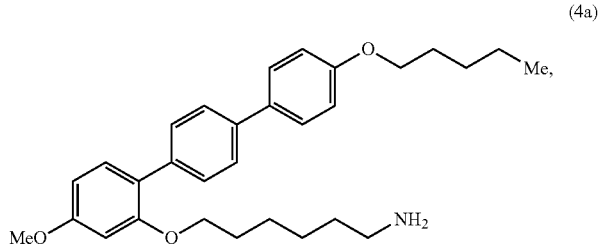

(4a)

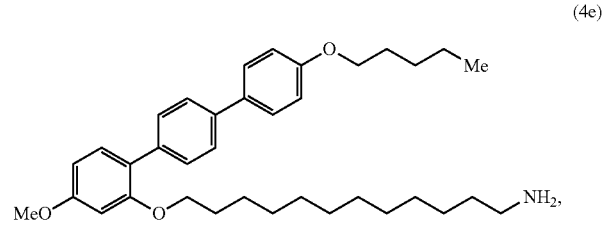

(4e)

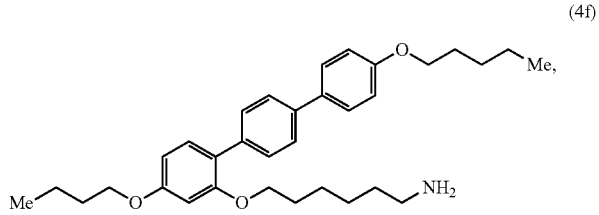

(4f)

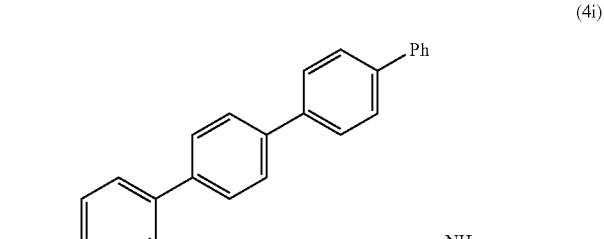

(4i)

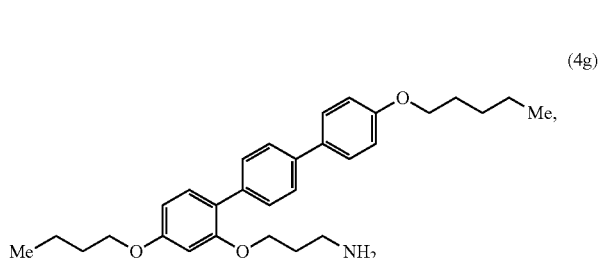

(4g)

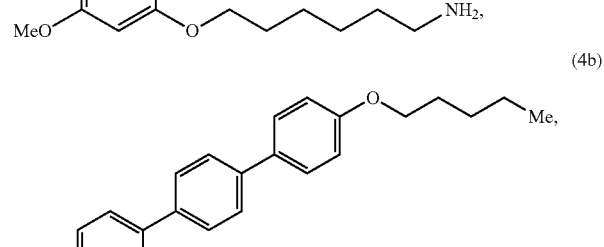

(4b)

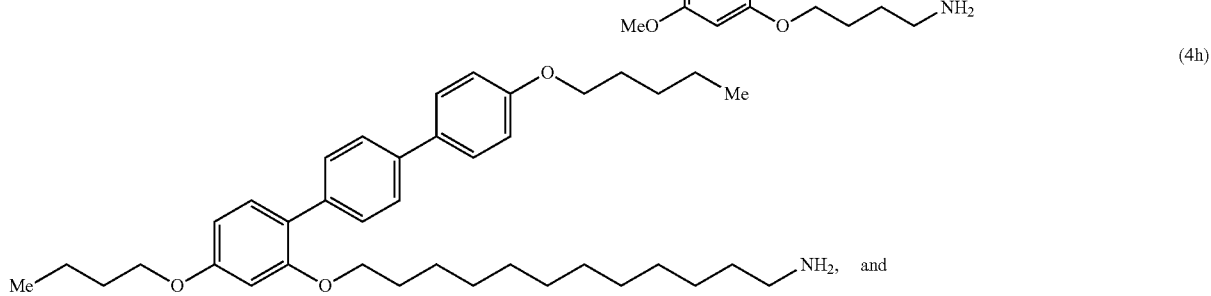

(4h)

-continued

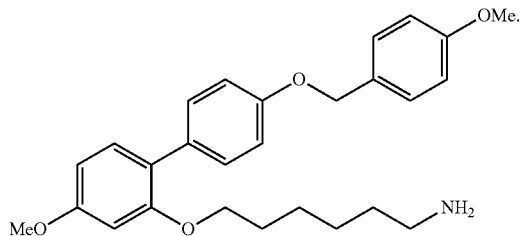

(4j)

In some embodiments, the subject organic ligand is the following structure:

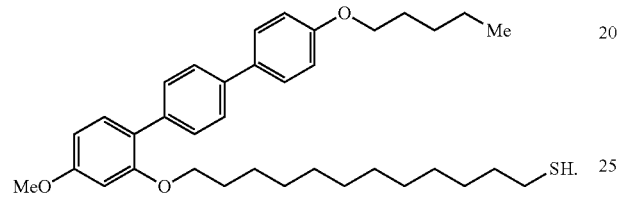

(5)

Aspects of the present disclosure include a method of preparing a subject organic ligand, the method comprising:
preparing a compound of formula (VII) from a compound of formula (VI):

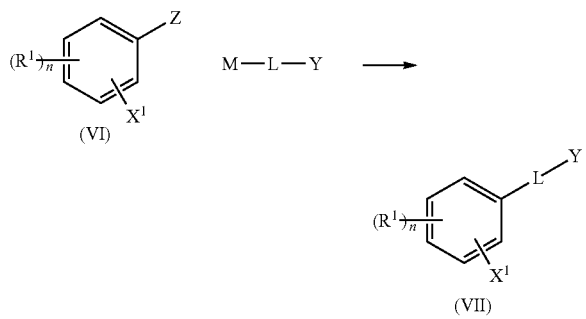

wherein:
Z is a leaving group,
M is selected from a substituted metalloid or a substituted metal;
L is selected from phenyl, substituted phenyl, biphenyl and substituted biphenyl;
Y is selected from H, halogen, hydroxyl, azido, phenyl, substituted phenyl, biphenyl, substituted biphenyl, alkoxy, substituted alkoxy, alkyl, substituted alkyl, amino, substituted amino, cycloalkyl, substituted cycloalkyl, heterocycloalkyl, and substituted heterocycloalkyl;
$R^1$ are each independently selected from H, halogen, hydroxyl, azido, alkyl, substituted alkyl, alkenyl, substituted alkenyl, alkynyl, substituted alkynyl, alkoxy, substituted alkoxy, amino, and substituted amino;
$X^1$ is selected from O, NR', $CR'_2$ and S, wherein each R' is independently selected from H, alkyl, substituted alkyl, alkenyl, substituted alkenyl, aryl, substituted aryl; and
n is an integer from 1 to 4.
In certain embodiments, the compound of formula (VII) is prepared via a Suzuki coupling between a compound of formula (VI) and a derivative of formula (VIII):

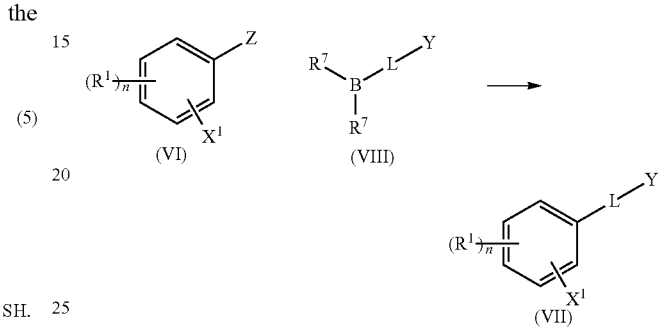

wherein:
Z is a leaving group;
L is selected from phenyl, substituted phenyl, biphenyl and substituted biphenyl;
Y is selected from H, halogen, hydroxyl, azido, phenyl, substituted phenyl, biphenyl, substituted biphenyl, alkoxy, substituted alkoxy, alkyl, substituted alkyl, amino, substituted amino, cycloalkyl, substituted cycloalkyl, heterocycloalkyl, and substituted heterocycloalkyl;
$R^1$ are each independently selected from H, halogen, hydroxyl, azido, alkyl, substituted alkyl, alkenyl, substituted alkenyl, alkynyl, substituted alkynyl, alkoxy, substituted alkoxy, amino, and substituted amino;
$R^7$ are each independently selected from hydroxyl, alkyl, substituted alkyl, heteroalkyl and substituted heteroalkyl;
or both $R^7$ groups together with the boron to which they are attached form a group selected from heterocycle, substituted heterocycle, cycloalkyl, substituted cycloalkyl;
$X^1$ is selected from O, NR', $CR'_2$ and S, wherein each R' is independently selected from H, alkyl, substituted alkyl, alkenyl, substituted alkenyl, aryl, substituted aryl; and
n is an integer from 1 to 4.
Embodiments of the method of preparing a subject organic ligand further include preparing an organic ligand of formula (IX) from the compound of formula (VII):

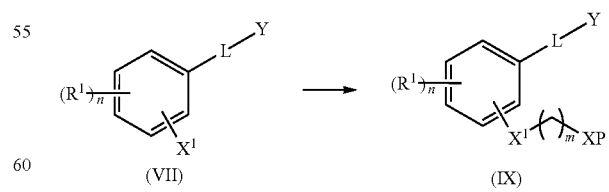

wherein:
L is selected from phenyl, substituted phenyl, biphenyl and substituted biphenyl;
Y is selected from H, halogen, hydroxyl, azido, phenyl, substituted phenyl, biphenyl, substituted biphenyl, alkoxy, substituted alkoxy, alkyl, substituted alkyl, amino, substituted amino, cycloalkyl, substituted cycloalkyl, heterocycloalkyl, and substituted heterocycloalkyl;

R$^1$ are each independently selected from H, halogen, hydroxyl, azido, alkyl, substituted alkyl, alkenyl, substituted alkenyl, alkynyl, substituted alkynyl, alkoxy, substituted alkoxy, amino, and substituted amino;

X is an amine or a thiol group;

P is a protecting group;

X$^1$ is selected from O, NR', CR'$_2$ and S, wherein each R' is independently selected from H, alkyl, substituted alkyl, alkenyl, substituted alkenyl, aryl, substituted aryl;

n is an integer from 1 to 4; and m is an integer from 1 to 14.

In some embodiments of the method of preparing a subject organic ligand, the method further includes preparing an organic ligand of formula (I) from the compound of formula (IX):

wherein:

L is selected from phenyl, substituted phenyl, biphenyl and substituted biphenyl;

Y is selected from H, halogen, hydroxyl, azido, phenyl, substituted phenyl, biphenyl, substituted biphenyl, alkoxy, substituted alkoxy, alkyl, substituted alkyl, amino, substituted amino, cycloalkyl, substituted cycloalkyl, heterocycloalkyl, and substituted heterocycloalkyl;

R$^1$ are each independently selected from H, halogen, hydroxyl, azido, alkyl, substituted alkyl, alkenyl, substituted alkenyl, alkynyl, substituted alkynyl, alkoxy, substituted alkoxy, amino, and substituted amino;

X is an amine or a thiol group;

P is a protecting group;

X$^1$ is selected from O, NR', CR'$_2$ and S, wherein each R' is independently selected from H, alkyl, substituted alkyl, alkenyl, substituted alkenyl, aryl, substituted aryl;

n is an integer from 1 to 4; and m is an integer from 1 to 14.

In certain embodiments of the method of preparing a subject organic ligand, the coupling between a compound of formula (VI) and a compound of formula (VIII) is catalyzed by a palladium catalyst. In certain embodiments, in the compound of formula (VIII), both R$^7$ groups are hydroxyl. In some embodiments, in the compound of formula (VI), the leaving group, Z, is a halogen. In certain other embodiments, the leaving group, Z, is a tosylate.

Aspects of the present disclosure include a nanocapsule comprising organic ligand-functionalized nanoparticles, wherein the organic ligand has a structure as disclosed herein.

In some embodiments, the subject nanocapsule structure has a dimension of 0.01 µm to 10 µm. In embodiments, the nanocapsule has a spherical surface. In certain cases, the spherical surface has an average diameter of 0.01 µm to 10 µm.

In some embodiments of the nanocapsules, the nanoparticles have an average diameter of 1 nm to 100 nm. In certain embodiments, the nanoparticles are composed of a material selected from a semiconductor material, a metal, a metal oxide, a metalloid, a metal coated material, an oxide, a magnetic material, a nanosome, a dielectric material and a polymer, or combinations thereof. In some cases, the nanoparticles are composed of cadmium selenide (CdSe), zinc sulfide (ZnS), gold, or combinations thereof.

In some embodiments of the nanocapsule, the structure is composed of nanoparticles having substantially the same physical and chemical characteristics. In other embodiments, the structure is composed of nanoparticles having different physical and/or chemical characteristics.

Aspects of the present disclosure include a composition that includes a liquid; and a nanocapsule as disclosed herein in the liquid. In certain embodiments, the liquid is an organic solvent.

Aspects of the present disclosure include a composition for producing a nanocapsule, including organic ligand-functionalized nanoparticles, wherein the organic ligand has a structure as disclosed herein; and a liquid crystalline liquid.

In some embodiments of the composition for producing a nanocapsule, an organic ligand of the organic ligand-functionalized nanoparticles has a phase transition temperature greater than the phase transition temperature of the liquid crystalline liquid.

Aspects of the present disclosure include a method of producing a nanocapsule. The method includes dispersing organic ligand-functionalized nanoparticles in a liquid crystalline liquid, wherein the organic ligand has a structure as disclosed herein; and inducing a phase transition from an isotopic phase to a nematic phase in the liquid crystalline liquid to produce a nanocapsule of stably associated organic ligand-functionalized nanoparticles.

In some embodiments, the dispersing comprises applying sound energy to the organic ligand-functionalized nanoparticles in the liquid crystalline liquid.

In some embodiments, the inducing includes reducing the temperature of the liquid crystalline liquid.

In some embodiments, the method of producing a nanocapsule further includes crosslinking the organic ligand-functionalized nanoparticles in the nanocapsule. In certain embodiments, the organic ligand-functionalized nanoparticles comprise a light activated cross-linkable functional group, and the crosslinking comprises applying light to the nanoparticles sufficient to activate the light activated cross-linkable functional group and produce one or more crosslinks between the nanoparticles.

Aspects of the present disclosure include a material comprising a nanocapsule of stably associated organic ligand-functionalized nanoparticles produced by the methods disclosed herein.

BRIEF DESCRIPTION OF THE DRAWINGS

The ordinarily skilled artisan will understand that the drawings, described below, are for illustration purposes only. The drawings are not intended to limit the scope of the present teachings in any way.

TERMS

Figure 1:
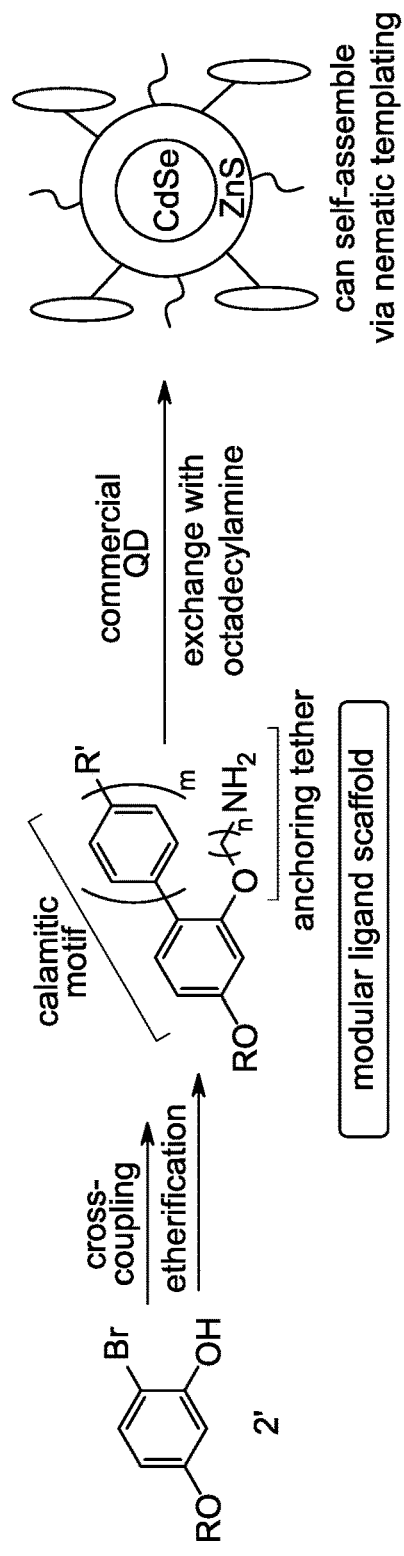
FIG. 1, shows a general outline of the strategy for synthesis of exemplary subject organic ligands and ligand exchange with octadecylamine ligands of commercial quantum dots to afford ligand-modified metal nanoparticle self-assembly.
Figure 2:
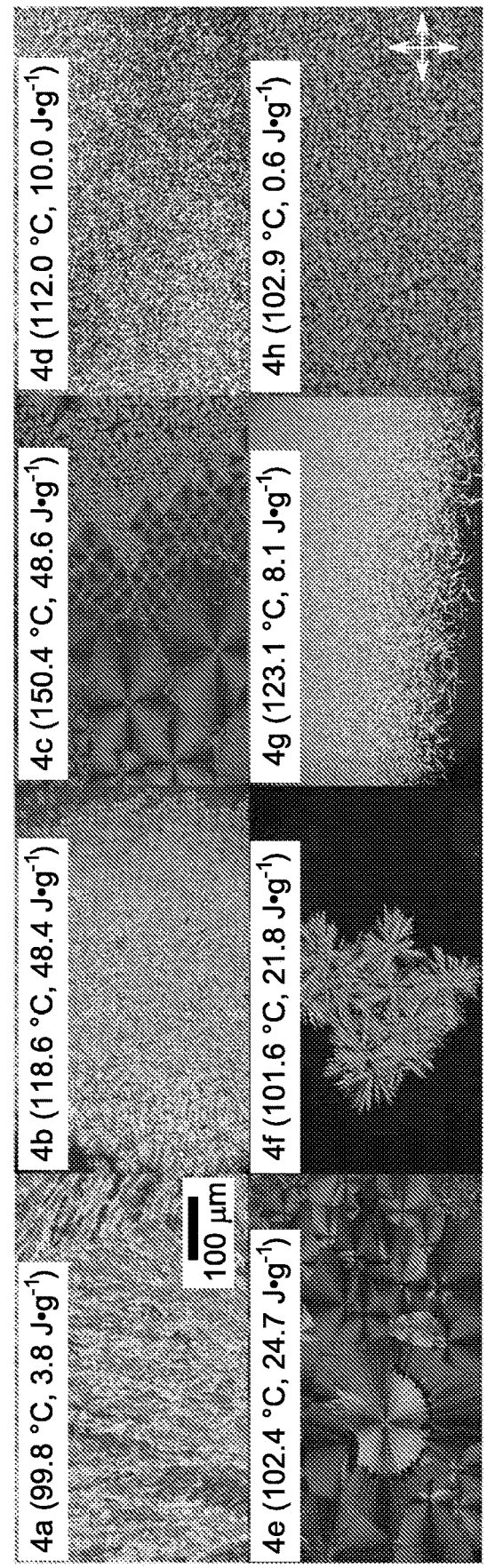
FIG. 2, shows birefringence textures of exemplary subject organic ligands observed using polarized optical microscopy (10× objective). Transition temperature (T$_{trans}$) and latent heat ($\Delta H_{trans}$) of the only observed differential scanning calorimetry event (e.g., see FIG. 3) for each ligand are included in parentheses. Cross arrows indicate polarizer direction.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

The term "substituted alkyl" refers to an alkyl group as defined herein wherein one or more carbon atoms in the alkyl chain (except for the $C_1$ carbon) have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C (O)—, —C(O)NR$^{10}$— and the like. This term includes, by way of example, methylene (—$CH_2$—), ethylene (—$CH_2CH_2$—), n-propylene (—$CH_2CH_2CH_2$—), iso-propylene (—$CH_2CH(CH_3)$—), (—$C(CH_3)_2CH_2CH_2$—), (—$C(CH_3)_2CH_2C(O)$—), (—$C(CH_3)_2CH_2C(O)NH$—), (—$CH(CH_3)CH_2$—), and the like.

"Substituted alkylene" refers to an alkylene group having from 1 to 3 hydrogens replaced with substituents as described for carbons in the definition of "substituted" below.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$— heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—$CH_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$— alkyl, —SO$_2$-substituted alkyl, —SO$_2$-aryl, and —SO$_2$-heteroaryl.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$— heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO— substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO₂-alkyl, —SO₂-substituted alkyl, —SO₂-aryl and —SO₂— heteroaryl, and trihalomethyl.

"Thiol" refers to the group —SH.

"Alkylthio" or the term "thioalkoxy" refers to the group —S-alkyl, or —S-alkoxy, such as SH-(alkyl)-O—. wherein alkyl and alkoxy are as defined herein.

"Leaving group" refers to an activated substituent which is characterized by being a good leaving group. Examples of leaving groups include, but are not limited to a halide (e.g. chloride, bromide or iodide), or a sulfonate, such as a sulfonate esters (e.g. triflate, mesylate, nonaflate or tosylate).

"Protecting group" refers to the temporary modifications of a potentially reactive functional group which protect it from undesired chemical transformations. Examples of such protecting groups include esters of carboxylic acids, carbamates of amines, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, 2nd ed.; Wiley: New York, 1991).

The term "salt thereof" means a compound formed when a proton of an acid is replaced by a cation, such as a metal cation or an organic cation and the like. Where applicable, the salt is a pharmaceutically acceptable salt. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

As used herein, an organic ligand that is of "high purity" or is "substantially pure" refers to an organic ligand that is substantially free of one or more other compounds, i.e., the organic ligand contains greater than 80%, 90%, 95%, 96%, 97%, 98%, 99%, 99.5%, 99.6%, 99.7%, 99.8%, 99.9% by weight of the organic ligand.

Unless indicated otherwise, the nomenclature of substituents that are not explicitly defined herein are arrived at by naming the terminal portion of the functionality followed by the adjacent functionality toward the point of attachment. For example, the substituent "aminoalkoxy" refers to the group NH₂-(alkyl)-O—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

DETAILED DESCRIPTION

Organic ligands and methods for preparing a variety of organic ligands are provided. The subject methods provide for the preparation of organic ligands in high yield and purity for use as ligands for attachment to nanoparticles to enable the formation of three dimensional nanocapsules of stably associated organic ligand-functionalized nanoparticles. Compositions that include these nanocapsules, as well as methods of making the nanocapsules are also provided. The nanocapsules, compositions and methods find use in a variety of applications, such as light emitting devices (e.g., video displays, lights, etc.), dyes, photonics and encapsulation technologies.

Organic Ligands

As summarized above, aspects of the present disclosure include organic ligands of formula (I)-(IV). In some cases, the organic ligands include a biphenyl, a p-terphenyl, or a quaterphenyl core with a variety of substituents, including a flexible amine or thiol containing tether. In some cases, the organic ligands include a flexible amine containing tether. In other cases, the organic ligands include a flexible thiol containing tether.

In some cases, the subject organic ligand is of formula (I):

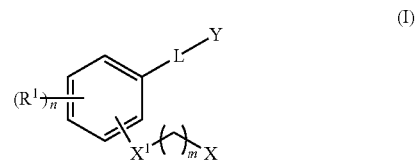

wherein:

L is selected from phenyl, substituted phenyl, biphenyl and substituted biphenyl;

Y is selected from H, halogen, hydroxyl, azido, phenyl, substituted phenyl, biphenyl, substituted biphenyl, alkoxy, substituted alkoxy, alkyl, substituted alkyl, amino, substituted amino, cycloalkyl, substituted cycloalkyl, heterocycloalkyl, and substituted heterocycloalkyl;

R¹ are each independently selected from H, halogen, hydroxyl, azido, alkyl, substituted alkyl, alkenyl, substituted alkenyl, alkynyl, substituted alkynyl, alkoxy, substituted alkoxy, amino, and substituted amino;

X is an amine or a thiol group;

X¹ is selected from O, NR', CR'₂ and S, wherein each R' is independently selected from H, alkyl, substituted alkyl, alkenyl, substituted alkenyl, aryl, substituted aryl;

n is an integer from 1 to 4; and m is an integer from 1 to 14.

In some cases, the subject organic ligand is of formula (Ia):

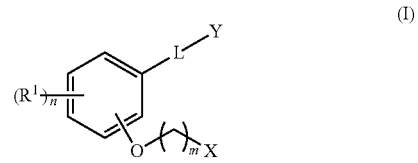

wherein:

L is selected from phenyl, substituted phenyl, biphenyl and substituted biphenyl;

Y is selected from H, halogen, hydroxyl, azido, phenyl, substituted phenyl, biphenyl, substituted biphenyl, alkoxy, substituted alkoxy, alkyl, substituted alkyl, amino, substituted amino, cycloalkyl, substituted cycloalkyl, heterocycloalkyl, and substituted heterocycloalkyl;

R¹ are each independently selected from H, halogen, hydroxyl, azido, alkyl, substituted alkyl, alkenyl, substituted alkenyl, alkynyl, substituted alkynyl, alkoxy, substituted alkoxy, amino, and substituted amino;

X is an amine or a thiol group;

n is an integer from 1 to 4; and m is an integer from 1 to 14.

In some embodiments of formula (I), the organic ligand L is a phenyl group represented as follows:

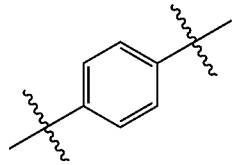 [SMILES: *c1ccc(*)cc1]

In other embodiments of formula (I), L is a substituted phenyl group, wherein any or all of the H groups in the phenyl group can be replaced with a group including but not limited to, halogen, hydroxyl, azido, alkyl, substituted alkyl, alkenyl, substituted alkenyl, alkynyl, substituted alkynyl, alkoxy, substituted alkoxy, amino, and substituted amino.

In some embodiments of formula (I), Y is selected from the following aryl groups:

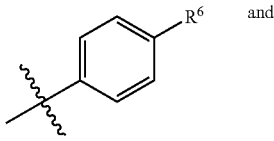
(Y1) and

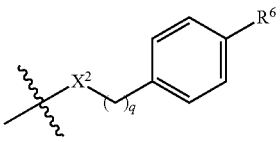
(Y2)

wherein, $R^6$ is selected from H, halogen, hydroxyl, azido, alkyl, substituted alkyl, alkenyl, substituted alkenyl, alkynyl, substituted alkynyl, alkoxy, substituted alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol; and $X^2$ is selected from O, NR', CR'$_2$ and S, wherein each R' is independently selected from H, alkyl, substituted alkyl, alkenyl, substituted alkenyl, aryl, substituted aryl. In some cases, the aryl group Y1 or Y2 is further substituted, wherein any or all of the H groups in the aryl groups can be replaced with a group including but not limited to, halogen, hydroxyl, azido, alkyl, substituted alkyl, alkenyl, substituted alkenyl, alkynyl, substituted alkynyl, alkoxy, substituted alkoxy, amino, and substituted amino. In some cases, q is an integer from 1 to 14, such as 1 to 12, such as 1 to 10, such as 1 to 8, such as 1 to 6, such as 1 to 4, such as 1 to 2. In some cases, q is less than 6, such as 5, 4, 3, 2, or 1. In certain embodiments, q is 1.

In some embodiments of formula (I) or (Ia), Y is the following aryl groups:

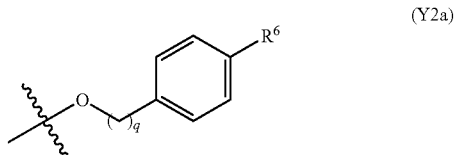
(Y2a)

wherein, $R^6$ is selected from H, halogen, hydroxyl, azido, alkyl, substituted alkyl, alkenyl, substituted alkenyl, alkynyl, substituted alkynyl, alkoxy, substituted alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol. In some cases, q is an integer from 1 to 14, such as 1 to 12, such as 1 to 10, such as 1 to 8, such as 1 to 6, such as 1 to 4, such as 1 to 2. In some cases, q is less than 6, such as 5, 4, 3, 2, or 1. In certain embodiments, q is 1.

In some instances of formula (I) or (Ia), $R^1$ and $R^6$ are each independently selected from H, halo, azido, alkyl, substituted alkyl, alkoxy, and substituted alkoxy.

In some instances of formula (I) or (Ia), $R^1$ is alkoxy, such as a $C_{1-14}$ alkoxy, $C_{1-12}$ alkoxy, $C_{1-10}$ alkoxy, $C_{1-8}$ alkoxy, $C_{1-6}$ alkoxy, or $C_{1-3}$ alkoxy. In some instances, $R^1$ is $C_5$ alkoxy, such as pentyloxy. In some instances, $R^1$ is $C_4$ alkoxy, such as butyloxy. In some instances, $R^1$ is $C_1$ alkoxy, such as methoxy. In some instances, $R^1$ is substituted alkoxy, such as a substituted $C_{1-14}$ alkoxy, substituted $C_{1-12}$ alkoxy, substituted $C_{1-10}$ alkoxy, substituted $C_{1-8}$ alkoxy, or substituted $C_{1-6}$ alkoxy. In some instances, $R^1$ is substituted $C_6$ alkoxy, such as substituted hexyloxy. In some instances, $R^1$ is substituted $C_{12}$ alkoxy, such as substituted dodecyloxy. In some instances, the substituent on the substituted alkoxy is phosphate or substituted phosphate.

In some instances of formula (I) or (Ia), Y is selected from Y1 or Y2, and $R^6$ is alkoxy, such as a $C_{1-14}$ alkoxy, $C_{1-12}$ alkoxy, $C_{1-10}$ alkoxy, $C_{1-8}$ alkoxy, $C_{1-6}$ alkoxy, or $C_{1-3}$ alkoxy. In some instances, $R^6$ is $C_5$ alkoxy, such as pentyloxy. In some instances, $R^6$ is $C_4$ alkoxy, such as butyloxy. In some instances, $R^6$ is $C_1$ alkoxy, such as methoxy. In some instances, $R^6$ is substituted alkoxy, such as a substituted $C_{1-14}$ alkoxy, substituted $C_{1-12}$ alkoxy, substituted $C_{1-10}$ alkoxy, substituted $C_{1-8}$ alkoxy, or substituted $C_{1-6}$ alkoxy. In some instances, $R^6$ is substituted $C_6$ alkoxy, such as substituted hexyloxy. In some instances, $R^6$ is substituted $C_{12}$ alkoxy, such as substituted dodecyloxy. In some instances, the substituent on the substituted alkoxy is phosphate or substituted phosphate.

In some embodiments of formula (I) or (Ia), $R^1$ and $R^6$ are $C_1$-$C_{12}$ alkoxy and n is 1. In some cases, n is greater than 1, such as 2, 3 or 4.

In some instances of formula (I) or (Ia), m is 1 to 14 so as to provide a substituted $C_{1-14}$ alkoxy group, such as a substituted $C_{1-12}$ alkoxy, substituted $C_{1-10}$ alkoxy, substituted $C_{1-8}$ alkoxy, substituted $C_{1-6}$ alkoxy, or substituted $C_{1-3}$ alkoxy. In some instances, m is 2, so as to provide a substituted $C_2$ alkoxy, such as substituted ethoxy. In some instances, m is 3, so as to provide a substituted $C_3$ alkoxy, such as substituted propoxy. In some instances, m is 6 so as to provide a substituted $C_6$ alkoxy, such as substituted hexyloxy. In some instances, m is 12 so as to provide a substituted $C_{12}$ alkoxy, such as substituted dodecyloxy. In some instances, X on the substituted alkoxy is amino or substituted amino. In some instances, X on the substituted alkoxy is amino, such that the group is an aminoalkoxy, such as aminopropoxy (e.g., 3-aminopropoxy) or aminohexyloxy (e.g., 6-aminohexyloxy). In some instances, X on the substituted alkoxy is thiol or substituted thiol. In some instances, X on the substituted alkoxy is thiol, such that the group is a thioalkoxy, such as thiopropoxy (e.g., 3-thiopropoxy), thiohexyloxy (e.g., 6-thiohexyloxy) or thiododecanoxy. In some embodiments, the organic ligand is attached to a nanoparticle through the aminoalkoxy or thioalkoxy substituent. For instance, in embodiments where formula (I) includes an aminoalkoxy group, the organic ligand may be attached to the nanoparticle through the amino group of the aminoalkoxy tether. In embodiments where formula (I) includes a thioalkoxy group, the organic ligand may be attached to the nanoparticle through the thiol group of the thioalkoxy.

In some embodiments the organic ligand of formula (I), has the structure of formula (II):

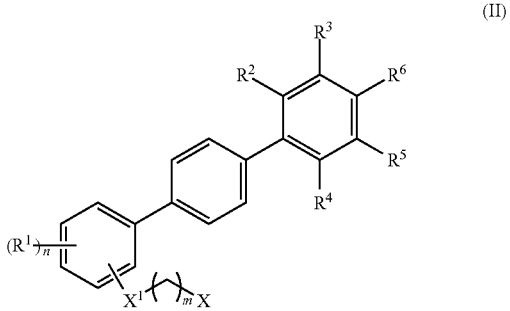

wherein:

$R^1$ are each independently selected H, halogen, hydroxyl, azido, alkyl, substituted alkyl, alkenyl, substituted alkenyl, alkynyl, substituted alkynyl, alkoxy, substituted alkoxy, amino, and substituted amino;

$R^2$, $R^3$, $R^4$, $R^5$, and $R^6$ are each independently selected from H, halogen, hydroxyl, azido, alkyl, substituted alkyl, alkenyl, substituted alkenyl, alkynyl, substituted alkynyl, alkoxy, substituted alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol;

X is an amine or a thiol group;

$X^1$ is selected from O, NR', $CR'_2$ and S, wherein each R' is independently selected from H, alkyl, substituted alkyl, alkenyl, substituted alkenyl, aryl, substituted aryl;

n is an integer from 1 to 4; and m is an integer from 1 to 14.

In some embodiments the organic ligand of formula (I), has the structure of formula (II):

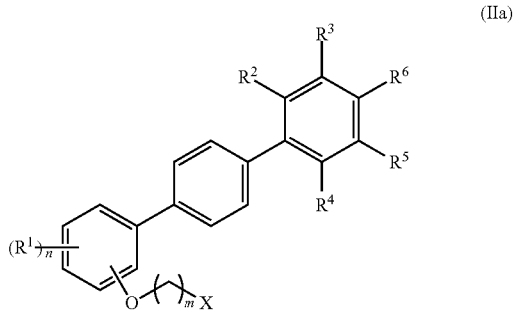

wherein:

$R^1$ are each independently selected H, halogen, hydroxyl, azido, alkyl, substituted alkyl, alkenyl, substituted alkenyl, alkynyl, substituted alkynyl, alkoxy, substituted alkoxy, amino, and substituted amino;

$R^2$, $R^3$, $R^4$, $R^5$, and $R^6$ are each independently selected from H, halogen, hydroxyl, azido, alkyl, substituted alkyl, alkenyl, substituted alkenyl, alkynyl, substituted alkynyl, alkoxy, substituted alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol;

X is an amine or a thiol group;

n is an integer from 1 to 4; and m is an integer from 1 to 14.

In some instances of formula (II) or (IIa), $R^1$ is alkoxy, such as a $C_{1-14}$ alkoxy, $C_{1-12}$ alkoxy, $C_{1-10}$ alkoxy, $C_{1-8}$ alkoxy, $C_{1-6}$ alkoxy, or $C_{1-3}$ alkoxy. In some instances, $R^1$ is $C_5$ alkoxy, such as pentyloxy. In some instances, $R^1$ is $C_4$ alkoxy, such as butyloxy. In some instances, $R^1$ is $C_1$ alkoxy, such as methoxy. In some instances, $R^1$ is substituted alkoxy, such as a substituted $C_{1-14}$ alkoxy, substituted $C_{1-12}$ alkoxy, substituted $C_{1-10}$ alkoxy, substituted $C_{1-8}$ alkoxy, or substituted $C_{1-6}$ alkoxy. In some instances, $R^1$ is substituted $C_6$ alkoxy, such as substituted hexyloxy. In some instances, $R^1$ is substituted $C_{12}$ alkoxy, such as substituted dodecyloxy. In some instances, the substituent on the substituted alkoxy is phosphate or substituted phosphate.

In some embodiments of formula (II) or (IIa), n is 1. In some cases, n is greater than 1, such as 2, 3 or 4.

In some instances of formula (II) or (IIa), m is 1 to 14 so as to provide a substituted $C_{1-14}$ alkoxy group, such as a substituted $C_{1-12}$ alkoxy, substituted $C_{1-10}$ alkoxy, substituted $C_{1-8}$ alkoxy, substituted $C_{1-6}$ alkoxy, or substituted $C_{1-3}$ alkoxy. In some instances, m is 2, so as to provide a substituted $C_2$ alkoxy, such as substituted ethoxy. In some instances, m is 3, so as to provide a substituted $C_3$ alkoxy, such as substituted propoxy. In some instances, m is 6 so as to provide a substituted $C_6$ alkoxy, such as substituted hexyloxy. In some instances, m is 12 so as to provide a substituted $C_{12}$ alkoxy, such as substituted dodecyloxy. In some instances, X on the substituted alkoxy is amino or substituted amino. In some instances, X on the substituted alkoxy is amino, such that the group is an aminoalkoxy, such as aminopropoxy (e.g., 3-aminopropoxy) or aminohexyloxy (e.g., 6-aminohexyloxy). In some instances, X on the substituted alkoxy is thiol or substituted thiol. In some instances, X on the substituted alkoxy is thiol, such that the group is a thioalkoxy, such as thiopropoxy (e.g., 3-thiopropoxy), thiohexyloxy (e.g., 6-thiohexyloxy) or thiododecanoxy.

canoxy. In some embodiments, the organic ligand is attached to a nanoparticle through the aminoalkoxy or thioalkoxy substituent. For instance, in embodiments where formula (II) or (IIa) includes an aminoalkoxy group, the organic ligand may be attached to the nanoparticle through the amino group of the aminoalkoxy tether. In embodiments where formula (II) or (IIa) includes a thioalkoxy group, the organic ligand may be attached to the nanoparticle through the thiol group of the thioalkoxy.

In some instances of formula (II) or (IIa), $R^2$ is H or halo. In some instances, $R^2$ is H. $R^2$ is halo, such as fluoro.

In some instances of formula (II) or (IIa), $R^3$ is H or halo. In some instances, $R^3$ is H. $R^3$ is halo, such as fluoro.

In some instances of formula (II) or (IIa), $R^4$ is H or halo. In some instances, $R^4$ is H. $R^4$ is halo, such as fluoro.

In some instances of formula (II) or (IIa), $R^5$ is H or halo. In some instances, $R^5$ is H. $R^5$ is halo, such as fluoro.

In some instances of formula (II) or (IIa), $R^6$ is alkoxy or azido. In some instances, $R^6$ is azido. In some instances, $R^6$ is alkoxy, such as a $C_{1-14}$ alkoxy, $C_{1-12}$ alkoxy, $C_{1-10}$ alkoxy, $C_{1-8}$ alkoxy, $C_{1-6}$ alkoxy, or $C_{1-3}$ alkoxy. In some instances, $R^6$ is $C_5$ alkoxy, such as pentyloxy. In some instances, $R^6$ is $C_4$ alkoxy, such as butyloxy. In some instances, $R^6$ is $C_1$ alkoxy, such as methoxy. In some instances, $R^6$ is substituted alkoxy, such as a substituted $C_{1-14}$ alkoxy, substituted $C_{1-12}$ alkoxy, substituted $C_{1-10}$ alkoxy, substituted $C_{1-8}$ alkoxy, or substituted $C_{1-6}$ alkoxy. In some instances, $R^6$ is substituted $C_6$ alkoxy, such as substituted hexyloxy. In some instances, $R^6$ is substituted $C_{12}$ alkoxy, such as substituted dodecyloxy. In some instances, the substituent on the substituted alkoxy is phosphate or substituted phosphate.

In some instances of formula (II) or (IIa), $R^2$, $R^3$, $R^4$ and $R^5$ are each H. In some instances, when $R^2$, $R^3$, $R^4$ and $R^5$ are each H, $R^6$ is alkoxy or substituted alkoxy.

In some instances, $R^2$, $R^3$, $R^4$ and $R^5$ are each halo, such as fluoro. In some instances, when $R^2$, $R^3$, $R^4$ and $R^5$ are each halo (e.g., fluoro), $R^6$ is azido.

In some embodiments the organic ligand of formula (II), has the structure of formula (III):

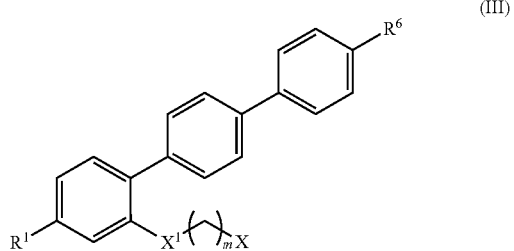

wherein:
$R^1$ is selected from halogen, hydroxyl, azido, alkyl, substituted alkyl, alkenyl, substituted alkenyl, alkynyl, substituted alkynyl, alkoxy, substituted alkoxy, amino, and substituted amino;
$R^6$ is selected from H, halogen, hydroxyl, azido, alkyl, substituted alkyl, alkenyl, substituted alkenyl, alkynyl, substituted alkynyl, alkoxy, substituted alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol;

X is an amine or a thiol group;
$X^1$ is selected from O, NR', $CR'_2$ and S, wherein each R' is independently selected from H, alkyl, substituted alkyl, alkenyl, substituted alkenyl, aryl, substituted aryl; and
m is an integer from 1 to 14.

In some embodiments the organic ligand of formula (II), has the structure of formula (IIIa):

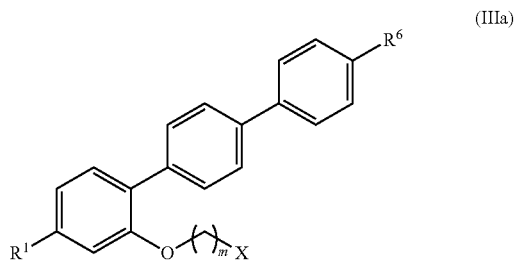

wherein:
$R^1$ is selected from halogen, hydroxyl, azido, alkyl, substituted alkyl, alkenyl, substituted alkenyl, alkynyl, substituted alkynyl, alkoxy, substituted alkoxy, amino, and substituted amino;
$R^6$ is selected from H, halogen, hydroxyl, azido, alkyl, substituted alkyl, alkenyl, substituted alkenyl, alkynyl, substituted alkynyl, alkoxy, substituted alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol;
X is an amine or a thiol group; and
m is an integer from 1 to 14.

In some instances of formula (III) or (IIIa), $R^1$ is alkoxy, such as a $C_{1-14}$ alkoxy, $C_{1-12}$ alkoxy, $C_{1-10}$ alkoxy, $C_{1-8}$ alkoxy, $C_{1-6}$ alkoxy, or $C_{1-3}$ alkoxy. In some instances, $R^1$ is $C_5$ alkoxy, such as pentyloxy. In some instances, $R^1$ is $C_4$ alkoxy, such as butyloxy. In some instances, $R^1$ is $C_1$ alkoxy, such as methoxy. In some instances, $R^1$ is substituted alkoxy, such as a substituted $C_{1-14}$ alkoxy, substituted $C_{1-12}$ alkoxy, substituted $C_{1-10}$ alkoxy, substituted $C_{1-8}$ alkoxy, or substituted $C_{1-6}$ alkoxy. In some instances, $R^1$ is substituted $C_6$ alkoxy, such as substituted hexyloxy. In some instances, $R^1$ is substituted $C_{12}$ alkoxy, such as substituted dodecyloxy. In some instances, the substituent on the substituted alkoxy is phosphate or substituted phosphate.

In some instances of formula (III) or (IIIa), m is 1 to 14 so as to provide a substituted $C_{1-14}$ alkoxy group, such as a substituted $C_{1-12}$ alkoxy, substituted $C_{1-10}$ alkoxy, substituted $C_{1-8}$ alkoxy, substituted $C_{1-6}$ alkoxy, or substituted $C_{1-3}$ alkoxy. In some instances, m is 2, so as to provide a substituted $C_2$ alkoxy, such as substituted ethoxy. In some instances, m is 3, so as to provide a substituted $C_3$ alkoxy, such as substituted propoxy. In some instances, m is 6 so as to provide a substituted $C_6$ alkoxy, such as substituted hexyloxy. In some instances, m is 12 so as to provide a substituted $C_{12}$ alkoxy, such as substituted dodecyloxy. In some instances, X on the substituted alkoxy is amino or substituted amino. In some instances, X on the substituted alkoxy is amino, such that the group is an aminoalkoxy, such as aminopropoxy (e.g., 3-aminopropoxy) or aminohexyloxy (e.g., 6-aminohexyloxy). In some instances, X on the substituted alkoxy is thiol or substituted thiol. In some instances, X on the substituted alkoxy is thiol, such that the group is a thioalkoxy, such as thiopropoxy (e.g., 3-thiopropoxy), thiohexyloxy (e.g., 6-thiohexyloxy) or thiododecanoxy. In some embodiments, the organic ligand is attached to a nanoparticle through the aminoalkoxy or thioalkoxy substituent. For instance, in embodiments where formula (III) or (IIIa) includes an aminoalkoxy group, the organic ligand may be attached to the nanoparticle through the amino group of the aminoalkoxy tether. In embodiments where formula (III) or (IIIa) includes a thioalkoxy group, the organic ligand may be attached to the nanoparticle through the thiol group of the thioalkoxy.

In some instances of formula (III) or (IIIa), $R^6$ is alkoxy or azido. In some instances, $R^6$ is azido. In some instances, $R^6$ is alkoxy, such as a $C_{1-14}$ alkoxy, $C_{1-12}$ alkoxy, $C_{1-10}$ alkoxy, $C_{1-8}$ alkoxy, $C_{1-6}$ alkoxy, or $C_{1-3}$ alkoxy. In some instances, $R^6$ is $C_5$ alkoxy, such as pentyloxy. In some instances, $R^6$ is $C_4$ alkoxy, such as butyloxy. In some instances, $R^6$ is $C_1$ alkoxy, such as methoxy. In some instances, $R^6$ is substituted alkoxy, such as a substituted $C_{1-14}$ alkoxy, substituted $C_{1-12}$ alkoxy, substituted $C_{1-10}$ alkoxy, substituted $C_{1-8}$ alkoxy, or substituted $C_{1-6}$ alkoxy. In some instances, $R^6$ is substituted $C_6$ alkoxy, such as substituted hexyloxy. In some instances, $R^6$ is substituted $C_{12}$ alkoxy, such as substituted dodecyloxy. In some instances, the substituent on the substituted alkoxy is phosphate or substituted phosphate.

In some embodiments the organic ligand of formula (I), has the structure of formula (IV):

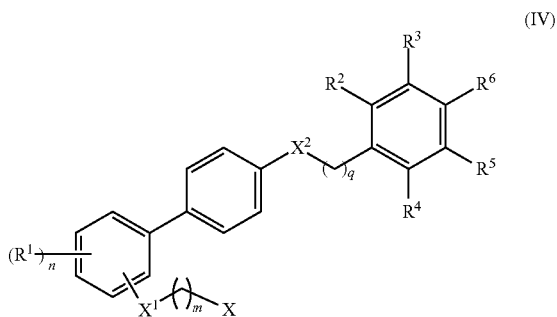

(IV)

wherein:
$R^1$ are each independently selected from H, halogen, hydroxyl, azido, alkyl, substituted alkyl, alkenyl, substituted alkenyl, alkynyl, substituted alkynyl, alkoxy, substituted alkoxy, amino, and substituted amino;
$R^2$, $R^3$, $R^4$, $R^5$, and $R^6$ are each independently selected from H, halogen, hydroxyl, azido, alkyl, substituted alkyl, alkenyl, substituted alkenyl, alkynyl, substituted alkynyl, alkoxy, substituted alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol;
X is an amine or a thiol group;
$X^1$ is selected from O, NR', $CR'_2$ and S, wherein each R' is independently selected from H, alkyl, substituted alkyl, alkenyl, substituted alkenyl, aryl, substituted aryl;
$X^2$ is selected from O, NR', $CR'_2$ and S, wherein each R' is independently selected from H, alkyl, substituted alkyl, alkenyl, substituted alkenyl, aryl, substituted aryl;
n is an integer from 1 to 4; and
m and q are each independently an integer from 1 to 14.

In some embodiments the organic ligand of formula (I), has the structure of formula (IV):

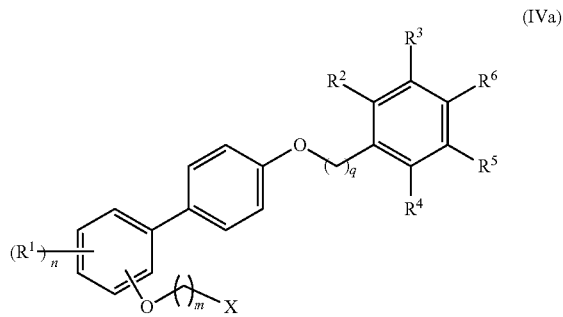

(IVa)

wherein:
$R^1$ are each independently selected from H, halogen, hydroxyl, azido, alkyl, substituted alkyl, alkenyl, substituted alkenyl, alkynyl, substituted alkynyl, alkoxy, substituted alkoxy, amino, and substituted amino;
$R^2$, $R^3$, $R^4$, $R^5$, and $R^6$ are each independently selected from H, halogen, hydroxyl, azido, alkyl, substituted alkyl, alkenyl, substituted alkenyl, alkynyl, substituted alkynyl, alkoxy, substituted alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol;
X is an amine or a thiol group;
n is an integer from 1 to 4; and
m and q are each independently an integer from 1 to 14.

In some instances of formula (IV) or (IVa), $R^1$ is alkoxy, such as a $C_{1-14}$ alkoxy, $C_{1-12}$ alkoxy, $C_{1-10}$ alkoxy, $C_{1-8}$ alkoxy, $C_{1-6}$ alkoxy, or $C_{1-3}$ alkoxy. In some instances, $R^1$ is $C_5$ alkoxy, such as pentyloxy. In some instances, $R^1$ is $C_4$ alkoxy, such as butyloxy. In some instances, $R^1$ is $C_1$ alkoxy, such as methoxy. In some instances, $R^1$ is substituted alkoxy, such as a substituted $C_{1-14}$ alkoxy, substituted $C_{1-12}$ alkoxy, substituted $C_{1-10}$ alkoxy, substituted $C_{1-8}$ alkoxy, or substituted $C_{1-6}$ alkoxy. In some instances, $R^1$ is substituted $C_6$ alkoxy, such as substituted hexyloxy. In some instances, $R^1$ is substituted $C_{12}$ alkoxy, such as substituted dodecyloxy. In some instances, the substituent on the substituted alkoxy is phosphate or substituted phosphate.

In some embodiments of formula (IV) or (IVa), n is 1. In some cases, n is greater than 1, such as 2, 3 or 4.

In some instances of formula (IV) or (IVa), m is 1 to 14 so as to provide a substituted $C_{1-14}$ alkoxy group, such as a substituted $C_{1-12}$ alkoxy, substituted $C_{1-10}$ alkoxy, substituted $C_{1-8}$ alkoxy, substituted $C_{1-6}$ alkoxy, or substituted $C_{1-3}$ alkoxy. In some instances, m is 2, so as to provide a substituted $C_2$ alkoxy, such as substituted ethoxy. In some instances, m is 3, so as to provide a substituted $C_3$ alkoxy, such as substituted propoxy. In some instances, m is 6 so as to provide a substituted $C_6$ alkoxy, such as substituted hexyloxy. In some instances, m is 12 so as to provide a substituted $C_{12}$ alkoxy, such as substituted dodecyloxy. In some instances, X on the substituted alkoxy is amino or substituted amino. In some instances, X on the substituted alkoxy is amino, such that the group is an aminoalkoxy, such as aminopropoxy (e.g., 3-aminopropoxy) or aminohexyloxy (e.g., 6-aminohexyloxy). In some instances, X on the substituted alkoxy is thiol or substituted thiol. In some instances, X on the substituted alkoxy is thiol, such that the group is a thioalkoxy, such as thiopropoxy (e.g., 3-thiopropoxy), thiohexyloxy (e.g., 6-thiohexyloxy) or thiododecanoxy. In some embodiments, the organic ligand is attached to a nanoparticle through the aminoalkoxy or thioalkoxy substituent. For instance, in embodiments where formula (IV) or (IVa) includes an aminoalkoxy group, the organic ligand may be attached to the nanoparticle through the amino group of the aminoalkoxy tether. In embodiments where formula (IV) or (IVa) includes a thioalkoxy group, the organic ligand may be attached to the nanoparticle through the thiol group of the thioalkoxy.

In some instances of formula (IV) or (IVa), q is 1 to 14 so as to provide a substituted $C_{1-14}$ alkoxy group, such as a substituted $C_{1-12}$ alkoxy, substituted $C_{1-10}$ alkoxy, substituted $C_{1-8}$ alkoxy, substituted $C_{1-6}$ alkoxy, or substituted $C_{1-3}$ alkoxy. In some instances, q is 1, so as to provide a substituted $C_1$ alkoxy, such as substituted methoxy. In some instances, q is 2, so as to provide a substituted $C_2$ alkoxy, such as substituted ethoxy. In some instances, q is 3, so as to provide a substituted $C_3$ alkoxy, such as substituted propoxy. In some instances, q is 6 so as to provide a substituted $C_6$ alkoxy, such as substituted hexyloxy. In some instances, q is 12 so as to provide a substituted $C_{12}$ alkoxy, such as substituted dodecyloxy.

In some instances of formula (IV) or (IVa), $R^2$ is H or halo. In some instances, $R^2$ is H. $R^2$ is halo, such as fluoro.

In some instances of formula (IV) or (IVa), $R^3$ is H or halo. In some instances, $R^3$ is H. $R^3$ is halo, such as fluoro.

In some instances of formula (IV) or (IVa), $R^4$ is H or halo. In some instances, $R^4$ is H. $R^4$ is halo, such as fluoro.

In some instances of formula (IV) or (IVa), $R^5$ is H or halo. In some instances, $R^5$ is H. $R^5$ is halo, such as fluoro.

In some instances of formula (IV) or (IVa), $R^6$ is alkoxy or azido. In some instances, $R^6$ is azido. In some instances, $R^6$ is alkoxy, such as a $C_{1-14}$ alkoxy, $C_{1-12}$ alkoxy, $C_{1-10}$ alkoxy, $C_{1-8}$ alkoxy, $C_{1-6}$ alkoxy, or $C_{1-3}$ alkoxy. In some instances, $R^6$ is $C_5$ alkoxy, such as pentyloxy. In some instances, $R^6$ is $C_4$ alkoxy, such as butyloxy. In some instances, $R^6$ is $C_1$ alkoxy, such as methoxy. In some instances, $R^6$ is substituted alkoxy, such as a substituted $C_{1-14}$ alkoxy, substituted $C_{1-12}$ alkoxy, substituted $C_{1-10}$ alkoxy, substituted $C_{1-8}$ alkoxy, or substituted $C_{1-6}$ alkoxy. In some instances, $R^6$ is substituted $C_6$ alkoxy, such as substituted hexyloxy. In some instances, $R^6$ is substituted $C_{12}$ alkoxy, such as substituted dodecyloxy. In some instances, the substituent on the substituted alkoxy is phosphate or substituted phosphate.

In some instances of formula (IV) or (IVa), $R^2$, $R^3$, $R^4$ and $R^5$ are each H. In some instances, when $R^2$, $R^3$, $R^4$ and $R^5$ are each H, $R^6$ is alkoxy or substituted alkoxy.

In some instances of formula (IV) or (IVa), $R^2$, $R^3$, $R^4$ and $R^5$ are each halo, such as fluoro. In some instances, when $R^2$, $R^3$, $R^4$ and $R^5$ are each halo (e.g., fluoro), $R^6$ is azido.

In some embodiments the organic ligand of formula (IV), has the structure of formula (V):

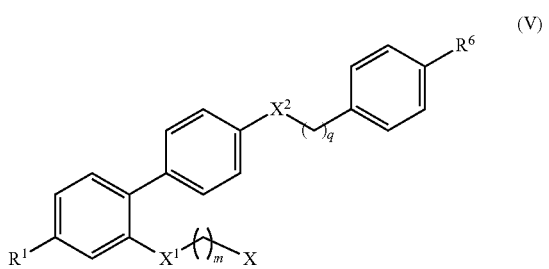

wherein:
$R^1$ is selected from halogen, hydroxyl, azido, alkyl, substituted alkyl, alkenyl, substituted alkenyl, alkynyl, substituted alkynyl, alkoxy, substituted alkoxy, amino, and substituted amino;

$R^6$ is selected from H, halogen, hydroxyl, azido, alkyl, substituted alkyl, alkenyl, substituted alkenyl, alkynyl, substituted alkynyl, alkoxy, substituted alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol;

X is an amine or a thiol group;

$X^1$ is selected from O, NR', CR'$_2$ and S, wherein each R' is independently selected from H, alkyl, substituted alkyl, alkenyl, substituted alkenyl, aryl, substituted aryl;

$X^2$ is selected from O, NR', CR'$_2$ and S, wherein each R' is independently selected from H, alkyl, substituted alkyl, alkenyl, substituted alkenyl, aryl, substituted aryl; and m and q are each independently an integer from 1 to 14.

In some embodiments the organic ligand of formula (IV), has the structure of formula (Va):

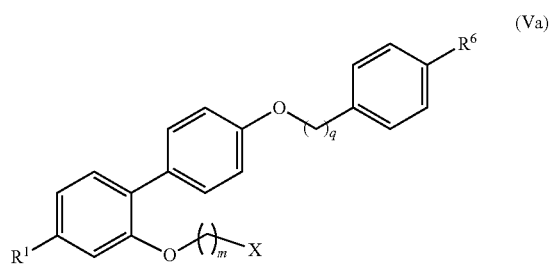

wherein:
$R^1$ is selected from halogen, hydroxyl, azido, alkyl, substituted alkyl, alkenyl, substituted alkenyl, alkynyl, substituted alkynyl, alkoxy, substituted alkoxy, amino, and substituted amino;

$R^6$ is selected from H, halogen, hydroxyl, azido, alkyl, substituted alkyl, alkenyl, substituted alkenyl, alkynyl, substituted alkynyl, alkoxy, substituted alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol;

X is an amine or a thiol group; and m and q are each independently an integer from 1 to 14.

In some instances of formula (V) or (Va), $R^1$ is alkoxy, such as a $C_{1-14}$ alkoxy, $C_{1-12}$ alkoxy, $C_{1-10}$ alkoxy, $C_{1-8}$ alkoxy, $C_{1-6}$ alkoxy, or $C_{1-3}$ alkoxy. In some instances, $R^1$ is $C_5$ alkoxy, such as pentyloxy. In some instances, $R^1$ is $C_4$ alkoxy, such as butyloxy. In some instances, $R^1$ is $C_1$ alkoxy, such as methoxy. In some instances, $R^1$ is substituted alkoxy, such as a substituted $C_{1-14}$ alkoxy, substituted $C_{1-12}$ alkoxy, substituted $C_{1-10}$ alkoxy, substituted $C_{1-8}$ alkoxy, or substituted $C_{1-6}$ alkoxy. In some instances, $R^1$ is substituted $C_6$ alkoxy, such as substituted hexyloxy. In some instances, $R^1$ is substituted $C_{12}$ alkoxy, such as substituted dodecyloxy. In some instances, the substituent on the substituted alkoxy is phosphate or substituted phosphate.

In some embodiments of formula (V) or (Va), n is 1. In some cases, n is greater than 1, such as 2, 3 or 4.

In some instances of formula (V) or (Va), m is 1 to 14 so as to provide a substituted $C_{1-14}$ alkoxy group, such as a substituted $C_{1-12}$ alkoxy, substituted $C_{1-10}$ alkoxy, substituted $C_{1-8}$ alkoxy, substituted $C_{1-6}$ alkoxy, or substituted $C_{1-3}$ alkoxy. In some instances, m is 2, so as to provide a substituted $C_2$ alkoxy, such as substituted ethoxy. In some instances, m is 3, so as to provide a substituted $C_3$ alkoxy, such as substituted propoxy. In some instances, m is 6 so as to provide a substituted $C_6$ alkoxy, such as substituted hexyloxy. In some instances, m is 12 so as to provide a substituted $C_{12}$ alkoxy, such as substituted dodecyloxy. In some instances, X on the substituted alkoxy is amino or substituted amino. In some instances, X on the substituted alkoxy is amino, such that the group is an aminoalkoxy, such as aminopropoxy (e.g., 3-aminopropoxy) or aminohexyloxy (e.g., 6-aminohexyloxy). In some instances, X on the substituted alkoxy is thiol or substituted thiol. In some instances, X on the substituted alkoxy is thiol, such that the group is a thioalkoxy, such as thiopropoxy (e.g., 3-thiopropoxy), thiohexyloxy (e.g., 6-thiohexyloxy) or thiododecanoxy. In some embodiments, the organic ligand is attached to a nanoparticle through the aminoalkoxy or thioalkoxy substituent. For instance, in embodiments where formula (V) or (Va) includes an aminoalkoxy group, the organic ligand may be attached to the nanoparticle through the amino group of the aminoalkoxy tether. In embodiments where formula (V) or (Va) includes a thioalkoxy group, the organic ligand may be attached to the nanoparticle through the thiol group of the thioalkoxy.

In some instances of formula (V) or (Va), q is 1 to 14 so as to provide a substituted $C_{1-14}$ alkoxy group, such as a substituted $C_{1-12}$ alkoxy, substituted $C_{1-10}$ alkoxy, substituted $C_{1-8}$ alkoxy, substituted $C_{1-6}$ alkoxy, or substituted $C_{1-3}$ alkoxy. In some instances, q is 1, so as to provide a substituted $C_1$ alkoxy, such as substituted methoxy. In some instances, q is 2, so as to provide a substituted $C_2$ alkoxy, such as substituted ethoxy. In some instances, q is 3, so as to provide a substituted $C_3$ alkoxy, such as substituted propoxy. In some instances, q is 6 so as to provide a substituted $C_6$ alkoxy, such as substituted hexyloxy. In some instances, q is 12 so as to provide a substituted $C_{12}$ alkoxy, such as substituted dodecyloxy.

In some instances of formula (V) or (Va), $R^6$ is alkoxy or azido. In some instances, $R^6$ is azido. In some instances, $R^6$ is alkoxy, such as a $C_{1-14}$ alkoxy, $C_{1-12}$ alkoxy, $C_{1-10}$ alkoxy, $C_{1-8}$ alkoxy, $C_{1-6}$ alkoxy, or $C_{1-3}$ alkoxy. In some instances, $R^6$ is $C_5$ alkoxy, such as pentyloxy. In some instances, $R^6$ is $C_4$ alkoxy, such as butyloxy. In some instances, $R^6$ is $C_1$ alkoxy, such as methoxy. In some instances, $R^6$ is substituted alkoxy, such as a substituted $C_{1-14}$ alkoxy, substituted $C_{1-12}$ alkoxy, substituted $C_{1-10}$ alkoxy, substituted $C_{1-8}$ alkoxy, or substituted $C_{1-6}$ alkoxy. In some instances, $R^6$ is substituted $C_6$ alkoxy, such as substituted hexyloxy. In some instances, $R^6$ is substituted $C_{12}$ alkoxy, such as substituted dodecyloxy. In some instances, the substituent on the substituted alkoxy is phosphate or substituted phosphate.

In certain embodiments of an organic ligand of any one of formulae (I) to (V), $R^1$ is $C_1$-$C_{12}$ alkoxy. In certain embodiments of an organic ligand of any one of formulas (I) to (V), $R^6$ is $C_1$-$C_{12}$ alkoxy.

In some embodiments of an organic ligand of any one of formulae (I) to (V), $X^1$ is O. In some embodiments of an organic ligand of any one of formulae (I) to (V), $X^1$ is NR', and R' is selected from a group as defined herein. In some embodiments of an organic ligand of any one of formulae (I) to (V), $X^1$ is CR'$_2$ and each R' are independently selected from a group as defined herein. In some embodiments of an organic ligand of any one of formulae (I) to (V), $X^1$ is S. In some embodiments of an organic ligand of formulae (IV) or (V), $X^2$ is O. In some embodiments of an organic ligand of formulae (IV) or (V), $X^2$ is NR', and R' is selected from a group as defined herein. In some embodiments of an organic ligand of formulae (IV) or (V), $X^2$ is CR'$_2$ and each R' are independently selected from a group as defined herein. In some embodiments of an organic ligand of formulae (IV) or (V), $X^2$ is S.

In some embodiments a subject organic ligand is selected from:

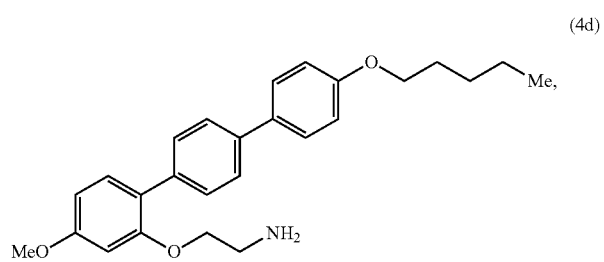

(4d)

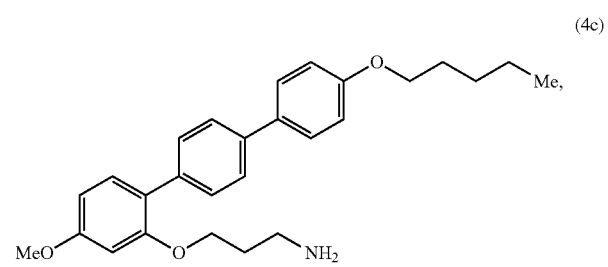

(4c)

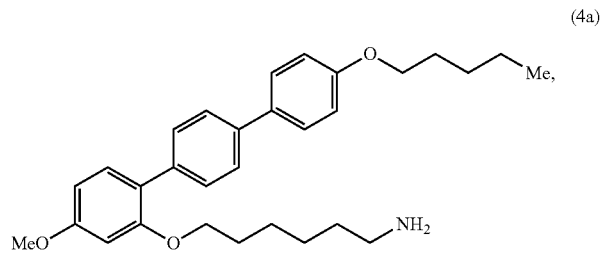

(4a)

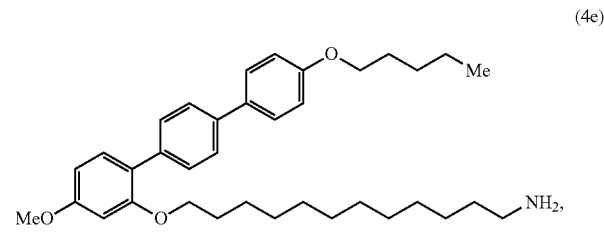

(4e)

-continued

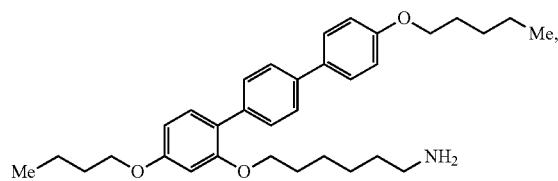
(4f)

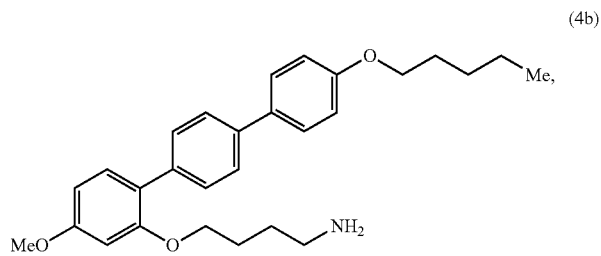
(4i)

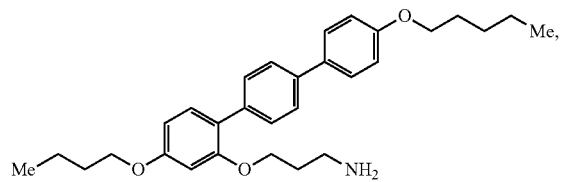
(4g)

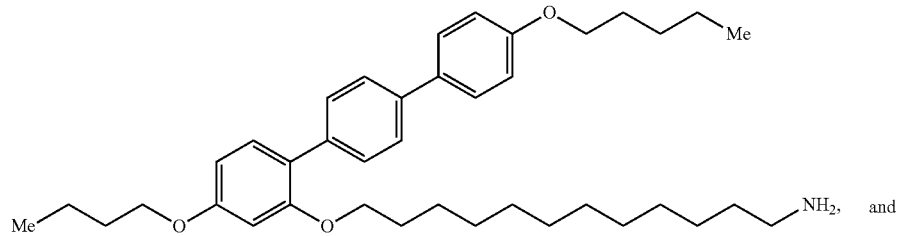
(4b)

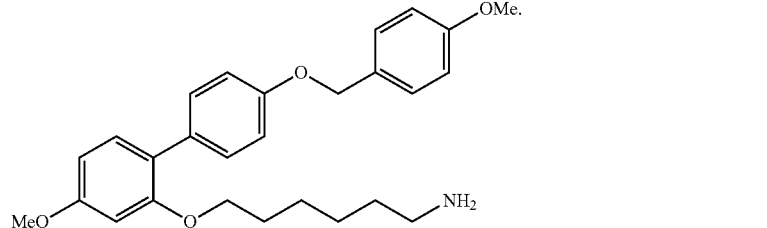
(4h)

and

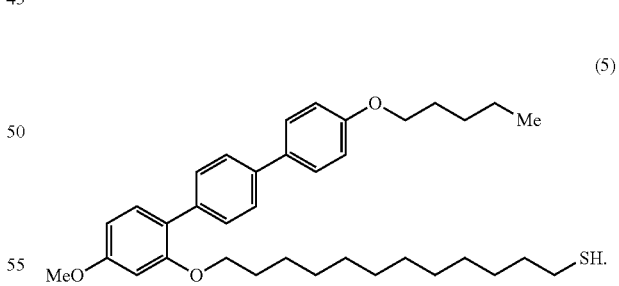
(4j)

In certain embodiments of the organic ligand of the structure (4e), the amine group is replaced with a thiol group. In certain embodiments of the organic ligand of the structure (4d), the amine group is replaced with a thiol group. In certain embodiments of the organic ligand of the structure (4b), the amine group is replaced with a thiol group. In certain embodiments of the organic ligand of the structure (4a), the amine group is replaced with a thiol group. In certain embodiments of the organic ligand of the structure (4g), the amine group is replaced with a thiol group. In certain embodiments of the organic ligand of the structure (4i), the amine group is replaced with a thiol group.

In certain embodiments of the mesogenic ligand of the structure (4h), the amine group is replaced with a thiol group. In certain embodiments of the mesogenic ligand of the structure (4c), the amine group is replaced with a thiol group. In certain embodiments of the mesogenic ligand of the structure (4f), the amine group is replaced with a thiol group. In certain embodiments of the mesogenic ligand of the structure (4j), the amine group is replaced with a thiol group.

In some embodiments, the organic ligand of formulae (I), (II) or (III) is of the structure (5):

(5)

Embodiments of the present disclosure include organic ligands (e.g., as described herein), salts thereof, and/or solvate, hydrate forms thereof. In addition, it is understood that, in any compound described herein having one or more chiral centers, if an absolute stereochemistry is not expressly indicated, then each center may independently be of R-configuration or S configuration or a mixture thereof. It will be appreciated that all permutations of salts, solvates, hydrates, and stereoisomers are meant to be encompassed by the present disclosure.

Methods of Organic Ligand Preparation

As summarized above, the present disclosure provides methods of preparing a variety of organic ligands, including but not limited to, any of the organic ligands of formulas (I) to (V) and any of the structures (4a) to (4j). The subject methods provide for the synthesis of the subject organic ligands in high yield and purity. The synthetic routes provided by the subject methods involve combinations of particular reaction intermediates, particular synthetic methods, particular protecting group chemistries and strategies, and/or particular purification strategies, examples of which are described in length herein. The particular nature and unique sequence of steps with which these reaction intermediates are combined in the subject methods provides for a direct and concise synthesis of a variety of stable organic ligands in high purity.

In general terms, the subject methods provide several significant methodological innovations including, but not limited to:

(a) first-in-kind synthesis of the subject organic ligands;

(b) concise methodology for generating a library of highly stable organic ligands of high purity for use in templatable mesoscale nanocapsules.

In some embodiments, the method is a method of preparing a compound of formula (VII) from a compound of formula (VI):

(VI) [structure: benzene ring with $(R^1)_n$, Z, and $X^1$ substituents] + M—L—Y →

(VII) [structure: benzene ring with $(R^1)_n$, L—Y, and $X^1$ substituents]

wherein:

Z is a leaving group,

M is selected from a substituted metalloid or a substituted metal;

L is selected from phenyl, substituted phenyl, biphenyl and substituted biphenyl;

Y is selected from H, halogen, hydroxyl, azido, phenyl, substituted phenyl, biphenyl, substituted biphenyl, alkoxy, substituted alkoxy, alkyl, substituted alkyl, amino, substituted amino, cycloalkyl, substituted cycloalkyl, heterocycloalkyl, and substituted heterocycloalkyl;

$R^1$ are each independently selected from H, halogen, hydroxyl, azido, alkyl, substituted alkyl, alkenyl, substituted alkenyl, alkynyl, substituted alkynyl, alkoxy, substituted alkoxy, amino, and substituted amino;

$X^1$ is selected from O, NR', $CR'_2$ and S, wherein each R' is independently selected from H, alkyl, substituted alkyl, alkenyl, substituted alkenyl, aryl, substituted aryl; and n is an integer from 1 to 4.

In some embodiments, the method is a method of preparing a compound of formula (VIIa) from a compound of formula (VIa):

(VIa) [structure: benzene ring with $(R^1)_n$, Z, and OH substituents] + M—L—Y →

(VIIa) [structure: benzene ring with $(R^1)_n$, L—Y, and OH substituents]

wherein:

Z is a leaving group,

M is selected from a substituted metalloid or a substituted metal;

L is selected from phenyl, substituted phenyl, biphenyl and substituted biphenyl;

Y is selected from H, halogen, hydroxyl, azido, phenyl, substituted phenyl, biphenyl, substituted biphenyl, alkoxy, substituted alkoxy, alkyl, substituted alkyl, amino, substituted amino, cycloalkyl, substituted cycloalkyl, heterocycloalkyl, and substituted heterocycloalkyl;

$R^1$ are each independently selected from H, halogen, hydroxyl, azido, alkyl, substituted alkyl, alkenyl, substituted alkenyl, alkynyl, substituted alkynyl, alkoxy, substituted alkoxy, amino, and substituted amino; and n is an integer from 1 to 4.

In general, a compound of formula (VII) or (VIIa) may be prepared by a cross-coupling reaction of a first aromatic compound and second aromatic compound, such as a metal-catalyzed coupling of organometallic reagents with aryl electrophiles or metal-catalyzed coupling of organometallic reagents with aryl halides.

In some embodiments, the leaving group Z is selected from a halide (e.g. chloride, bromide or iodide), a triflate, a tosylate and a mesylate. In certain embodiments, Z is a halide. In certain embodiments, Z is bromide. In certain embodiments, Z is chloride. In certain embodiments, Z is iodide.

In some embodiments, M is selected from a boron reagent (e.g. a boronic acid or a boronic ester), a zinc reagent (e.g. zinc chloride), a magnesium reagent (e.g. a Grignard reagent), a silicon reagent (e.g. an organosilane reagent), and a tin reagent (e.g. an organotin reagent).

In some embodiments, the method is a method of preparing a compound of formula (VII) from a compound of formula (VI) via a Suzuki coupling between a compound of formula (VI) and a derivative of formula (VIII):

(VI) [structure: benzene ring with $(R^1)_n$, Z, and $X^1$ substituents] + (VIII) [structure: $R^7$—B(—$R^7$)—L—Y] →

-continued $$\underset{(VII)}{(R^1)_n \diagdown \diagdown X^1}^{L \diagdown Y}$$

wherein:

Z is a leaving group;

L is selected from phenyl, substituted phenyl, biphenyl and substituted biphenyl;

Y is selected from H, halogen, hydroxyl, azido, phenyl, substituted phenyl, biphenyl, substituted biphenyl, alkoxy, substituted alkoxy, alkyl, substituted alkyl, amino, substituted amino, cycloalkyl, substituted cycloalkyl, heterocycloalkyl, and substituted heterocycloalkyl;

$R^1$ are each independently selected from H, halogen, hydroxyl, azido, alkyl, substituted alkyl, alkenyl, substituted alkenyl, alkynyl, substituted alkynyl, alkoxy, substituted alkoxy, amino, and substituted amino;

$R^7$ are each independently selected from hydroxyl, alkyl, substituted alkyl, heteroalkyl and substituted heteroalkyl;

or both $R^7$ groups together with the boron to which they are attached form a group selected from heterocycle, substituted heterocycle, cycloalkyl, substituted cycloalkyl;

$X^1$ is selected from O, NR', CR'$_2$ and S, wherein each R' is independently selected from H, alkyl, substituted alkyl, alkenyl, substituted alkenyl, aryl, substituted aryl; and n is an integer from 1 to 4.

In some embodiments, the method is a method of preparing a compound of formula (VIIa) from a compound of formula (VIa) via a Suzuki coupling between a compound of formula (VIa) and a derivative of formula (VIII):

$$\underset{(VIa)}{(R^1)_n \diagdown \diagdown OH}^{Z} \quad \underset{(VIII)}{R^7 \diagdown B \diagdown L \diagdown Y}^{R^7} \longrightarrow$$

$$\underset{(VIIa)}{(R^1)_n \diagdown \diagdown OH}^{L \diagdown Y}$$

wherein:

Z is a leaving group;

L is selected from phenyl, substituted phenyl, biphenyl and substituted biphenyl;

Y is selected from H, halogen, hydroxyl, azido, phenyl, substituted phenyl, biphenyl, substituted biphenyl, alkoxy, substituted alkoxy, alkyl, substituted alkyl, amino, substituted amino, cycloalkyl, substituted cycloalkyl, heterocycloalkyl, and substituted heterocycloalkyl;

$R^1$ are each independently selected from H, halogen, hydroxyl, azido, alkyl, substituted alkyl, alkenyl, substituted alkenyl, alkynyl, substituted alkynyl, alkoxy, substituted alkoxy, amino, and substituted amino;

$R^7$ are each independently selected from hydroxyl, alkyl, substituted alkyl, heteroalkyl and substituted heteroalkyl;

or both $R^7$ groups together with the boron to which they are attached form a group selected from heterocycle, substituted heterocycle, cycloalkyl, substituted cycloalkyl; and n is an integer from 1 to 4.

In some embodiments, the leaving group Z is selected from a halide (e.g. chloride, bromide or iodide), a triflate, a tosylate and a mesylate. In certain embodiments, Z is a halide. In certain embodiments, Z is bromide. In certain embodiments, Z is chloride. In certain embodiments, Z is iodide. In some embodiments, Z is a tosylate.

In some embodiments of a compound of formula (VIII), the $R^7$ groups are both hydroxyl groups, such that a compound of formula (VIII) is a boronic acid.

In some embodiments of a compound of formula (VIII), the $R^7$ groups are both alkyl groups or substituted alkyl groups, each independently selected from $C_1$-$C_6$ alkyl, such as methyl, ethyl, propyl, butyl, pentyl or hexyl. In some instances, each $R^7$ group is the same alkyl group. In some instances, both $R^7$ groups together with the boron to which they are attached form a cycloalkyl group, e.g. —B$R^7_2$ taken together may represent 9-borobicyclo[3.3.1]nonyl.

In some embodiments of a compound of formula (VIII), the $R^7$ groups are both heteroalkyl groups or substituted heteroalkyl groups, each independently selected from $C_1$-$C_6$ heteroalkyl, such as $C_1$-$C_6$ alkoxy. In some instances, each $R^7$ group is the same heteroalkyl group. In some instances, both $R^7$ groups together with the boron to which they are attached form a heterocycle group or a substituted heterocycle group, e.g. —B$R^7_2$ taken together may represent 4,4,5,5-tetramethyl-1,3,2-dioxaborolane or boronic acid 1,3-propanediol ester.

In some embodiments, the method is a method of preparing a compound of formula (VII) from a compound of formula (VI) via a Suzuki coupling between a compound of formula (VI) and a potassium trifluoroborate of formula (VIII'):

$$\underset{(VI)}{(R^1)_n \diagdown \diagdown X^1}^{Z} \quad \underset{(VIII')}{KF_3B \diagdown L \diagdown Y} \longrightarrow$$

$$\underset{(VII)}{(R^1)_n \diagdown \diagdown X^1}^{L \diagdown Y}$$

some embodiments, the method is a method of preparing a compound of formula (VIIa) from a compound of formula (VIa) via a Suzuki coupling between a compound of formula (VIa) and a potassium trifluoroborate of formula (VIII'):

$$\underset{(VIa)}{(R^1)_n \diagdown \diagdown OH}^{Z} \quad \underset{(VIII')}{KF_3B \diagdown L \diagdown Y} \longrightarrow$$

(VIIa)

[Structure: benzene ring with (R¹)ₙ substituent, L-Y group, and OH group]

In some embodiments, the compound of formula (VII) or (VIIa) is prepared by a method disclosed herein including a catalytic amount of a catalyst. The term "catalytic amount" is recognized in the art and refers to a substoichiometric amount of reagent relative to a reactant. As used herein, a catalytic amount means from 0.0001 to 90 mole percent reagent relative to a reactant, such as from 0.001 to 50 mole percent, from 0.01 to 10 mole percent, or from 0.1 to 5 mole percent reagent to reactant. In certain embodiments, the catalyst is used in an amount of 5 mol % or less.

In some embodiments, the coupling reaction to prepare a compound of formula (VII) or (VIIa) is catalyzed by a palladium catalyst. In certain embodiments, the catalyst is palladium acetate. In some cases, the catalyst is a palladium is tetrakis(triphenylphosphine)palladium(0). In some cases, the palladium catalyst is tetrakis(triphenylphosphine)palladium chloride.

In some embodiments, the coupling reaction to prepare a compound of formula (VII) or (VIIa) is catalyzed by a metal other than palladium. In some instances, the coupling reaction is catalyzed by a nickel catalyst.

It will be understood that any number of suitable catalyst may be used to prepare a compound formula (VIIa) in the subject methods.

In some embodiments the method further involves preparing an organic ligand of formula (IX) from the compound of formula (VII):

[Reaction scheme: (VII) → (IX)]

wherein:

L is selected from phenyl, substituted phenyl, biphenyl and substituted biphenyl;

Y is selected from H, halogen, hydroxyl, azido, phenyl, substituted phenyl, biphenyl, substituted biphenyl, alkoxy, substituted alkoxy, alkyl, substituted alkyl, amino, substituted amino, cycloalkyl, substituted cycloalkyl, heterocycloalkyl, and substituted heterocycloalkyl;

R¹ are each independently selected from H, halogen, hydroxyl, azido, alkyl, substituted alkyl, alkenyl, substituted alkenyl, alkynyl, substituted alkynyl, alkoxy, substituted alkoxy, amino, and substituted amino;

X is an amine or a thiol group;

P is a protecting group;

X¹ is selected from O, NR', CR'₂ and S, wherein each R' is independently selected from H, alkyl, substituted alkyl, alkenyl, substituted alkenyl, aryl, substituted aryl;

n is an integer from 1 to 4; and m is an integer from 1 to 14.

In some embodiments the method further involves preparing an organic ligand of formula (IXa) from the compound of formula (VIIa):

[Reaction scheme: (VIIa) → (IXa)]

wherein:

L is selected from phenyl, substituted phenyl, biphenyl and substituted biphenyl;

Y is selected from H, halogen, hydroxyl, azido, phenyl, substituted phenyl, biphenyl, substituted biphenyl, alkoxy, substituted alkoxy, alkyl, substituted alkyl, amino, substituted amino, cycloalkyl, substituted cycloalkyl, heterocycloalkyl, and substituted heterocycloalkyl;

R¹ are each independently selected from H, halogen, hydroxyl, azido, alkyl, substituted alkyl, alkenyl, substituted alkenyl, alkynyl, substituted alkynyl, alkoxy, substituted alkoxy, amino, and substituted amino;

X is an amine or a thiol group;

P is a protecting group;

n is an integer from 1 to 4; and m is an integer from 1 to 14.

In some cases, X is an amine and P is a protecting group suitable for an amine, such as a carbamate. In some cases, P is selected from a t-butyl carbamate (Boc), allyl carbamate (Alloc), benzyl carbamate (Cbz), 9-fluorenylmethyl carbamate (Fmoc), 2,2,2-trichloroethyl carbamate (Troc) and, 2-trimethylsilylethyl carbamate (Teoc). In certain instances, P is a t-butyl carbamate group (Boc).

In some cases, X is a thiol and P is a protecting group suitable for a thiol, such as an acetal. In some cases, X is a thiol group and P is a carbonyl containing protecting group (e.g., —C(O)Me such that XP together form a thioacetate).

In embodiments the method of preparing an organic ligand of formula (IX), includes reaction of a compound of formula (VII) with a compound of formula (X):

(X)

$L^1 \overset{\frown}{_p} XP$ wherein:

$L^1$ is a leaving group. Any convenient leaving group can be used in the compound of formula (X). In some cases, the leaving group $L^1$ in a compound of formula (X) is selected from a halide (e.g. such as, chloride, bromide or iodide), a triflate, a tosylate and a mesylate. In certain embodiments, $L^1$ is a halide. In certain embodiments, $L^1$ is bromide. In certain embodiments, $L^1$ is chloride. In certain embodiments, $L^1$ is iodide. In some embodiments, $L^1$ is a tosylate. In certain embodiments $L^1$ is a mesylate.

In some embodiments the method further involves preparing an organic ligand of formula (I) from the compound of formula (IX):

$(R^1)_n$—[phenyl ring with L-Y]—$X^1$—$(\ )_m$—XP (IX)

→

$(R^1)_n$—[phenyl ring with L-Y]—$X^1$—$(\ )_m$—X (I)

wherein:
L is selected from phenyl, substituted phenyl, biphenyl and substituted biphenyl;
Y is selected from H, halogen, hydroxyl, azido, phenyl, substituted phenyl, biphenyl, substituted biphenyl, alkoxy, substituted alkoxy, alkyl, substituted alkyl, amino, substituted amino, cycloalkyl, substituted cycloalkyl, heterocycloalkyl, and substituted heterocycloalkyl;
$R^1$ are each independently selected from H, halogen, hydroxyl, azido, alkyl, substituted alkyl, alkenyl, substituted alkenyl, alkynyl, substituted alkynyl, alkoxy, substituted alkoxy, amino, and substituted amino;
X is an amine or a thiol group;
P is a protecting group;
$X^1$ is selected from O, NR', CR'$_2$ and S, wherein each R' is independently selected from H, alkyl, substituted alkyl, alkenyl, substituted alkenyl, aryl, substituted aryl;
n is an integer from 1 to 4; and
m is an integer from 1 to 14.

In some embodiments the method further involves preparing an organic ligand of formula (I) from the compound of formula (IX):

$(R^1)_n$—[phenyl ring with L-Y]—O—$(\ )_m$—XP (IXa)

→

$(R^1)_n$—[phenyl ring with L-Y]—O—$(\ )_m$—X (Ia)

wherein:
L is selected from phenyl, substituted phenyl, biphenyl and substituted biphenyl;
Y is selected from H, halogen, hydroxyl, azido, phenyl, substituted phenyl, biphenyl, substituted biphenyl, alkoxy, substituted alkoxy, alkyl, substituted alkyl, amino, substituted amino, cycloalkyl, substituted cycloalkyl, heterocycloalkyl, and substituted heterocycloalkyl;
$R^1$ are each independently selected from H, halogen, hydroxyl, azido, alkyl, substituted alkyl, alkenyl, substituted alkenyl, alkynyl, substituted alkynyl, alkoxy, substituted alkoxy, amino, and substituted amino;
X is an amine or a thiol group;
P is a protecting group;
n is an integer from 1 to 4; and
m is an integer from 1 to 14.

In some embodiments the protecting group P is a labile protecting group that is easily removed under mild reaction conditions. In some embodiments, P is an acid labile protecting group (e.g. a Boc group) and a compound of formula (I) is prepared by the deprotection reaction of a compound of formula (IX) with an acidic reagent (e.g., trifluoroacetic acid (TFA)). In other embodiments, P is a base labile protecting group (e.g. a thioacetate group) and a compound and a compound of formula (I) is prepared by the deprotection of a compound of formula (IX) with a basic reagent (e.g., aqueous sodium hydroxide (NaOH)).

In some embodiments the methods described herein, further include one or more purification steps. Any method of purification can be utilized in the disclosed methods, including, but not limited to, flash column chromatography, high performance liquid chromatography (HPLC), recrystallization, and distillation.

It is understood that based on the present disclosure, variations of the synthetic strategy, the protecting groups, the reagents and reaction conditions depicted in the figures and exemplary examples are possible.

Any convenient protection and deprotection steps can be included in the subject methods to temporarily protect a functional group of interest, such as a hydroxyl group, an amine group, or a thiol group.

Nanocapsules

Aspects of the present disclosure include nanocapsule structures composed of organic ligand-functionalized nanoparticles, wherein the organic ligand has a structure as described herein. By "nanoparticles" is meant particles that have a size range in the nanometer (nm) scale. For example, a nanoparticle may have a size (e.g., largest dimension) of 1000 nm or less, such as a size ranging from 0.1 nm to 1000 nm. Nanocapsules of the present disclosure include structures having a shell that extends in three dimensions, such as length, width and height. Three-dimensional structures are distinct from one-dimensional structures (e.g., linear structures) and two-dimensional structures (e.g., planar structures).

In certain embodiments, nanocapsules of the present disclosure are referred to as structures having a shell configuration. The terms "nanocapsules", "capsule", "capsule configuration", "shell" or "shell configuration" are used interchangeably herein to describe structures where a surface at least partially, and sometimes completely, encloses a space or material. A shell may partially or completely enclose the space or material. For instance, a shell may partially enclose the space or material, such as enclose 50% or more of the space or material, or 60% or more, or 70% or more, or 80% or more, or 90% or more, or 95% or more, or 97% or more, or 99% or more of the space or material. Partial enclosure of a space or material includes embodiments where the surface is substantially contiguous and has one or more voids (e.g., holes) in the surface, and also includes embodiments where the surface is substantially continuous, but the surface does not extend to completely enclose the space or material. In other embodiments, the shell completely encloses the space or material, such that the surface is substantially continuous without significant discontinuities (e.g., voids or holes) in the surface.

Surfaces with a shell configuration may have various shapes and sizes. For instance, shell configurations include, but are not limited to, regular shapes such as spherical shells, ellipsoid shells, cylinder shells, cone shells, cube shells, cuboid shells, pyramidal shells, torus shells, and the like. In other embodiments, the shell may have an irregular shape. In certain embodiments, structures of the present disclosure have a shell configuration, where the shell configuration is a spherical surface (i.e., a spherical shell). In certain embodiments, the nanocapsules of the present disclosure are microstructures. By "microstructure" or "microshell" or "microshell configuration" is meant the structure has a size range in the micrometer (μm) scale. For example, a microstructure may have a size (e.g., largest dimension) of 1000 μm or less, such as a size ranging from 10 nm to 1000 μm.

In certain embodiments, the structures are microstructures as described above, where the microstructures have a size of 1000 μm or less, such as 950 μm or less, or 900 μm or less, or 850 μm or less, or 800 μm or less, or 750 μm or less, or 700 μm or less, or 650 μm or less, or 600 μm or less, or 550 μm or less, or 500 μm or less, or 450 μm or less, or 400 μm or less, or 350 μm or less, or 300 μm or less, or 250 μm or less, or 200 μm or less, or 150 μm or less, or 100 μm or less, or 90 μm or less, or 80 μm or less, or 70 μm or less, or 60 μm or less, or 50 μm or less, or 40 μm or less, or 30 μm or less, or 20 μm or less, or 10 μm or less, or 9 μm or less, or 8 μm or less, or 7 μm or less, or 6 μm or less, or 5 μm or less, or 4 μm or less, or 3 μm or less, or 2 μm or less, or 1 μm or less, or 0.75 μm or less, or 0.5 μm or less, or 0.25 μm or less, or 0.1 μm or less, or 0.075 μm or less, or 0.05 μm or less, or 0.025 μm or less, or 0.01 μm or less. In some instances, the microstructures have a size ranging from 0.01 μm to 1000 μm, 0.025 μm to 1000 μm, 0.05 μm to 1000 μm, 0.075 μm to 1000 μm, 0.1 μm to 1000 μm, such as from 0.25 μm to 1000 μm, or 0.5 μm to 1000 μm, or 0.5 μm to 900 μm, or 0.5 μm to 800 μm, or 0.5 μm to 700 μm, or 0.5 μm to 600 μm, or 0.5 μm to 500 μm, or 0.5 μm to 400 μm, or 0.5 μm to 300 μm, or 0.5 μm to 250 μm, or 0.5 μm to 200 μm, or 0.5 μm to 150 μm, or 0.5 μm to 100 μm, or 0.5 μm to 90 μm, or 0.5 μm to 80 μm, or 0.5 μm to 70 μm, or 0.5 μm to 60 μm, or 0.5 μm to 50 μm, or 0.5 μm to 40 μm, or 0.5 μm to 30 μm, or 0.5 μm to 20 μm, or 0.5 μm to 10 μm, or 0.5 μm to 9 μm, or 0.5 μm to 8 μm, or 0.5 μm to 7 μm, or 0.5 μm to 6 μm, or 0.5 μm to 5 μm, or 0.5 μm to 4 μm, or 0.5 μm to 3 μm, or 0.5 μm to 2 μm, or 0.5 μm to 1 μm. The size of the microstructures may be measured as the largest dimension of the microstructure (e.g., length, width, or height), or for spherical microstructures (e.g., spherical surfaces), may be measured as the average diameter of the microstructures. By "average" is meant the arithmetic mean. In certain instances, the microstructures have an average size of 5 μm. In certain instances, the microstructures have an average size of 1 μm. In certain instances, the microstructures have an average size of 0.1 μm. In certain instances, the microstructures have an average size of 0.05 μm. Mixtures of different sizes and/or shapes of nanocapsule structures (e.g., nanocapsule microstructures) may be used as desired. In other embodiments, the nanocapsule microstructures have substantially the same size and shape.

Nanocapsules of the present disclosure are composed of nanoparticles. For example, in a shell configuration, the shell may be composed of the nanoparticles. In certain embodiments, the nanoparticles are stably associated with each other to form the shell. By "stably associated" is meant that a moiety is bound to or otherwise associated with another moiety or structure under standard conditions. In certain instances, the nanoparticles may be stably associated with each other such that the shell substantially maintains its shape after formation of the shell. In some embodiments, the nanoparticles are stably associated with each other through non-covalent interactions, such as, but not limited to, ionic bonds, hydrophobic interactions, hydrogen bonds, van der Waals forces (e.g., London dispersion forces), dipole-dipole interactions, and the like. In some embodiments, the nanoparticles are stably associated with each other through covalent bonds. For example, a nanoparticle may be covalently bound or cross-linked to one or more nanoparticles in the shell. In certain cases, the nanoparticles are stably associated with each other through a combination of non-covalent and covalent interactions.

As described above, the nanocapsules of the present disclosure may be composed of nanoparticles. The nanoparticles may have a size of 1000 nm or less, such as 900 nm or less, or 800 nm or less, or 700 nm or less, or 600 nm or less, or 500 nm or less, or 400 nm or less, or 300 nm or less, or 250 nm or less, or 200 nm or less, or 150 nm or less, or 100 nm or less, or 90 nm or less, or 80 nm or less, or 70 nm or less, or 60 nm or less, or 50 nm or less, or 40 nm or less, or 30 nm or less, or 20 nm or less, or 10 nm or less, or 9 nm or less, or 8 nm or less, or 7 nm or less, or 6 nm or less, or 5 nm or less, or 4 nm or less, or 3 nm or less, or 2 nm or less, or 1 nm or less. In some instances, the nanoparticles have a size ranging from 0.1 nm to 1000 nm, such as from 0.5 nm to 1000 nm, or 1 nm to 1000 nm, or 1 nm to 900 nm, or 1 nm to 800 nm, or 1 nm to 700 nm, or 1 nm to 600 nm, or 1 nm to 500 nm, or 1 nm to 400 nm, or 1 nm to 300 nm, or 1 nm to 250 nm, or 1 nm to 200 nm, or 1 nm to 150 nm, or 1 nm to 100 nm, or 1 nm to 90 nm, or 1 nm to 80 nm, or 1 nm to 70 nm, or 1 nm to 60 nm, or 1 nm to 50 nm, or 1 nm to 40 nm, or 1 nm to 30 nm, or 1 nm to 20 nm, or 1 nm to 10 nm, or 1 nm to 9 nm, or 1 nm to 8 nm, or 1 nm to 7 nm, or 1 nm to 6 nm, or 1 nm to 5 nm. The size of the nanoparticles may be measured as the largest dimension of the nanoparticle (e.g., length, width, etc.), or for spherical nanoparticles, may be measured as the average diameter of the nanoparticles. By "average" is meant the arithmetic mean. In certain instances, the nanoparticles have an average size of 5 nm. In certain instances, the nanoparticles have an average size of 6 nm. Mixtures of different sizes and/or shapes of nanoparticles may be included in the nanocapsules as desired. In other embodiments, the nanoparticles have substantially the same size and shape.

Nanoparticles may have various shapes, such as, but not limited to, spherical, ellipsoid, cylinder, cone, cube, cuboid, pyramidal, needle, and the like. The nanoparticles may be made of any convenient material, such as, but not limited to, a semiconductor material, a metal, a metal oxide, a metalloid, a metal coated material, an oxide, a magnetic material, a nanosome, a dielectric material, a polymer, combinations thereof, and the like. For example, nanoparticles may be composed of materials, such as, but not limited to, titanium dioxide, silicon, gold, gold-plated silica, polymers, polymer-coated nanoparticles, quantum dot materials (as described in more detail below), and the like.

In certain embodiments, the nanoparticles that form the nanocapsules are arranged as a mixture of nanoparticles to form the nanocapsule. For instance, the nanocapsule may be composed of a mixture (e.g., a substantially homogeneous mixture) of nanoparticles. In some embodiments, the nanoparticles are arranged in one or more layers to form the three-dimensional structure. The composition of each layer of the nanocapsule structure may be the same or may be different. For example, each layer of the nanocapsule structure may be composed of the same type of nanoparticle or mixture of nanoparticles. Nanoparticles that are of the same type may include nanoparticles that are substantially the same with respect to their physical and chemical characteristics, such as, but not limited to, size, shape, composition, ligand attached to the surface of the nanoparticle, and the like. In other cases, a layer of the three-dimensional structure may have a different composition (e.g., a different nanoparticle or mixture of nanoparticles) than an adjacent layer. For instance, nanoparticles may differ with respect to one or more physical and/or chemical characteristics, such as, but not limited to, size, shape, composition, ligand attached to the surface of the nanoparticle, and the like.

In certain embodiments, the nanocapsule is composed of nanoparticles where the nanoparticles are a mixture of different types of nanoparticles. For instance, the mixture of nanoparticles may be a heterogeneous mixture of nanoparticles that is composed of different types of nanoparticles. The different types of nanoparticles may include nanoparticles that vary in one or more physical and/or chemical characteristics, such as, but not limited to, size, shape, composition, ligand attached to the surface of the nanoparticle, combinations thereof, and the like.

In certain embodiments, the nanoparticles are composed of a semiconductor material. For example, the nanoparticles may be quantum dots (QD). Quantum dots are nanoparticles made of a semiconductor material that exhibits quantum mechanical properties. In some instances, the nanoparticles may be composed of a material, such as, but not limited to, lead sulfide, lead selenide, cadmium selenide, cadmium sulfide, indium arsenide, indium phosphide, cadmium selenide sulfide, zinc sulfide, combinations thereof, and the like. In certain embodiments, the nanoparticles are composed of cadmium selenide (CdSe), zinc sulfide, or combinations thereof.

In certain embodiments, the nanoparticle is composed of a material or mixture of materials, such that the composition of the nanoparticle is substantially homogeneous. In some cases, the nanoparticle is composed of two or more materials. Nanoparticles composed of two or more materials include nanoparticles composed of a mixture of the two or more materials, such that the nanoparticles have a substantially homogeneous composition, and nanoparticles where the nanoparticles are composed of regions of a material interspersed with or adjacent to regions of one or more different materials. For instance, a nanoparticle may be composed of a core of a first material (or mixture of materials) substantially surrounded by a shell of a different material (or different mixture of materials). The shell of the different material may be disposed as one or more layers of material on a surface of the core of the first material.

In some embodiments, the nanoparticles may be quantum dots as described above. The quantum dots may be composed of two or more semiconductor materials, such as, but not limited to, lead sulfide, lead selenide, cadmium selenide, cadmium sulfide, indium arsenide, indium phosphide, cadmium selenide sulfide, zinc sulfide, and the like. In certain embodiments, the nanoparticle includes a core of cadmium selenide (CdSe) substantially surrounded by a shell of zinc sulfide (ZnS) disposed on a surface of the core.

Nanoparticles of the present disclosure are organic ligand-functionalized nanoparticles. An organic ligand-functionalized nanoparticle is a nanoparticle that includes an organic ligand attached to the surface of the nanoparticle. The organic ligand may be attached to the surface of the nanoparticle through non-covalent interactions, such as, but not limited to, ionic bonds, hydrophobic interactions, hydrogen bonds, van der Waals forces (e.g., London dispersion forces), dipole-dipole interactions, and the like, or through covalent bonds. In certain embodiments, the ligand is attached to the surface of the nanoparticle through a covalent bond. In some instances, the organic ligands exhibit π-π interactions between the aromatic groups of the ligands attached to the surface of the nanoparticle.

The organic ligand suitable for functionalization of the nanoparticles may vary depending on the desired properties of the functionalized nanoparticle. For example, the organic ligand on the ligand-functionalized nanoparticle may be selected such that the spacing between adjacent organic ligand-functionalized nanoparticles is a desired spacing. Stated another way, in some instances, the spacing between adjacent ligand-functionalized nanoparticles may depend on one or more properties of the ligand, such as, but not limited to, the size, structure, and/or orientation of the ligand. In some cases, the spacing between adjacent nanoparticles is 5 nm or more, such as 6 nm or more, or 7 nm or more, or 8 nm or more, or 9 nm or more, or 10 nm or more, or 11 nm or more, or 12 nm or more, or 13 nm or more, or 14 nm or more, or 15 nm or more, or 16 nm or more, or 17 nm or more, or 18 nm or more, or 19 nm or more, or 20 nm or more. In some cases, the spacing between adjacent nanoparticles is 10 nm or more. In some cases, the spacing between adjacent nanoparticles is 5 nm to 20 nm, such as 7 nm to 15 nm, or 10 nm to 15 nm. In some instances, the spacing between adjacent nanoparticles is 10 nm to 15 nm, such as 10 nm to 13 nm, or 10 nm to 12 nm. In certain embodiments, the spacing between adjacent nanoparticles is selected so as to minimize shifts in the emission spectrum of the nanoparticles. In certain embodiments, the spacing between adjacent nanoparticles is selected so as to minimize energy losses due to fluorescence resonance energy transfer (FRET).

In certain embodiments, the organic ligand is a mesogenic ligand (also referred to as a liquid crystal ligand), and as such the functionalized nanoparticles are mesogenic ligand-functionalized nanoparticles. In some instances, the organic ligand is a promesogenic organic ligand bearing a motif including multiple closely linked aromatic rings—likened to a molecular 'rod' (calamitic)—and an orthogonal nucleophilic tethering arm. In some instances, a mesogenic ligand or promesogenic ligand has liquid crystalline properties. For instance, a mesogenic ligand or promesogenic ligand may include a rigid moiety (e.g., closely linked aromatic rings) and one or more flexible moieties (e.g., amine or thiol tether). The rigid and flexible moieties of the mesogenic/promesogenic ligands may facilitate alignment of the mesogenic/promesogenic ligands in a common direction. For example, as described herein, mesogenic/promesogenic ligand-functionalized nanoparticles may be dispersed in a liquid crystalline liquid, and thus the flexible moiety may facilitate alignment of the mesogenic/promesogenic ligand with the surrounding liquid crystalline liquid. For instance, organic ligands attached to a surface of a nanoparticle may align with the director of a surrounding liquid crystalline liquid (e.g., a nematic phase of the liquid crystalline liquid).

In certain embodiments, the subject organic ligand has a phase transition temperature (also referred to as a melting temperature or clearing point) ranging from 50° C. to 150° C., such as 75° C. to 125° C., or 80° C. to 120° C., or 85° C. to 115° C., or 90° C. to 110° C. In certain embodiments, the organic ligand has a phase transition temperature (e.g., melting temperature or clearing point) of 100° C. For example, the phase transition temperature may be a temperature at which the organic ligand transitions from a first phase to a second phase (or vice versa). In some embodiments, the organic ligand may transition from a phase having positional order (e.g., an ordered spatial arrangement of the ligands, such as in an ordered lattice) or directional order (e.g., alignment of the ligands along a common directional axis) to a phase having substantially no positional or directional order. In some embodiments, the organic ligand may transition from a phase having substantially no positional or directional order to a phase having positional or directional order. In some cases, the organic ligand has positional and/or directional order below the phase transition temperature, and substantially no positional or directional order above the phase transition temperature. Similarly, the subject organic ligands that are stably associated with or attached to a surface of organic ligand-functionalized nanoparticles may have a phase transition from a phase having substantially no positional or directional order to a phase having positional or directional order (or vice versa). As described above, organic ligands that are stably associated with or attached to a surface of organic ligand-functionalized nanoparticles may have a phase transition temperature (also referred to as a melting temperature or clearing point) ranging from 50° C. to 150° C., such as 75° C. to 125° C., or 80° C. to 120° C., or 85° C. to 115° C., or 90° C. to 110° C. In certain embodiments, organic ligands that are stably associated with or attached to a surface of organic ligand-functionalized nanoparticles may have a phase transition temperature (e.g., melting temperature or clearing point) of 100° C.

In certain embodiments the subject organic ligands are stable at temperatures greater than 100° C., such as greater than 200° C., or even greater. In some cases, mesogenic ligands are stable at temperatures greater than 300° C., such as greater than 350° C., greater than 400° C., greater than 450° C., greater than 500° C., or even greater. In some embodiments, the subject organic ligands are stable at temperatures up to and including 350° C.

In other embodiments, ligands suitable for functionalization of the nanoparticles are non-mesogenic ligands. In some embodiments, the nanoparticles are additionally functionalized with ligands which are different in structure to the subject organic ligands, which may simply be referred to herein as "other ligands". For instance, the other ligand may be an organic compound. Examples of other ligands that may be attached to a surface of the nanoparticle include, but are not limited to, octadecylamine (ODA), octadecanethiol (ODT), octadecylphosphonic acid, oleic acid, combinations thereof, and the like. In some instances, the nanoparticles are functionalized with a mixture of the subject organic ligands and other ligands. In certain instances, the ratio of the subject organic ligands to other ligands on the nanoparticle surface is 9:1. In some embodiments, the ratio of the subject organic ligands to other ligands on the nanoparticle surface is 9:1 or less, such as 8:1, or 7:1, or 6:1, or 5:1, or 4:1, or 3:1, or 2:1 or 1:1. In some embodiments, the ratio of the subject organic ligands to other ligands on the nanoparticle surface is 6:4. In some embodiments, the ratio of the subject organic ligands to other ligands on the nanoparticle surface is 6:4 or less, such as 5:4, or even less. In certain embodiments, there are less subject organic ligands than other ligands on the nanoparticle surface.

In certain embodiments, the subject organic ligand includes a cross-linkable functional group. The cross-linkable functional group may be a group that, when activated, can form an attachment to another moiety. In some cases, the attachment may attach an organic ligand to another organic ligand (e.g., an organic ligand of an adjacent organic ligand-functionalized nanoparticle), may attach an organic ligand to a nanoparticle, may attach an organic ligand to a ligand (e.g., an organic ligand) of a ligand-functionalized nanoparticle (e.g., a nanoparticle functionalized with "other ligands"), may attach a ligand (e.g., other ligands) to an organic ligand (e.g., an organic ligand of an adjacent organic ligand-functionalized nanoparticle), or may attach a ligand (e.g., other ligands) to another ligand (e.g., a ligand of an adjacent ligand-functionalized nanoparticle). In certain embodiments, the cross-linkable functional group forms a covalent bond attachment the other moiety. In certain embodiments, the cross-linkable functional group is a light activated cross-linkable functional group. A light activated cross-linkable functional group is a cross-linkable functional group that may form an attachment to another moiety when light is applied to the light activated cross-linkable functional group. For example, exposure of the light activated cross-linkable functional group to light may activate the functional group, thus forming a reactive moiety capable of forming a crosslink to another moiety as described above. In some instances, the applied light is ultraviolet (UV) light. In some instances, the applied light is visible light. In some instances, the applied light is infrared light. For example, the applied light may be UV light having a wavelength ranging from 100 nm to 400 nm, such as 150 nm to 400 nm, or 200 nm to 400 nm, or 300 nm to 400 nm. In some instances, the applied UV light may be approximately 350 nm, such as 360 nm or 364 nm. Other types of cross-linkable functional groups may also be used, such as chemically activated cross-linkable functional groups, and the like.

Any convenient cross-linkable functional group may be used. In certain embodiments, the cross-linkable functional group is a functional group that, when activated, forms a reactive moiety. The reactive moiety may then react with another moiety (e.g., subject organic ligand, other ligand nanoparticle, etc.) to form an attachment (e.g., covalent bond) between the cross-linkable functional group and the other moiety. In some cases, the reactive moiety is a moiety capable of forming a covalent bond to carbon. For example, the reactive moiety may be a nitrene, such as a reactive nitrene derived from an azide functional group (e.g., an azide cross-linkable functional group). A nitrene may form a covalent bond to carbon to produce an amine or amide. In some instances, the cross-linkable functional group includes an azide, such as, but not limited to, a tetrafluoro-arylazide group.

As described above, the subject nanocapsules may be composed of nanoparticles having substantially the same physical and chemical characteristics, or in other embodiments, may be composed of nanoparticles having different physical and/or chemical characteristics. For example, physical and/or chemical characteristics of the nanoparticles that may be the same or may vary as described above may include, but are not limited to, size, shape, composition, ligand attached to the surface of the nanoparticle, organic ligand attached to the surface of the nanoparticle, cross-linkable functional group, combinations thereof, and the like. For instance, a nanoparticle may include a plurality of organic ligands attached to the surface of the nanoparticle, where the organic ligands are substantially the same. In other instances, the nanoparticle may include a plurality of organic ligands attached to the surface of the nanoparticle, where the organic ligands are different (e.g., ligands having different chemical structures and/or functional groups, such as cross-linkable functional groups as described herein). For example, combinations of various organic ligands may be attached to the surface of the same nanoparticle. In some instances, the ligands attached to the surface of the nanoparticle do not include any cross-linkable groups. In some instances, the ligands exhibit π-π interactions between the aromatic groups of the ligands attached to the surface of the nanoparticle.

Compositions

As described above, nanocapsules of the present disclosure may have a shell configuration that partially or completely encloses a space or material. In certain embodiments, the shell encloses a material, such as a dye. Encapsulation of a dye inside the three-dimensional structure may facilitate one or more of: application of the dye to a surface of a substrate; tuning (e.g., changing, such as dynamically changing) the emission spectrum of the dye; and the like.

Nanocapsules of the present disclosure may also enclose other types of material, such as, but not limited to, a liquid crystal, a dye, an ink, combinations thereof, and the like. The liquid crystal enclosed by the nanocapsule may be a liquid crystal (e.g., a liquid crystal liquid) as described in more detail herein. For instance, the enclosed liquid crystal liquid may be a liquid crystal having a certain phase, such as, but not limited to, a liquid crystal in an isotropic phase, a liquid crystal in a nematic phase, a liquid crystal in a cholesteric phase, and the like. A liquid crystal in a cholesteric phase may also be referred to a liquid crystal in a chiral nematic phase. Liquid crystals in a cholesteric (chiral nematic) phase exhibit a twisting of the liquid crystal molecules perpendicular to the director, with the molecular axis of the liquid crystals parallel to the director.

Aspects of the present disclosure include compositions that include the nanocapsules as disclosed herein. The composition may include the subject nanocapsule and a liquid. In some instances, the composition includes the nanocapsule dispersed in the liquid. In some instances, the liquid is a liquid crystalline fluid (e.g., a liquid crystalline liquid), such as a liquid crystalline liquid as described in more detail below. In some instances, the liquid is a solvent. Any convenient solvent may be used, depending on the desired composition of three-dimensional structures. Examples of solvents include, but are not limited to, organic solvents, such as toluene, dimethylbenzene, methylisopropylbenzene, methanol, ethyl acetate, chloroform, mixtures thereof, and the like. In some instances, the solvent is toluene.

Aspects of the present disclosure also include compositions for producing a subject nanocapsule of organic ligand-functionalized nanoparticles described herein. In certain embodiments, the composition includes nanoparticles and a liquid crystalline fluid (e.g., a liquid crystalline liquid). The nanoparticles in the composition for producing the nanocapsule may be any of the nanoparticles as described herein. For instance, the nanoparticles may be organic ligand-functionalized nanoparticles, such as organic ligand-functionalized nanoparticles as described herein.

In certain cases, the composition includes a liquid crystalline fluid (e.g., a liquid crystalline liquid). The liquid crystalline fluid may be composed of a liquid crystal. In certain cases, the liquid crystal has a phase transition, such as a phase transition between an isotropic phase and a nematic phase (or vice versa). By "isotropic phase" or "isotropic" is meant a liquid crystal phase where the liquid crystals have no significant positional order or directional order. By "nematic phase" or "nematic" is meant a liquid crystal phase where the liquid crystals have no significant positional order, but have a detectable directional order. In some instances, the liquid crystal phase transition occurs in response to a stimulus applied to the liquid crystals. The stimulus may be any convenient stimulus that can induce a phase transition in the liquid crystals, such as, but not limited to, a change in temperature, an electrical stimulus, a magnetic stimulus, combinations thereof, and the like. In some cases, the stimulus that induces the phase transition in the liquid crystal is a change in temperature, e.g., heating or cooling. As such, the liquid crystalline fluid may be composed of a liquid crystal that has a temperature dependent phase transition. In some embodiments, the liquid crystalline fluid undergoes a phase transition from an isotropic phase to a nematic phase when the temperature of the liquid crystalline fluid is reduced to below the phase transition temperature. In some embodiments, the liquid crystalline fluid undergoes a phase transition from a nematic phase to an isotropic phase when the temperature of the liquid crystalline fluid is increased to above the phase transition temperature.

In certain embodiments, a temperature dependent liquid crystalline fluid has a phase transition temperature that is lower than the phase transition temperature of an organic ligand (or an organic ligand-functionalized nanoparticle) as described herein. As such, in some instances, the phase transition temperature (e.g., melting temperature or clearing point) of the organic ligand (or organic ligand-functionalized nanoparticle) is greater than the phase transition temperature of the liquid crystalline fluid. In certain instances, a temperature dependent liquid crystalline fluid has a phase transition temperature (e.g., for a phase transition between an isotropic phase and a nematic phase) ranging from 20° C. to 50° C., such as 25° C. to 45° C., or 30° C. to 40° C. In some cases, a temperature dependent liquid crystalline fluid has a phase transition temperature (e.g., for a phase transition between an isotropic phase and a nematic phase) of approximately 35° C., such as 34° C. or 33° C. Examples of liquid crystalline fluids that have a temperature dependent phase transition include, but are not limited to, 4-cyano-4'-pentylbiphenyl (5CB), and the like.

Methods

Aspects of the present disclosure include methods of producing a nanocapsule of organic ligand-functionalized nanoparticles described herein. The method of producing the subject nanocapsules includes dispersing the nanoparticles in a liquid crystalline fluid (e.g., a liquid crystalline liquid). The nanoparticles used in the methods for producing the three-dimensional structures may be any of the nanoparticles as described herein. For instance, the nanoparticles may be ligand-functionalized nanoparticles, such as organic ligand-functionalized nanoparticles as described herein.

The nanoparticles may be dispersed in the liquid crystalline fluid using any convenient method, such as, but not limited to, mixing, vortexing, shaking, applying sound energy (also referred to as "sonication" herein), combinations thereof, and the like. In some cases, the method includes applying sound energy to the nanoparticles in the liquid crystalline fluid to disperse the nanoparticles in the liquid crystalline fluid. The nanoparticles may be dispersed in the liquid crystalline fluid such that the nanoparticles are substantially evenly distributed throughout the liquid crystalline fluid. For example, a mixture of the nanoparticles and liquid crystalline liquid may be substantially homogeneous. In certain embodiments, the nanoparticles are dispersed in the liquid crystalline fluid at room temperature (e.g., ~25° C.). In other cases, the nanoparticles are dispersed in the liquid crystalline fluid at a temperature other than room temperature, e.g., lower or higher than room temperature. In some instances, the nanoparticles are dispersed in the liquid crystalline fluid at a temperature higher than room temperature. In certain embodiments, the nanoparticles are dispersed in the liquid crystalline fluid at a temperature where the nanoparticles are present in a desired phase of the liquid crystalline fluid, such as an isotropic phase. For instance, embodiments of the methods include dispersing the nanoparticles in the liquid crystalline fluid at a temperature where the nanoparticles are present in an isotropic phase of the liquid crystalline fluid. In certain aspects, the temperature where the nanoparticles are present in an isotropic phase of the liquid crystalline fluid is a temperature above the phase transition temperature of the liquid crystalline fluid, such as a temperature ranging from 20° C. to 50° C., such as 25° C. to 45° C., or 30° C. to 40° C., such as a temperature of approximately 35° C., for example 34° C.

Embodiments of the method of producing the nanocapsules described herein also include inducing a phase transition from an isotopic phase to a nematic phase in the liquid crystalline fluid (e.g., the liquid crystalline liquid) to produce the nanocapsule. Thus, the method may include inducing a phase transition from an isotropic phase to a nematic phase in the liquid crystalline liquid.

In some instances, inducing a phase transition in the liquid crystalline liquid is performed by applying a stimulus to the liquid crystalline liquid. The stimulus may be any convenient stimulus that can induce a phase transition in the liquid crystals, such as, but not limited to, a change in temperature, an electrical stimulus, a magnetic stimulus, combinations thereof, and the like. In some cases, inducing the phase transition in the liquid crystalline liquid is accomplished by changing the temperature of the liquid crystalline liquid, e.g., heating or cooling the liquid crystalline liquid. In certain instances, inducing the phase transition in the liquid crystalline liquid is accomplished by decreasing the temperature of the liquid crystalline liquid to a temperature below the phase transition temperature of the liquid crystalline liquid. Reducing the temperature of the liquid crystalline liquid to a temperature below the phase transition temperature of the liquid crystalline liquid may induce a phase transition of the liquid crystalline liquid from an isotropic phase to a nematic phase. In some cases, at the isotropic to nematic phase transition in a homogeneous liquid crystalline liquid, domains of nematic ordering form and grow as the liquid crystalline liquid is cooled through the transition temperature. As the nematic domains form and increase in size, isotropic domains began decreasing in size. In some instances, the dispersed nanoparticles (e.g., organic ligand-functionalized nanoparticles) in the liquid crystalline liquid may preferentially locate in the shrinking isotropic domains. As the nanoparticles aggregate at the interface between the isotropic and nematic domains, the nanoparticles may form a nanocapsule of stably associated nanoparticles, e.g., as described herein. For example, a three-dimensional structure having a shell configuration may be produced, such as a shell configuration having a spherical surface.

As described above, in certain embodiments, the functionalized nanoparticles may include an organic ligand having a cross-linkable functional group. As such, embodiments of the method may further include crosslinking the organic ligand-functionalized nanoparticles in the nanocapsule structure. For instance, after the formation of the nanocapsule, the cross-linkable functional group may be activated by applying an appropriate stimulus to the cross-linkable functional group of the nanoparticle. In certain embodiments, the cross-linkable functional group is a light activated cross-linkable functional group. As such, certain embodiments of the methods include applying light to the light activated cross-linkable functional group sufficient to activate cross-linking of the light activated cross-linkable functional group. Where the light activated cross-linkable functional group is activated by UV light, the method includes applying ultraviolet (UV) light. For example, the method may include applying UV light having a wavelength ranging from 100 nm to 400 nm, such as 150 nm to 400 nm, or 200 nm to 400 nm, or 300 nm to 400 nm. In some instances, the method includes applying UV light having a wavelength of approximately 350 nm, or 360 nm or 364 nm. In other embodiments, the stimulus applied to the cross-linkable functional group may include visible light, infrared light, a chemical stimulus, combinations thereof, etc.

Aspects of the method of producing the nanocapsules may further include separating the produced nanocapsules from the liquid crystalline fluid (e.g., liquid crystalline liquid) used to produce the nanocapsules. Any convenient separation method may be used to separate the three-dimensional structures from the liquid crystalline liquid. For example, the separation method may include filtering, centrifuging, chromatography, extraction, and the like. In some instances, separating the nanocapsules includes adding the produced nanocapsules to a solvent. The solvent used may be added in a large excess volume as compared to the volume of liquid crystalline liquid used to produce the nanocapsules to substantially disperse the liquid crystalline liquid. Examples of solvents include, but are not limited to, organic solvents, such as toluene, dimethylbenzene, methylisopropylbenzene, methanol, ethyl acetate, chloroform, mixtures thereof, and the like. In some instances, the solvent is toluene.

Utility

The subject organic ligands find use in a variety of material applications, particularly in the formation of novel templatable mesoscale nanocapsules. The subject organic ligands can both enhance and tune particle dispersion in a liquid crystal phase to create novel liquid crystal nanocapsules. The subject nanocapsules, compositions and methods find use in a variety of different applications where nanocapsule microstructures, such as three-dimensional nanocapsule microstructures having a shell configuration (e.g., microshells), are desired. For example, the nanocapsules, compositions and methods find use in photovoltaics, photonic materials, and the liquid crystal laser such as, but not limited to, light emitting devices that are components of video displays, lights, etc. In these embodiments, the nanocapsules may be provided on a surface of a substrate. For instance, the nanocapsules may be disposed on a surface of the substrate, such as arranged as a layer of three-dimensional microstructures on a surface of the substrate. The substrate may be any desired type of substrate that is suitable for use in a light emitting device, such as, but not limited to, a substrate for an integrated circuit or a substrate for a microelectricalmechanical system (MEMS) device, etc. (e.g., a silicon substrate).

In certain embodiments, the light emitting device is a component of a light, such as a light emitting diode (LED). As described above, the nanocapsules include nanoparticles, such as quantum dots, and as such, the light emitting device may be a component of a quantum dot LED (QD-LED). In some cases, using the nanocapsules disclosed herein in an LED may facilitate an increase in the possible color spectrum of the LED. For instance, the emission spectrum of the LED may depend on the size of the nanocapsule microstructures, and as such, the emission color of the LED may be tuned depending on the size of the nanocapsule microstructures. In some embodiments, the nanocapsule microstructures may be used as a coating on a surface of a conventional LED (e.g., a QD coating). Light emitted from the conventional LED may photo-excite the QD coating, thus causing the nanocapsules in the QD coating to emit light of a different wavelength.

In other embodiments, the nanocapsules may emit light via direct electrical excitation. For example, an electric field may be applied to the nanocapsules (e.g., QD microstructures), thus causing emission of light from the nanocapsules.

In some instances, the light emitting device is a component of a video display. As described above, the nanocapsules include nanoparticles, such as quantum dots, and as such, the light emitting device may be a component of a quantum dot video display. In some cases, the quantum dot video display may include the nanocapsules of the present disclosure as a filter for conventional LEDs. For example, as described above, light emitted from a conventional LED may photo-excite the QD-containing nanocapsule, thus causing the nanocapsule to emit light of a different wavelength. In other embodiments, the quantum dot video display may include the nanocapsules of the present disclosure, where the nanocapsules emit light via direct electrical excitation, as described above. In certain embodiments, quantum dot-containing nanocapsules are characterized by pure and saturated emission colors with narrow bandwidth, and thus may facilitate production of a QD video display that has high color purity and efficiency, as compared to conventional LED or OLED video displays.

As described above, in certain instances, the spacing between adjacent nanoparticles is selected so as to minimize shifts in the emission spectrum of the nanoparticles. As such, the nanocapsules of the present disclosure find use in facilitating the production of light emitting devices that have pure and saturated emission colors with narrow bandwidth as described above. In addition, in certain instances, the spacing between adjacent nanoparticles is selected so as to minimize energy losses due to fluorescence resonance energy transfer (FRET). As such, the three-dimensional structures of the present disclosure find use in facilitating the production of light emitting devices that are more efficient as compared to conventional light emitting devices.

Nanocapsules of the present disclosure also find use in applications such as the encapsulation of a dye. Encapsulation of a dye inside the nanocapsule structure may facilitate one or more of: application of the dye to a surface of a substrate; tuning (e.g., changing, such as dynamically changing) the emission spectrum of the dye; and the like. For example, encapsulation of a dye in a nanocapsule structure of the present disclosure may be used to produce a light activated dye, such as a laser light activated dye. Exposure of the light activated dye to a light source (e.g., a laser) may photo-excite the nanocapsule (e.g., QD-containing three-dimensional microstructures), thus causing the nanocapsule to emit light.

Nanocapsules, compositions and methods of the present disclosure also find use in applications such as optical imaging. For instance, nanocapsule microstructures find use as probes for optical imaging, contrast agents, or as detectable labels for labeling biological tissues. In some instances, the nanocapsules, compositions and methods of the present disclosure find use in optical imaging applications where dynamic control of the optical properties of the three-dimensional microstructures is desired, such as by applying a physical, electrical, magnetic, etc. stimulus to the nanocapsules to alter the optical properties of the organic ligands.

Notwithstanding the appended claims, the disclosure set forth herein is also described by the following clauses.

Clause 1. An organic ligand of formula (I):

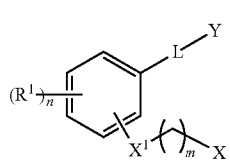

(I)

wherein:

L is selected from phenyl, substituted phenyl, biphenyl and substituted biphenyl;

Y is selected from H, halogen, hydroxyl, azido, phenyl, substituted phenyl, biphenyl, substituted biphenyl, alkoxy, substituted alkoxy, alkyl, substituted alkyl, amino, substituted amino, cycloalkyl, substituted cycloalkyl, heterocycloalkyl, and substituted heterocycloalkyl;

$R^1$ are each independently selected from H, halogen, hydroxyl, azido, alkyl, substituted alkyl, alkenyl, substituted alkenyl, alkynyl, substituted alkynyl, alkoxy, substituted alkoxy, amino, and substituted amino;

X is an amine or a thiol group;

$X^1$ is selected from O, NR', CR'$_2$ and S, wherein each R' is independently selected from H, alkyl, substituted alkyl, alkenyl, substituted alkenyl, aryl, substituted aryl;

n is an integer from 1 to 4; and m is an integer from 1 to 14.

Clause 2. The organic ligand of Clause 1, wherein L is:

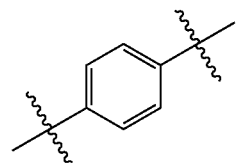 [SMILES: *c1ccc(*)cc1]

Clause 3. The organic ligand of Clause 1 or Clause 2, wherein Y is selected from:

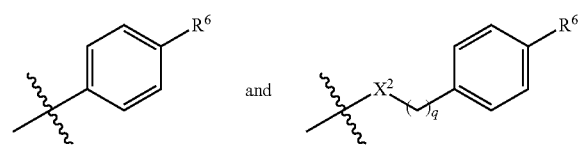

wherein, $R^6$ is selected from H, halogen, hydroxyl, azido, alkyl, substituted alkyl, alkenyl, substituted alkenyl, alkynyl, substituted alkynyl, alkoxy, substituted alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol;

$X^2$ is selected from O, NR', CR'$_2$ and S, wherein each R' is independently selected from H, alkyl, substituted alkyl, alkenyl, substituted alkenyl, aryl, substituted aryl; and q is an integer from 1 to 14.

Clause 4. The organic ligand of any one of Clauses 1-3, wherein $R^1$ and $R^6$ are each $C_1$-$C_{12}$ alkoxy and n is 1.

Clause 5. The organic ligand of any one of Clauses 1-4, of the formula (II):

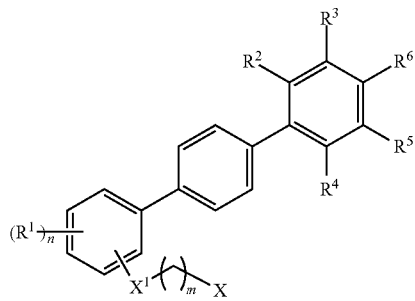

(II)

wherein:

R¹ are each independently selected H, halogen, hydroxyl, azido, alkyl, substituted alkyl, alkenyl, substituted alkenyl, alkynyl, substituted alkynyl, alkoxy, substituted alkoxy, amino, and substituted amino;

R², R³, R⁴, R⁵, and R⁶ are each independently selected from H, halogen, hydroxyl, azido, alkyl, substituted alkyl, alkenyl, substituted alkenyl, alkynyl, substituted alkynyl, alkoxy, substituted alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol;

X is an amine or a thiol group;

X¹ is selected from O, NR', CR'₂ and S, wherein each R' is independently selected from H, alkyl, substituted alkyl, alkenyl, substituted alkenyl, aryl, substituted aryl;

n is an integer from 1 to 4; and m is an integer from 1 to 14.

Clause 6. The organic ligand of Clause 5, of the formula (III):

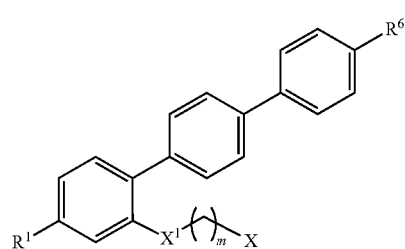

(III)

wherein:

R¹ is selected from halogen, hydroxyl, azido, alkyl, substituted alkyl, alkenyl, substituted alkenyl, alkynyl, substituted alkynyl, alkoxy, substituted alkoxy, amino, and substituted amino;

R⁶ is selected from H, halogen, hydroxyl, azido, alkyl, substituted alkyl, alkenyl, substituted alkenyl, alkynyl, substituted alkynyl, alkoxy, substituted alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol;

X is an amine or a thiol group;

X¹ is selected from O, NR', CR'₂ and S, wherein each R' is independently selected from H, alkyl, substituted alkyl, alkenyl, substituted alkenyl, aryl, substituted aryl; and m is an integer from 1 to 14.

Clause 7. The organic ligand of any one of Clauses 1-4, of the formula (IV):

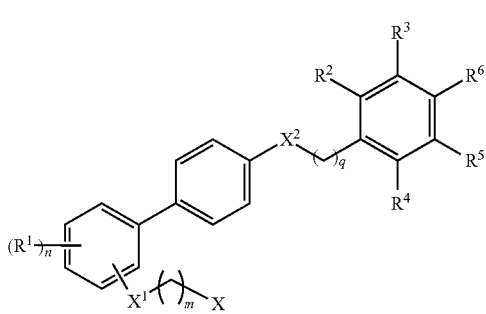

(IV)

wherein:

R¹ are each independently selected from H, halogen, hydroxyl, azido, alkyl, substituted alkyl, alkenyl, substituted alkenyl, alkynyl, substituted alkynyl, alkoxy, substituted alkoxy, amino, and substituted amino;

R², R³, R⁴, R⁵, and R⁶ are each independently selected from H, halogen, hydroxyl, azido, alkyl, substituted alkyl, alkenyl, substituted alkenyl, alkynyl, substituted alkynyl, alkoxy, substituted alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol;

X is an amine or a thiol group;

X¹ is selected from O, NR', CR'₂ and S, wherein each R' is independently selected from H, alkyl, substituted alkyl, alkenyl, substituted alkenyl, aryl, substituted aryl;

X² is selected from O, NR', CR'₂ and S, wherein each R' is independently selected from H, alkyl, substituted alkyl, alkenyl, substituted alkenyl, aryl, substituted aryl;

n is an integer from 1 to 4; and m and q are each independently an integer from 1 to 14.

Clause 8. The organic ligand of Clause 7, of the formula (V):

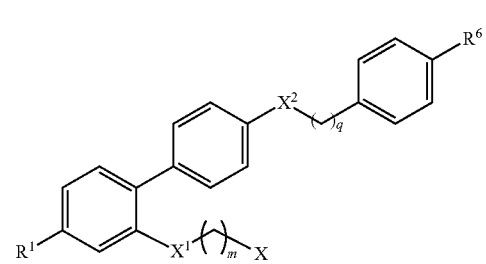

(V)

wherein:

R¹ is selected from halogen, hydroxyl, azido, alkyl, substituted alkyl, alkenyl, substituted alkenyl, alkynyl, substituted alkynyl, alkoxy, substituted alkoxy, amino, and substituted amino;

R⁶ is selected from H, halogen, hydroxyl, azido, alkyl, substituted alkyl, alkenyl, substituted alkenyl, alkynyl, substituted alkynyl, alkoxy, substituted alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol;

X is an amine or a thiol group;

$X^1$ is selected from O, NR', $CR'_2$ and S, wherein each R' is independently selected from H, alkyl, substituted alkyl, alkenyl, substituted alkenyl, aryl, substituted aryl;

$X^2$ is selected from O, NR', $CR'_2$ and S, wherein each R' is independently selected from H, alkyl, substituted alkyl, alkenyl, substituted alkenyl, aryl, substituted aryl; and m and q are each independently an integer from 1 to 14.

Clause 9. The organic ligand of any one of Clauses 5-8, wherein $R^1$ is $C_1$-$C_{12}$ alkoxy.

Clause 10. The organic ligand of any one of Clauses 5-9, wherein $R^6$ is $C_1$-$C_{12}$ alkoxy.

Clause 11. The organic ligand of any one of Clauses 1-10, wherein X is an amine group.

Clause 12. The organic ligand of any one of Clauses 1-10, wherein X is a thiol group.

Clause 13. The organic ligand of any one of Clauses 1-10, selected from the group:

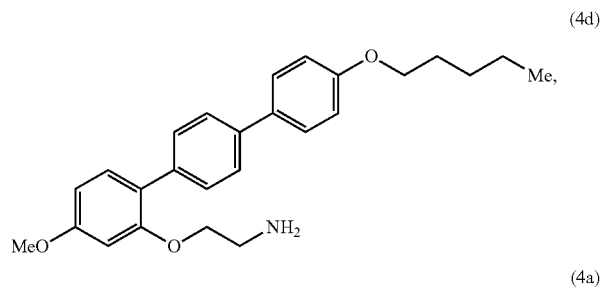
(4d)

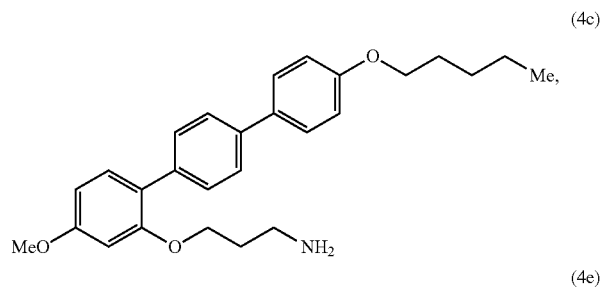
(4c)

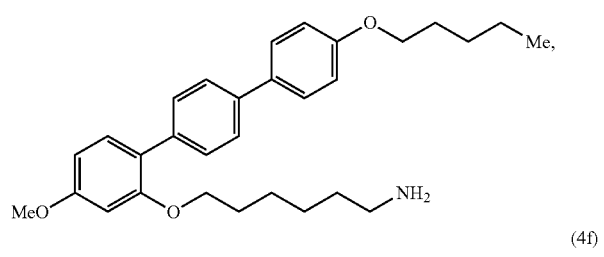
(4a)

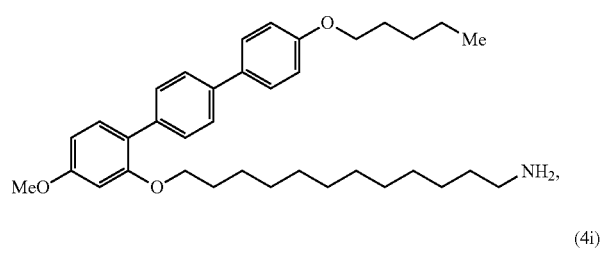
(4e)

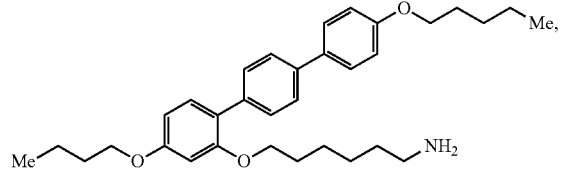
(4f)

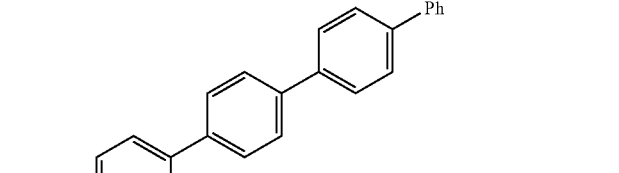
(4i)

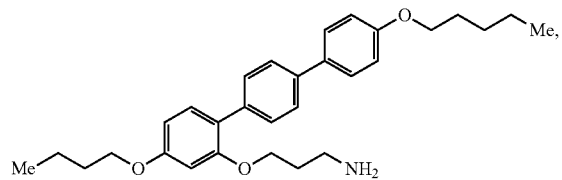
(4g)

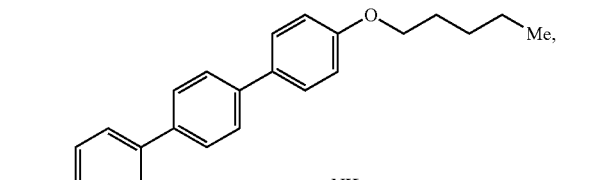
(4b)

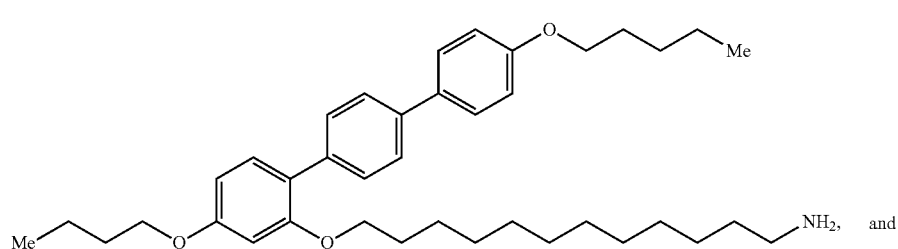
(4h)

and (4j) [Structure: MeO-substituted biphenyl with one ring bearing O-CH2-(4-methoxyphenyl) and the other bearing O-(CH2)6-NH2]

Clause 14. The organic ligand of any one of Clauses 1-6, of the structure (5):

(5) [Structure: biphenyl with MeO substituent, one ring bearing O-butyl-Me chain extended, and O-(CH2)n-SH chain]

Clause 15. A method of preparing an organic ligand according to any one of Clauses 1-14, the method comprising:

preparing a compound of formula (VII) from a compound of formula (VI):

(VI) $(R^1)_n$—aryl with $X^1$ and Z substituents

M—L—Y →

(VII) $(R^1)_n$—aryl with $X^1$ and L—Y substituent wherein:

Z is a leaving group,

M is selected from a substituted metalloid or a substituted metal;

L is selected from phenyl, substituted phenyl, biphenyl and substituted biphenyl;

Y is selected from H, halogen, hydroxyl, azido, phenyl, substituted phenyl, biphenyl, substituted biphenyl, alkoxy, substituted alkoxy, alkyl, substituted alkyl, amino, substituted amino, cycloalkyl, substituted cycloalkyl, heterocycloalkyl, and substituted heterocycloalkyl;

$R^1$ are each independently selected from H, halogen, hydroxyl, azido, alkyl, substituted alkyl, alkenyl, substituted alkenyl, alkynyl, substituted alkynyl, alkoxy, substituted alkoxy, amino, and substituted amino;

$X^1$ is selected from O, NR', CR'$_2$ and S, wherein each R' is independently selected from H, alkyl, substituted alkyl, alkenyl, substituted alkenyl, aryl, substituted aryl; and n is an integer from 1 to 4.

Clause 16. The method of Clause 15, wherein the compound of formula (VII) is prepared via a Suzuki coupling between a compound of formula (VI) and a derivative of formula (VIII):

(VI) $(R^1)_n$—aryl with $X^1$ and Z substituents (VIII) $R^7$—B($R^7$)—L—Y

→

(VII) $(R^1)_n$—aryl with $X^1$ and L—Y substituent wherein:

Z is a leaving group;

L is selected from phenyl, substituted phenyl, biphenyl and substituted biphenyl;

Y is selected from H, halogen, hydroxyl, azido, phenyl, substituted phenyl, biphenyl, substituted biphenyl, alkoxy, substituted alkoxy, alkyl, substituted alkyl, amino, substituted amino, cycloalkyl, substituted cycloalkyl, heterocycloalkyl, and substituted heterocycloalkyl;

$R^1$ are each independently selected from H, halogen, hydroxyl, azido, alkyl, substituted alkyl, alkenyl, substituted alkenyl, alkynyl, substituted alkynyl, alkoxy, substituted alkoxy, amino, and substituted amino;

$R^7$ are each independently selected from hydroxyl, alkyl, substituted alkyl, heteroalkyl and substituted heteroalkyl;

or both $R^7$ groups together with the boron to which they are attached form a group selected from heterocycle, substituted heterocycle, cycloalkyl and substituted cycloalkyl;

$X^1$ is selected from O, NR', CR'$_2$ and S, wherein each R' is independently selected from H, alkyl, substituted alkyl, alkenyl, substituted alkenyl, aryl, substituted aryl; and n is an integer from 1 to 4.

Clause 17. The method of clauses 15 or 16, further comprising preparing an organic ligand of formula (IX) from the compound of formula (VII):

(VII) → (IX)

wherein:
L is selected from phenyl, substituted phenyl, biphenyl and substituted biphenyl;
Y is selected from H, halogen, hydroxyl, azido, phenyl, substituted phenyl, biphenyl, substituted biphenyl, alkoxy, substituted alkoxy, alkyl, substituted alkyl, amino, substituted amino, cycloalkyl, substituted cycloalkyl, heterocycloalkyl, and substituted heterocycloalkyl;
$R^1$ are each independently selected from H, halogen, hydroxyl, azido, alkyl, substituted alkyl, alkenyl, substituted alkenyl, alkynyl, substituted alkynyl, alkoxy, substituted alkoxy, amino, and substituted amino;
X is an amine or a thiol group;
P is a protecting group;
$X^1$ is selected from O, NR', $CR'_2$ and S, wherein each R' is independently selected from H, alkyl, substituted alkyl, alkenyl, substituted alkenyl, aryl, substituted aryl;
n is an integer from 1 to 4; and
m is an integer from 1 to 14.

Clause 18. The method of clause 17, further comprising preparing an organic ligand of formula (I) from the compound of formula (IX):

(IX) → (I)

wherein:
L is selected from phenyl, substituted phenyl, biphenyl and substituted biphenyl;
Y is selected from H, halogen, hydroxyl, azido, phenyl, substituted phenyl, biphenyl, substituted biphenyl, alkoxy, substituted alkoxy, alkyl, substituted alkyl, amino, substituted amino, cycloalkyl, substituted cycloalkyl, heterocycloalkyl, and substituted heterocycloalkyl;
$R^1$ are each independently selected from H, halogen, hydroxyl, azido, alkyl, substituted alkyl, alkenyl, substituted alkenyl, alkynyl, substituted alkynyl, alkoxy, substituted alkoxy, amino, and substituted amino;
X is an amine or a thiol group;
P is a protecting group;
$X^1$ is selected from O, NR', $CR'_2$ and S, wherein each R' is independently selected from H, alkyl, substituted alkyl, alkenyl, substituted alkenyl, aryl, substituted aryl;
n is an integer from 1 to 4; and
m is an integer from 1 to 14.

Clause 19. The method of Clause 16, wherein the coupling is catalyzed by a palladium catalyst.

Clause 20. The method of Clause 16, wherein $R^7$ are both hydroxyl groups.

Clause 21. The method of Clause 15 or Clause 16, wherein the leaving group is a halogen.

Clause 22. The method of claim 15 or 16, wherein the leaving group is a tosylate.

Clause 23. A nanocapsule comprising organic ligand-functionalized nanoparticles, wherein the organic-ligand has a structure according to any one of Clauses 1-14.

Clause 24. The nanocapsule of Clause 23, wherein the nanocapsule has a spherical surface.

Clause 25. The nanocapsule of Clause 23, wherein the structure has a dimension of 0.01 µm to 10 µm.

Clause 26. The nanocapsule of Clause 24, wherein the spherical surface has an average diameter of 0.01 µm to 10 µm.

Clause 27. The nanocapsule of any of Clauses 23-26, wherein the nanoparticles have an average diameter of 1 nm to 100 nm.

Clause 28. The nanocapsule of any one of Clauses 23-27, wherein the nanoparticles are composed of a material selected from a semiconductor material, a metal, a metal oxide, a metalloid, a metal coated material, an oxide, a magnetic material, a nanosome, a dielectric material and a polymer, or combinations thereof.

Clause 29. The nanocapsule of Clause 28, wherein the nanoparticles are composed of cadmium selenide (CdSe), zinc sulfide (ZnS), gold, or combinations thereof.

Clause 30. The nanocapsule of any one of Clauses 23-29, wherein the structure is composed of nanoparticles having substantially the same physical and chemical characteristics.

Clause 31. The nanocapsule of any one of Clauses 23-29, wherein the structure is composed of nanoparticles having different physical and/or chemical characteristics.

Clause 32. A composition comprising:
a liquid; and
a nanocapsule of any of Clauses 23-31 in the liquid.

Clause 33. The composition of Clause 32, wherein the liquid is an organic solvent.

Clause 34. A composition for producing a nanocapsule, the composition comprising:
organic ligand-functionalized nanoparticles, wherein the organic ligand has a structure of any one of Clauses 1-14; and
a liquid crystalline liquid.

Clause 35. The composition of Clause 34, wherein an organic ligand of the organic ligand-functionalized nanoparticles has a phase transition temperature greater than the phase transition temperature of the liquid crystalline liquid.

Clause 36. A method of producing a nanocapsule, the method comprising:
dispersing organic ligand-functionalized nanoparticles in a liquid crystalline liquid, wherein the organic ligand has a structure of any one of Clauses 1-14; and
inducing a phase transition from an isotopic phase to a nematic phase in the liquid crystalline liquid to produce nanocapsules of stably associated organic ligand-functionalized nanoparticles.

Clause 37. The method of Clause 36, wherein the dispersing comprises applying sound energy to the organic ligand-functionalized nanoparticles in the liquid crystalline liquid.

Clause 38. The method of Clauses 36 or 37, wherein the inducing comprises reducing the temperature of the liquid crystalline liquid.

Clause 39. The method of any one of Clauses 36 to 38, further comprising crosslinking the organic ligand-functionalized nanoparticles in the nanocapsule.

Clause 40. The method of Clause 39, wherein the organic ligand-functionalized nanoparticles comprise a light activated cross-linkable functional group, and the crosslinking comprises applying light to the nanoparticles sufficient to activate the light activated cross-linkable functional group and produce one or more crosslinks between the nanoparticles.

Clause 41. A material comprising a nanocapsule of stably associated organic ligand-functionalized nanoparticles produced by the method of any one of Clauses 36-40.

EXAMPLES

General Considerations. Reactants, reagents, and solvents were used as received from commercial suppliers unless otherwise noted. A Mettler Toledo XS105 balance (repeatable to 0.1 mg with minimum 2.0 mg load) was used to measure mass. Flash column chromatography was performed using 40-63 µm 60 Å silica. Thin layer chromatography (TLC) was performed using Silicycle glass-backed extra hard layer indicating plates with 60 Å pore size and thickness of 250 µm, which were stored in a desiccator when not in use. Melting points were obtained on an electrothermal melting point apparatus and are uncorrected. NMR spectra were obtained on Agilent spectrometers. $^1$H NMR spectra were obtained at 400 and 500 MHz and referenced to the residual CHCl$_3$ singlet at 7.26 ppm and residual CH$_2$Cl$_2$ singlet at 5.33 unless otherwise noted. The abbreviations s, d, t, q, p, dd, and m stand for the resonance multiplicities singlet, doublet, triplet, quartet, pentet, doublet of doublet, and multiplet, respectively. $^{13}$C NMR spectra were obtained at 100 MHz and 125 MHz and referenced to the center line of the CDCl$_3$ triplet at 77.2 ppm and CD$_2$Cl$_2$ pentet at 53.4 unless otherwise noted. Carbon atom degree of substitution was determined using $^1$H-$^{13}$C HSQC. ATR FT-IR analysis was performed on a Bruker Vertex 70 (DOD grant 68959-RT-REP). HRMS data were obtained on a Thermo Scientific Exactive Plus Orbitrap mass spectrometer using ESI (DOD grant 68959-RT-REP). Glassware for all reactions was oven-dried at 135° C. and cooled in a desiccator prior to use.

General Procedure—Organic Ligands with Amine Tether

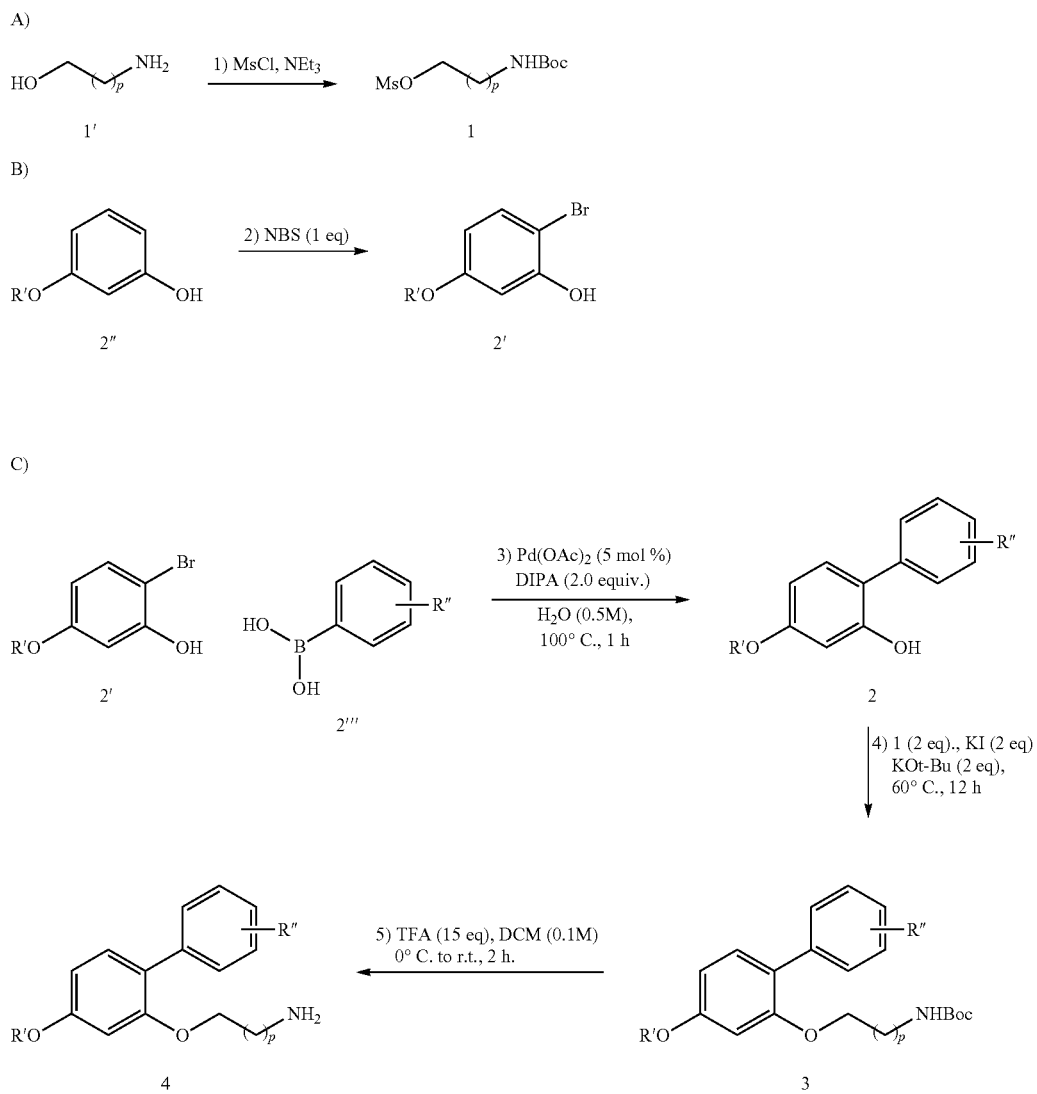

With reference to Scheme 1, R' is as defined herein for $R^1$, R" is as defined herein for Y and p is an integer from 1-13. In some cases, a compound of formula 1',2' and/or 2''' are commercially available.

Synthesis of Organic Ligands with Amine Tether

In some embodiments, the subject organic ligands were synthesized according to Scheme 1 by preparation of ligand core 2 via a Suzuki coupling between a bromide of formula 2' and a boronic acid of formula 2'''. The ortho-functionality was then added via coupling of the phenol 2 with N-Boc mesylate 1, which was synthesized by 0-mesylation of the corresponding alcohol of formula 1'. The N-Boc protecting group of a compound of formula 3 was then removed to yield the final ligands of general formula 4.

Example 1

I. General Experimental Procedure for the Synthesis of the Amine Linker (1)

Into a round bottom flask charged with a PTFE-coated magnetic stir bar were added 1.0 equivalent of alcohol in 0.2 M dry DCM and 1.3 equivalent of triethylamine. The reaction mixture was placed in an ice bath and 1.2 equivalent of methanesulfonyl chloride was added dropwise. After 18 hours, the reaction mixture was quenched with water and separated, and the organic layer was dried over anhydrous sodium sulfate and removed under reduced pressure to afford 1a-e.

12-((tert-butoxycarbonyl)amino)dodecyl methanesulfonate (1a)

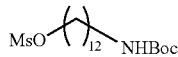

General procedure I was followed by using 1.7 g tert-butyl (12-hydroxydodecyl)carbamate (5.64 mmol), 1.02 mL of TEA (7.33 mmol), 0.52 mL of MsCl (6.77 mmol) and 28 mL of DCM. 1.99 g of 1a (93%) was obtained as a white solid, mp=54-55° C. $^1$H NMR (400 MHz, CDCl$_3$): δ 4.49 (br s, 1H), 4.22 (t, J=6.6 Hz, 2H), 3.10 (q, J=6.7 Hz, 2H), 3.00 (s, 3H), 1.73 (p, J=6.5 Hz, 2H), 1.44 (s, 9H), 1.42-1.21 (m, 18H); $^{13}$C NMR (100 MHz, CDCl$_3$): δ 156.0 (C), 79.0 (C), 70.2 (CH$_2$), 40.6 (CH$_2$), 37.4 (CH$_3$), 30.1 (CH$_2$), 29.5 (2CH$_2$), 29.4 (2CH$_2$), 29.3 (CH$_2$), 29.1 (CH$_2$), 29.0 (CH$_2$), 28.4 (3CH$_3$), 26.8 (CH$_2$), 25.4 (CH$_2$). ATR-FTIR (neat): 3374, 2918, 2852, 1687, 1523, 1361, 1169 cm$^{-1}$; HRMS (ESI) m/z calculated for C$_{18}$H$_{37}$NO$_5$S[M]$^+$: 380.2465, found: 380.2454.

6-((tert-butoxycarbonyl)amino)hexyl methanesulfonate (1b)

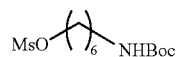

General procedure I was followed by using 1.0 g tert-butyl (6-hydroxyhexyl)carbamate (4.60 mmol), 0.83 mL of TEA (5.98 mmol), 0.43 mL of MsCl (5.52 mmol) and 23 mL of DCM. 1.20 g of 1b (88%) was obtained as an off-white solid, mp=44-45° C. $^1$H NMR (400 MHz, CDCl$_3$): δ 4.51 (s, 1H), 4.22 (t, J=6.5 Hz, 2H), 3.11 (q, J=6.8 Hz, 2H), 3.00 (s, 3H), 1.75 (p, J=6.5 Hz, 2H), 1.55-1.45 (m, 3H), 1.44 (s, 9H), 1.42-1.31 (m, 3H); $^{13}$C NMR (100 MHz, CDCl$_3$): δ 156.0 (C), 79.1 (C), 69.9 (CH$_2$), 40.4 (CH$_2$), 37.4 (CH$_3$), 29.9 (CH$_2$), 29.0 (CH$_2$), 28.4 (3CH$_3$), 26.2 (CH$_2$), 25.1 (CH$_2$). ATR-FTIR (neat): cm$^{-1}$; 3347, 2936, 2863, 1695, 1519, 1352, 1173; HRMS (ESI) m/z calculated for C$_{12}$H$_{25}$NO$_5$S [M]$^+$: 296.1526, found: 296.1517.

4-((tert-butoxycarbonyl)amino)butyl methanesulfonate (1c)

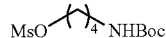

General procedure I was followed by using 1 g of tert-butyl (4-hydroxybutyl)carbamate (5.28 mmol), 0.96 mL of TEA (6.86 mmol), 0.49 mL of MsCl (6.34 mmol) and 26 mL of DCM. 1.21 g of 1c (86%) was obtained as a light yellow oil. $^1$H NMR (400 MHz, CDCl$_3$): δ 4.58 (br s, 1H), 4.24 (t, J=6.3 Hz, 2H), 3.20-3.11 (m, 2H), 3.00 (s, 3H), 1.78 (p, J=6.5 Hz, 2H), 1.60 (p, J=6.5 Hz, 2H), 1.43 (s, 9H); $^{13}$C NMR (100 MHz, CDCl$_3$): δ 156.0 (C), 79.3 (C), 69.6 (CH$_2$), 39.7 (CH$_2$), 37.4 (CH$_3$), 28.4 (3CH$_3$), 26.4 (CH$_2$), 26.3 (CH$_2$). ATR-FTIR (neat): 3380, 2975, 2938, 1694, 1522, 1344, 1173 cm$^{-1}$; HRMS (ESI) m/z calculated for C$_{10}$H$_{21}$NO$_5$S[M]$^+$: 268.1213, found: 268.1205.

3-((tert-butoxycarbonyl)amino)propyl methanesulfonate (1d)

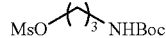

General procedure I was followed by using 1.0 g tert-butyl (3-hydroxypropyl)carbamate (5.71 mmol), 1.03 mL of TEA (7.42 mmol), 0.53 mL of MsCl (6.84 mmol) and 29 mL of DCM. 1.26 g of 1d (87%) was obtained as a light yellow oil. $^1$H NMR (400 MHz, CDCl$_3$): δ 4.67 (s, 1H), 4.29 (t, J=6.0 Hz, 2H), 3.26 (q, J=6.2 Hz, 2H), 3.03 (s, 3H), 1.94 (p, J=6.2 Hz, 2H), 1.44 (s, 9H). δ 156.0 (C), 79.6 (C), 67.4 (CH$_2$), 37.4 (CH$_3$), 36.7 (CH$_2$), 28.4 (3CH$_3$), 27.4 (CH$_2$). This product is also commercially available. The spectral data matched those reported by Sarafiano and coworkers (Sarafianos, S. G.; et al. J. Biol. Chem. 2003, 278, 16280).

2-((tert-butoxycarbonyl)amino)ethyl methanesulfonate (1e)

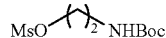

General procedure I was followed by using 2 g of tert-butyl (2-hydroxyethyl)carbamate (12.4 mmol), 2.24 mL of TEA (16.1 mmol), 1.15 mL of MsCl (14.9 mmol) and 62 mL of DCM. 2.41 g 1e (81%) was obtained as a viscous yellow oil. $^1$H NMR (400 MHz, CDCl$_3$): δ 4.98 (s, 1H), 4.26 (t, J=5.2 Hz, 2H), 3.45 (q, J=5.4 Hz, 2H), 3.02 (s, 3H), 1.42 (s, 9H). This compound is not stable and was used immediately.

The spectral data matched those reported by Borbas and coworkers (Borbas, K. E.; Bruce, J. I. *Org. Biomol. Chem.* 2007, 5, 2274).

Example 2

II. General Experimental Procedure for the Synthesis of Rod-Like Ligand Backbone Via Suzuki Cross-Coupling (2)

Into a 20 mL vial charged with a PTFE-coated magnetic stir bar were added 1.0 equivalent of arylbromide, 1.5 equivalent of arylboronic acid and 0.05 equivalent of palladium (II) acetate. The vial was sealed with septa and placed under vacuum and then it was filled with nitrogen. To this vial was added 0.5 M degassed water and 2.0 equivalent of degassed disopropylamine. The reaction mixture was stirred for an hour at 100° C. The mixture was extracted with Ethyl acetate and passed through a pad of celite. The residue was then dried over anhydrous sodium sulfate and removed under reduced pressure. Purification by flash column chromatography (100:0→80:20 hexanes:EtOAc) on $SiO_2$ afforded 2a-d as a solid.

4-methoxy-4''-(pentyloxy)-[1,1':4',1''-terphenyl]-2-ol (2a)

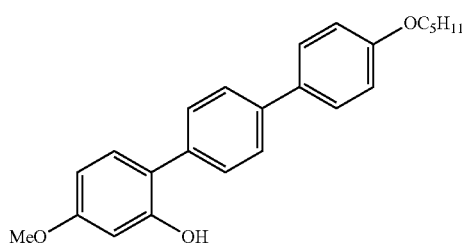

General procedure II was followed by using 0.50 g of 2-bromo-5methoxyphenol (2.46 mmol), 1.05 g of (4'-(pentyloxy)-[1,1'-biphenyl]-4-yl)boronic acid (3.69 mmol), 28 mg of palladium (II) acetate (0.12 mmol), 4.9 mL water and 0.69 mL disopropylamine (4.92 mmol). Purification by flash column chromatography (100:0→80:20 hexanes:EtOAc) on $SiO_2$ afforded 2a (0.398 g, 45%) as a beige solid, mp=168-169° C. $^1H$ NMR (500 MHz, $CDCl_3$): δ 7.67 (d, J=8.6 Hz, 2H), 7.57 (d, J=8.6 Hz, 2H), 7.49 (d, J=8.6 Hz, 2H), 7.21 (d, J=8.4 Hz, 1H), 7.00 (d, J=8.6 Hz, 2H), 6.63-6.58 (m, 2H), 5.30 (s, 1H), 4.02 (t, J=6.6 Hz, 2H), 3.85 (s, 3H), 1.83 (pen, J=6.8 Hz, 2H), 1.49-1.38 (m, 4H), 0.96 (t, J=7.2 Hz, 3H); $^{13}C$ NMR (125 MHz, $CDCl_3$): δ 163.2 (C), 161.6 (C), 156.1 (C), 142.7 (C), 137.8 (C), 135.4 (C), 133.4 (CH), 132.0 (2CH), 130.7 (2CH), 130.2 (2CH), 123.2 (C), 117.5 (2CH), 109.7 (CH), 104.0 (CH), 70.7 ($OCH_2$), 58.1 ($OCH_3$), 31.7 ($CH_2$), 30.9 ($CH_2$), 25.2 (2$CH_2$), 16.7 ($CH_3$); ATR-FTIR (neat): 3392, 2932, 2859, 1615, 1495, 1288, 1127 $cm^{-1}$; HRMS (ESI) m/z calculated for $C_{24}H_{26}O_3[M]^+$: 363.1955, found: 363.1956.

2-bromo-5-butoxyphenol 2b'

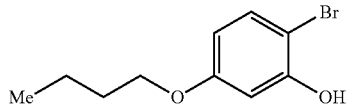

Into a 250 mL volumetric flask charged with a PTFE-coated magnetic stir bar were added 1 g of 3 butoxyphenol (6.0 mmol) in 150 mL dry DCM. Reaction flask was placed in ice bath and 1.01 g of N-bromosuccinimide (6.0 mmol) was added to the reaction mixture slowly in four portions over a period of two hours. Then the reaction was brought to room temperature and stirred for another hour. Purification by flash column chromatography (100:0→85:15 hexanes:EtOAc) on $SiO_2$ afforded 2-bromo-5-butoxyphenol 2b' (1.2 g, 82%) as a white solid, mp=32-33° C. $^1H$ NMR (400 MHz, $CDCl_3$): δ 7.30 (d, J=8.9 Hz, 1H), 6.59 (d, J=2.8 Hz, 1H), 6.40 (dd, J=8.9, 2.9 Hz, 1H), 5.49 (s, 1H), 3.91 (t, J=6.5 Hz, 2H), 1.75 (pen, J=7.9 Hz, 2H), 1.47 (sex, J=7.6 Hz, 2H), 0.97 (t, J=7.4 Hz, 3H); $^{13}C$ NMR (100 MHz, $CDCl_3$): δ 160.1 (C), 152.9 (C), 131.9 (CH), 109.9 (CH), 102.2 (CH), 100.6 (C), 68.0 ($OCH_2$), 31.1 ($CH_2$), 19.2 ($CH_2$), 13.8 ($CH_3$); ATR-FTIR (neat): 3507, 2958, 2873, 1588, 1488, 1175 $cm^{-1}$; HRMS (ESI) m/z calculated for $C_{10}H_{13}BrO_2$ $[M]^+$: 245.1172, found: 245.1172.

4-butoxy-4''-(pentyloxy)-[1,1':4',1''-terphenyl]-2-ol (2b)

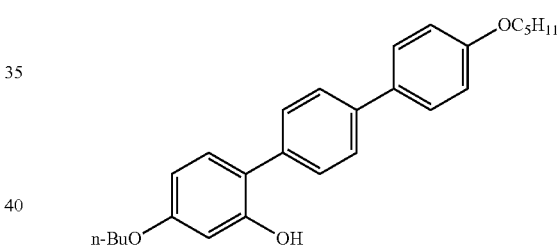

General procedure II was followed by using 0.50 g of 2-bromo-5-butoxyphenol (2.04 mmol), 0.87 g of (4'-(pentyloxy)-[1,1'-biphenyl]-4-yl)boronic acid (3.06 mmol), 23 mg of palladium (II) acetate (0.12 mmol), 4.1 mL water and 0.58 mL disopropylamine (4.08 mmol). Purification by flash column chromatography (100:0→80:20 hexanes:EtOAc) on $SiO_2$ afforded 2b (0.386 g, 47%) as a white solid, mp=114-115° C. $^1H$ NMR (400 MHz, $CDCl_3$): δ 7.65 (d, J=8.6 Hz, 2H), 7.55 (d, J=8.6 Hz, 2H), 7.48 (d, J=8.6 Hz, 2H), 7.18 (d, J=8.4 Hz, 1H), 6.99 (d, J=8.6 Hz, 2H), 6.61-6.53 (m, 2H), 5.30 (s, 1H), 4.01 (t, J=6.6 Hz, 2H), 3.99 (t, J=6.6 Hz, 2H), 1.87-1.72 (m, 4H), 1.53-1.36 (m, 6H), 0.99 (t, J=7.5 Hz, 3H), 0.95 (t, J=7.2 Hz, 3H); $^{13}C$ NMR (100 MHz, $CDCl_3$): δ 160.1 (C), 158.9 (C), 153.4 (C), 140.0 (C), 135.2 (C), 132.8 (C), 130.7 (CH), 129.4 (2CH), 128.0 (2CH), 127.5 (2CH), 120.3 (C), 114.9 (2CH), 107.6 (CH), 101.8 (CH), 68.1 ($CH_2$), 67.8 ($CH_2$), 31.3 ($CH_2$), 29.0 ($CH_2$), 28.2 ($CH_2$), 22.5 ($CH_2$), 19.3 ($CH_2$), 14.0 ($CH_3$), 13.9 ($CH_3$); ATR-FTIR (neat): 3501, 2957, 2872, 1610, 1495, 1253, 1144 $cm^{-1}$; HRMS (ESI) m/z calculated for $C_{27}H_{32}O_3[M]^+$: 405.2424, found: 405.2412.

4-methoxy-[1,1':4',1":4",1'''-quaterphenyl]-2-ol (2c)

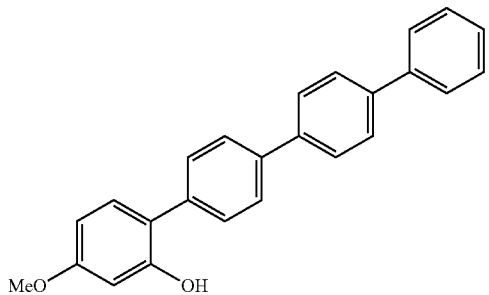 [SMILES: COc1ccc(-c2ccc(-c3ccc(-c4ccccc4)cc3)cc2)c(O)c1]

General procedure II was followed by using 0.50 g of 2-bromo-5methoxyphenol (2.46 mmol), 1.01 g of [1,1':4',1"-terphenyl]-4-ylboronic acid (3.69 mmol), 28 mg of palladium (II) acetate (0.12 mmol), 4.9 mL water and 0.69 mL disopropylamine (4.92 mmol). Purification by flash column chromatography (100:0→70:30 hexanes:EtOAc) on $SiO_2$ afforded 2c (0.112 g, 13%) as a beige solid, mp=226-227° C. $^1$H NMR (400 MHz, $CDCl_3$): δ 7.75 (d, J=8.2 Hz, 2H), 7.71 (d, J=1.1 Hz, 4H), 7.68-7.64 (m, 2H), 7.54 (d, J=8.2 Hz, 2H), 7.47 (t, J=6.4 Hz, 2H), 7.22 (d, J=8.1 Hz, 1H), 6.63-6.53 (m, 2H), 5.29 (s, 1H), 3.84 (t, J=6.6 Hz, 2H); $^{13}$C NMR (100 MHz, $CDCl_3$): δ 160.6 (C), 153.4 (C), 140.6 (C), 140.3 (C), 139.8 (C), 139.4 (C), 136.0 (C), 130.8 (2CH), 129.5 (2CH), 128.8 (2CH), 127.9 (2CH), 127.6 (2CH), 127.4 (3CH), 127.0 (2CH), 120.4 (C), 107.1 (CH), 101.4 (CH), 55.4 ($OCH_3$); ATR-FTIR (neat): 3265, 1613, 1523, 1368, 1281, 1164, 1131 $cm^{-1}$; HRMS (ESI) m/z calculated for $C_{25}H_{20}O_2$ $[M]^+$: 353.1536, found: 353.1531.

4-methoxy-4'-((4-methoxybenzyl)oxy)-[1,1'-biphenyl]-2-ol (2d)

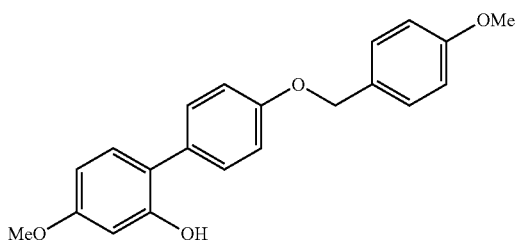 [SMILES: COc1ccc(COc2ccc(-c3ccc(OC)cc3O)cc2)cc1]

General procedure II was followed by using 0.50 g of 2-bromo-5methoxyphenol (2.46 mmol), 0.95 g of (4'-((4-methoxybenzyl)oxy)-[1,1'-biphenyl]-4-yl)boronic acid (3.69 mmol), 28 mg of palladium (II) acetate (0.12 mmol), 4.9 mL water and 0.69 mL disopropylamine (4.92 mmol). Purification by flash column chromatography (100:0→80:20 hexanes:EtOAc) on $SiO_2$ afforded 2d (0.182 g, 22%) as a white solid, mp=118-119° C. $^1$H NMR (400 MHz, $CDCl_3$): δ 7.38 (d, J=8.2 Hz, 2H), 7.34 (d, J=8.2 Hz, 2H), 7.11 (d, J=8.1 Hz, 2H), 7.07 (d, J=8.1 Hz, 2H), 6.94 (d, J=8.2 Hz, 2H), 6.57-6.52 (m, 2H), 5.23 (br s, 1H), 5.03 (s, 1H), 3.83 (t, J=6.3 Hz, 2H), 3.82 (s, 3H), 3.82 (s, 3H); $^{13}$C NMR (100 MHz, $CDCl_3$): δ 160.3 (C), 159.5 (C), 158.4 (C), 153.4 (C), 130.7 (C), 130.3 (CH), 130.2 (CH), 129.3 (CH), 129.2 (C), 129.2 (C), 128.8 (CH), 120.5 (CH), 115.7 (2CH), 114.1 (2CH), 101.2 (CH), 101.1 (CH), 69.9 ($OCH_2$), 55.4 ($OCH_3$), 55.3 ($OCH_3$); ATR-FTIR (neat): 3401, 2960, 2839, 1614, 1503, 11237, 1169 $cm^{-1}$; HRMS (ESI) m/z calculated for $C_{21}H_{20}O_4[M]^+$: 337.1434, found: 337.1423.

Example 3

III. General Experimental Procedure for the Synthesis of N-Boc Protected Mesogenic Organic Ligands (3)

Into a 20 mL vial charged with a PTFE-coated magnetic stir bar were added 1.0 equivalent of 2, 2.0 equivalent of 1, 2.0 equivalent of potassium iodide in 0.075 M dry THF. 2.0 equivalent of 1.7 M KOt-Bu in THF was added to the vial drop wise. The reaction mixture was stirred for 12 hours at 60° C. The solvent was removed under reduced pressure and the solid residue was extracted with water and DCM. The organic layer was collected and dried over anhydrous sodium sulfate and removed under reduced pressure. Purification by flash column chromatography (100:0→85:15 hexanes:ethyl acetate) on $SiO_2$ afforded 3a-j as a solid.

tert-butyl(12-((4-methoxy-4"-(pentyloxy)-[1,1':4',1"-terphenyl]-2-yl)oxy)dodecyl)carbamate (3a)

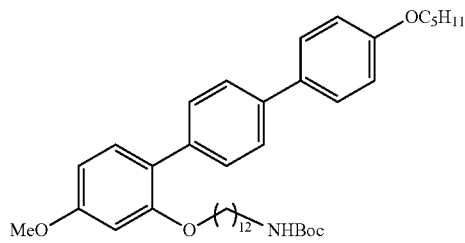

General procedure III was followed by using 100 mg of 2a (0.276 mmol), 209 mg 1a (0.552 mmol), 92 mg of KI (0.552 mmol), and 0.32 mL of KOt-Bu solution in 3.68 mL THF. Purification by flash column chromatography (100:0→85:15 hexanes:EtOAc) on $SiO_2$ afforded 3a (130 mg, 73%) as a white solid, mp: 80-81° C. $^1$H NMR (400 MHz, $CDCl_3$): δ 7.60-7.53 (m, 6H), 7.30 (d, J=8.3 Hz, 1H), 6.98 (d, J=8.6 Hz, 2H), 6.60-6.54 (m, 2H), 4.49 (br. s, 1H), 4.01 (t, J=6.6 Hz, 2H), 3.96 (t, J=6.5 Hz, 2H), 3.85 (s, 3H), 3.09 (q, J=6.7 Hz, 2H), 1.82 (pen, J=6.4 Hz, 2H), 1.75 (pen, J=6.2 Hz, 2H), 1.52-1.45 (m, 4H), 1.44 (s, 9H), 1.43-1.20 (m, 18H), 0.95 (t, J=7.1 Hz, 3H); $^{13}$C NMR (100 MHz, $CDCl_3$): δ 160.2 (C), 158.6 (C), 157.1 (C), 156.9 (C), 138.7 (C), 136.8 (C), 133.4 (C), 131.1 (CH), 129.7 (2CH), 128.0 (2CH), 126.1 (2CH), 123.3 (C), 114.7 (2CH), 104.7 (CH), 99.9 (CH), 79.0 (C), 68.4 ($CH_2$), 68.0 ($CH_2$), 55.4 ($OCH_3$), 40.6 ($CH_2$), 30.1 ($CH_2$), 29.5 (40$H_2$), 29.3 ($CH_2$), 29.2 ($CH_2$), 29.1 ($CH_2$), 29.0 ($CH_2$), 28.4 (3$CH_3$), 28.2 ($CH_2$), 26.8 ($CH_2$), 26.1 ($CH_2$), 22.5 ($CH_2$), 14.0 ($CH_3$); ATR-FTIR (neat): 3359, 2956, 2871, 1713, 1609, 1248, 1136 $cm^{-1}$; HRMS (ESI) m/z calculated for $C_{41}H_{59}NO_5[M]^+$: 646.4466, found: 646.4447.

tert-butyl(6-((4-methoxy-4''-(pentyloxy)-[1,1':4',1''-terphenyl]-2-yl)oxy)hexyl)carbamate (3b)

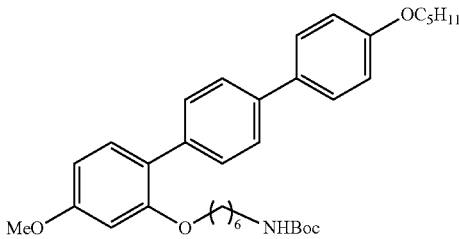

General procedure III was followed by using 210 mg of 2a (0.579 mmol), 342 mg 1b (1.16 mmol), 192 mg of KI (1.16 mmol), and 0.68 mL of KOt-Bu solution in 7.72 mL THF. Purification by flash column chromatography (100:0→85:15 hexanes:EtOAc) on $SiO_2$ afforded 3b (266 mg, 82%) as a white solid, mp=87-88° C. $^1$H NMR (400 MHz, $CDCl_3$): δ 7.61-7.55 (m, 6H), 7.30 (d, J=8.2 Hz, 1H), 6.98 (d, J=8.2 Hz, 2H), 6.61-6.53 (m, 2H), 4.46 (br. s, 1H), 4.01 (t, J=6.6 Hz, 2H), 3.96 (t, J=6.4 Hz, 2H), 3.85 (s, 3H), 3.07 (q, J=6.7 Hz, 2H), 1.83 (pen, J=6.6 Hz, 2H), 1.75 (pen, J=6.6 Hz, 2H), 1.52-1.45 (m, 5H), 1.44 (s, 9H), 1.38-1.24 (m, 3H), 0.96 (t, J=7.1 Hz, 3H); $^{13}$C NMR (100 MHz, $CDCl_3$): δ 160.2 (C), 158.6 (C), 157.0 (C), 156.0 (C), 138.7 (C), 136.8 (C), 133.3 (C), 131.1 (CH), 129.8 (2CH), 128.0 (2CH), 126.0 (2CH), 123.3 (C), 114.8 (2CH), 104.8 (CH), 100.0 (CH), 79.0 (C), 68.3 ($CH_2$), 68.1 ($CH_2$), 55.4 ($OCH_3$), 40.5 ($CH_2$), 30.0 ($CH_2$), 29.0 ($2CH_2$), 28.4 ($3CH_3$), 28.2 ($CH_2$), 26.4 ($CH_2$), 25.8 ($CH_2$), 22.5 ($CH_2$), 14.0 ($CH_3$); ATR-FTIR (neat): 3358, 2933, 2860, 1711, 1609, 1509, 1491, 1248, 1167 $cm^{-1}$; HRMS (ESI) m/z calculated for $C_{35}H_{45}NO_5$ [M]$^+$: 562.3527, found: 562.3522.

tert-butyl(4-((4-methoxy-4''-(pentyloxy)-[1,1':4',1''-terphenyl]-2-yl)oxy)butyl)carbamate (3c)

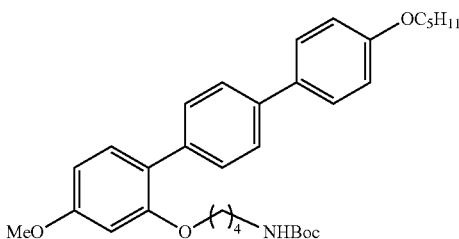

General procedure III was followed by using 150 mg of 2a (0.414 mmol), 221 mg 1c (0.828 mmol), 137 mg of KI (0.828 mmol), and 0.49 mL of KOt-Bu solution in 5.52 mL THF. Purification by flash column chromatography (100:0→85:15 hexanes:EtOAc) on $SiO_2$ afforded 3c (132 mg, 60%) as a white solid, mp=98-99° C. $^1$H NMR (400 MHz, $CDCl_3$): δ 7.61-7.51 (m, 6H), 7.29 (d, J=8.3 Hz, 1H), 6.98 (d, J=8.4 Hz, 2H), 6.58 (dd, J=8.4, 2.4 Hz, 1H), 6.55 (d, J=2.4 Hz, 1H), 4.46 (br. s, 1H), 4.01 (t, J=6.6 Hz, 2H), 3.98 (t, J=6.6 Hz, 2H), 3.85 (s, 3H), 3.11 (q, J=6.6 Hz, 2H), 1.89-1.71 (m, 4H), 1.59 (pen, J=7.2 Hz, 2H), 1.51-1.42 (m, 4H), 1.40 (s, 9H) 0.95 (t, J=7.1 Hz, 3H); $^{13}$C NMR (100 MHz, $CDCl_3$): δ 160.2 (C), 158.6 (C), 156.8 (C), 155.9 (C), 138.8 (C), 136.7 (C), 133.3 (C), 131.2 (CH), 129.8 (CH), 129.7 (CH), 128.1 (CH), 128.0 (CH), 126.2 (CH), 126.1 (CH), 123.4 (C), 114.7 (2CH), 105.0 (CH), 100.1 (CH), 79.1 (C), 68.1 (2$CH_2$), 55.5 ($OCH_3$), 40.1 ($CH_2$), 29.0 ($CH_2$), 28.4 (3$CH_3$), 28.2 ($CH_2$), 26.8 ($CH_2$), 26.4 ($CH_2$), 22.4 ($CH_2$), 14.0 ($CH_3$); ATR-FTIR (neat): 3308, 2932, 2869, 1673, 1609, 1249, 1172 $cm^{-1}$; HRMS (ESI) m/z calculated for $C_{33}H_{43}NO_5$ [M]$^+$: 534.3214, found: 534.3190.

tert-butyl(3-((4-methoxy-4''-(pentyloxy)-[1,1':4',1''-terphenyl]-2-yl)oxy)propyl)carbamate (3d)

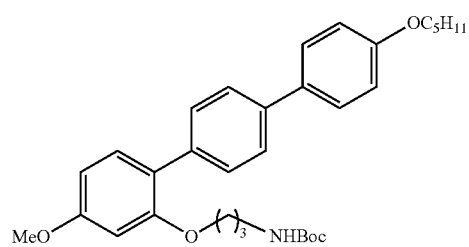

General procedure III was followed by using 150 mg of 2a (0.414 mmol), 210 mg 1d (0.828 mmol), 137 mg of KI (0.828 mmol), and 0.49 mL of KOt-Bu solution in 5.52 mL THF. Purification by flash column chromatography (100:0→85:15 hexanes:EtOAc) on $SiO_2$ afforded 3d (177 mg, 82%) as a white solid, mp=105-106° C. $^1$H NMR (400 MHz, $CDCl_3$): δ 7.61-7.51 (m, 6H), 7.29 (d, J=8.3 Hz, 1H), 6.98 (d, J=8.4 Hz, 2H), 6.62-6.55 (m, 2H), 4.59 (br. s, 1H), 4.01 (t, J=6.6 Hz, 4H), 3.85 (s, 3H), 3.24 (q, J=6.4 Hz, 2H), 1.93 (pen, J=6.3 Hz, 2H), 1.82 (pen, J=6.4 Hz, 2H), 1.51-1.40 (m, 4H), 1.39 (s, 9H) 0.95 (t, J=7.1 Hz, 3H); $^{13}$C NMR (100 MHz, $CDCl_3$): δ 160.2 (C), 158.6 (C), 156.7 (C), 155.9 (C), 138.9 (C), 136.8 (C), 133.2 (C), 131.2 (CH), 129.7 (2CH), 128.0 (2CH), 126.2 (2CH), 123.5 (C), 114.7 (2CH), 105.3 (CH), 100.2 (CH), 80.0 (C), 68.1 (2$CH_2$), 55.4 ($OCH_3$), 38.0 ($CH_2$), 29.0 ($CH_2$), 28.4 (3$CH_3$), 28.4 ($CH_2$), 28.2 ($CH_2$), 22.5 ($CH_2$), 14.0 ($CH_3$); ATR-FTIR (neat): 3359, 2956, 2871, 1713, 1609, 1248, 1136 $cm^{-1}$; HRMS (ESI) m/z calculated for $C_{32}H_{41}NO_5$[M]$^+$: 520.3057, found: 520.3043.

tert-butyl(2-((4-methoxy-4''-(pentyloxy)-[1,1':4',1''-terphenyl]-2-yl)oxy)ethyl)carbamate (3e)

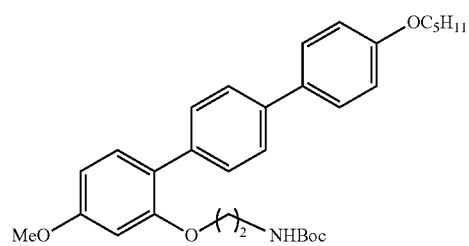

General procedure III was followed by using 150 mg of 2a (0.414 mmol), 99.1 mg 1e (0.828 mmol), 137 mg of KI (0.828 mmol), and 0.49 mL of KOt-Bu solution in 5.52 mL THF. Purification by flash column chromatography (100:0→85:15 hexanes:EtOAc) on $SiO_2$ afforded 3e (69 mg, 33%) as an off-white solid, mp=102-103° C. $^1$H NMR (400 MHz, $CDCl_3$): δ 7.63-7.50 (m, 6H), 7.30 (d, J=8.4 Hz, 1H), 6.98 (d, J=8.6 Hz, 2H), 6.61 (dd, J=8.4, 2.4 Hz, 1H), 6.56 (d, J=2.4 Hz, 1H), 4.80 (br. s, 1H), 4.05-3.97 (m, 4H), 3.85 (s, 3H), 3.45 (q, J=5.4 Hz, 2H), 1.82 (pen, J=8.0 Hz, 2H), 1.51-1.42 (m, 4H), 1.41 (s, 9H), 0.95 (t, J=7.1 Hz, 3H); $^{13}$C NMR (100 MHz, CDCl$_3$): δ 160.2 (C), 158.7 (C), 156.4 (C), 155.8 (C), 139.0 (C), 136.6 (C), 133.2 (C), 131.2 (CH), 129.7 (2CH), 128.0 (2CH), 126.3 (2CH), 123.6 (C), 114.8 (2CH), 105.9 (CH), 100.5 (CH), 79.5 (C), 68.1 (2CH$_2$), 55.5 (OCH$_3$), 40.0 (CH$_2$), 29.0 (CH$_2$), 28.4 (3CH$_3$), 28.2 (CH$_2$), 22.5 (CH$_2$), 14.0 (CH$_3$); ATR-FTIR (neat): 3374, 2955, 2870, 1681, 1608, 1510, 1250, 1163 cm$^{-1}$; HRMS (ESI) m/z calculated for C$_{31}$H$_{39}$NO$_5$[M]$^+$: 506.2901, found: 506.2888.

tert-butyl(12-((4-butoxy-4''-(pentyloxy)-[1,1':4',1''-terphenyl]-2-yl)oxy)dodecyl)carbamate (3f)

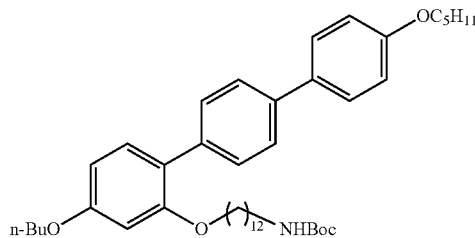

General procedure III was followed by using 90 mg of 2b (0.222 mmol), 168 mg 1a (0.444 mmol), 52 mg of KI (0.444 mmol), and 0.26 mL of KOt-Bu solution in 2.96 mL THF. Purification by flash column chromatography (100:0→85:15 hexanes:EtOAc) on SiO$_2$ afforded 3f (109 mg, 72%) as a white solid, mp=80-81° C. $^1$H NMR (400 MHz, CDCl$_3$): δ 7.64-7.53 (m, 6H), 7.30 (d, J=8.3 Hz, 1H), 6.99 (d, J=8.4 Hz, 2H), 6.60-6.54 (m, 2H), 4.56 (br s, 1H), 4.01 (t, J=6.5 Hz, 4H), 3.97 (t, J=6.4 Hz, 2H), 3.11 (q, J=6.7 Hz, 2H), 1.89-1.70 (m, 6H), 1.60-1.38 (m, 10H), 1.47 (s, 9H), 1.35-1.20 (m, 14H), 1.02 (t, J=7.4 Hz, 3H), 0.97 (t, J=7.1 Hz, 3H); $^{13}$C NMR (100 MHz, CDCl$_3$): δ 159.8 (C), 158.6 (C), 157.1 (C), 156.0 (C), 138.6 (C), 136.9 (C), 133.4 (C), 131.0 (CH), 129.8 (2CH), 127.9 (2CH), 126.0 (2CH), 123.1 (C), 114.7 (2CH), 105.3 (CH), 100.4 (CH), 78.9 (C), 68.4 (CH$_2$), 68.1 (CH$_2$), 67.8 (CH$_2$), 40.6 (CH$_2$), 31.4 (CH$_2$), 30.5 (CH$_2$), 29.6 (2CH$_2$), 29.5 (CH$_2$), 29.3 (CH$_2$), 29.3 (CH$_2$), 29.1 (CH$_2$), 29.0 (CH$_2$), 28.5 (3CH$_3$), 28.3 (2CH$_2$), 26.8 (CH$_2$), 26.1 (CH$_2$), 22.5 (CH$_2$), 19.3 (CH$_2$), 14.1 (CH$_3$), 13.9 (CH$_3$); ATR-FTIR (neat): 3369, 2923, 2850, 1686, 1609, 1518, 1490, 1248, 1180 cm$^{-1}$; HRMS (ESI) m/z calculated for C$_{44}$H$_{65}$NO$_5$[M]$^+$: 688.4936, found: 688.4928.

tert-butyl(6-((4-butoxy-4''-(pentyloxy)-[1,1':4',1''-terphenyl]-2-yl)oxy)hexyl)carbamate (3g)

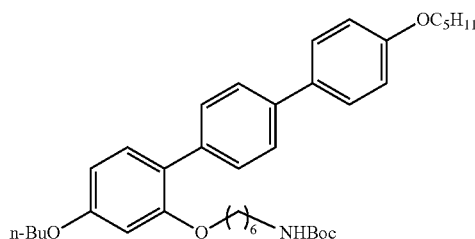

General procedure III was followed by using 150 mg of 2b (0.371 mmol), 219 mg 1b (0.742 mmol), 123 mg of KI (0.742 mmol), and 0.44 mL of KOt-Bu solution in 4.95 mL THF. Purification by flash column chromatography (100:0→85:15 hexanes:EtOAc) on SiO$_2$ afforded 3g (162 mg, 72%) as a white solid, mp=97-98° C. $^1$H NMR (400 MHz, CDCl$_3$): δ 7.61-7.51 (m, 6H), 7.27 (d, J=8.3 Hz, 1H), 6.97 (d, J=8.4 Hz, 2H), 6.60-6.53 (m, 2H), 4.40 (br. s, 1H), 4.00 (t, J=6.6 Hz, 4H), 3.95 (t, J=6.4 Hz, 2H), 3.11-3.00 (m, 2H), 1.88-1.66 (m, 6H), 1.55-1.45 (m, 6H), 1.44 (s, 9H), 1.36-1.27 (m, 6H), 0.99 (t, J=7.4 Hz, 3H), 0.94 (t, J=7.1 Hz, 3H); $^{13}$C NMR (100 MHz, CDCl$_3$): δ 159.7 (C), 158.6 (C), 156.9 (C), 156.0 (C), 138.6 (C), 136.9 (C), 133.4 (C), 131.0 (CH), 129.7 (2CH), 128.0 (2CH), 126.0 (2CH), 123.1 (C), 114.7 (2CH), 105.4 (CH), 100.4 (CH), 79.0 (C), 68.3 (CH$_2$), 68.1 (CH$_2$), 67.8 (CH$_2$), 40.5 (CH$_2$), 31.4 (CH$_2$), 30.0 (CH$_2$), 29.0 (2CH$_2$), 28.4 (3CH$_3$), 28.2 (CH$_2$), 26.4 (CH$_2$), 25.8 (CH$_2$), 22.5 (CH$_2$), 19.3 (CH$_2$), 14.0 (CH$_3$), 13.9 (CH$_3$); ATR-FTIR (neat): 3358, 2927, 2857, 1716, 1608, 1492, 1178 cm$^{-1}$; HRMS (ESI) m/z calculated for C$_{38}$H$_{53}$NO$_5$ [M]$^+$: 604.3997, found: 604.399.

tert-butyl(3-((4-butoxy-4''-(pentyloxy)-[1,1':4',1''-terphenyl]-2-yl)oxy)propyl)carbamate (3h)

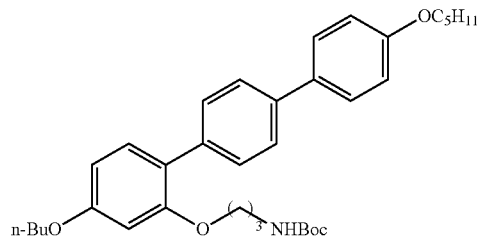

General procedure III was followed by using 115 mg of 2b (0.284 mmol), 219 mg 1d (0.568 mmol), 94 mg of KI (0.568 mmol), and 0.33 mL of KOt-Bu solution in 3.79 mL THF. Purification by flash column chromatography (100:0→85:15 hexanes:EtOAc) on SiO$_2$ afforded 3h (138 mg, 86%) as a white solid, mp=80-81° C. $^1$H NMR (400 MHz, CDCl$_3$): mp=105° C. $^1$H NMR (400 MHz, CDCl$_3$): δ 7.62-7.50 (m, 6H), 7.28 (d, J=8.3 Hz, 1H), 6.98 (d, J=8.4 Hz, 2H), 6.61-6.55 (m, 2H), 4.60 (br s, 1H), 4.00 (t, J=6.5 Hz, 6H), 3.24 (q, J=6.4 Hz, 2H), 1.93 (pen, J=6.3 Hz, 2H), 1.87-1.73 (m, 4H), 1.58-1.41 (m, 6H), 1.40 (s, 9H), 1.00 (t, J=7.4 Hz, 3H), 0.95 (t, J=7.1 Hz, 3H); $^{13}$C NMR (100 MHz, CDCl$_3$): δ 159.8 (C), 158.6 (C), 156.7 (C), 156.0 (C), 138.8 (C), 136.7 (C), 133.3 (C), 131.1 (CH), 129.7 (2CH), 128.0 (2CH), 126.2 (2CH), 123.3 (C), 114.7 (2CH), 105.9 (CH), 100.7 (CH), 79.1 (C), 68.1 (CH$_2$), 67.8 (CH$_2$), 66.4 (CH$_2$), 38.0 (CH$_2$), 29.4 (CH$_2$), 29.0 (CH$_2$), 28.4 (3CH$_3$), 28.2 (CH$_2$), 27.8 (CH$_2$), 22.5 (CH$_2$), 19.3 (CH$_2$), 14.0 (CH$_3$), 13.9 (CH$_3$); ATR-FTIR (neat): 3376, 2930, 2871, 1693, 1491, 1294, 1181 cm$^{-1}$; HRMS (ESI) m/z calculated for C$_{35}$H$_{47}$NO$_5$[M]$^+$: 562.3527, found: 562.3512.

tert-butyl(6-((4-methoxy-[1,1':4',1":4",1"'-quater-phenyl]-2-yl)oxy)hexyl)carbamatemp (3i)

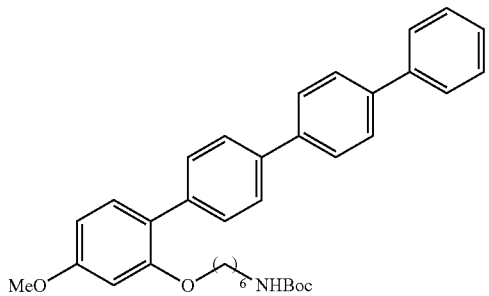

General procedure III was followed by using 93 mg of 2c (0.263 mmol), 156 mg 1b (0.526 mmol), 87 mg of KI (0.526 mmol), and 0.31 mL of KOt-Bu solution in 3.5 mL THF. Purification by flash column chromatography (100:0→85:15 hexanes:EtOAc) on $SiO_2$ afforded 3i (60 mg, 41%) as an off-white solid, mp=130-131° C. $^1$H NMR (400 MHz, $CDCl_3$): δ 7.76-7.57 (m, 10H), 7.46 (t, J=6.4 Hz, 2H), 7.39-7.33 (m, 1H), 7.32 (d, J=8.2 Hz, 1H), 6.63-6.53 (m, 2H), 4.4 (s, 1H), 3.97 (t, J=6.4 Hz, 2H), 3.86 (s, 3H), 3.15-3.01 (m, 2H), 1.80-1.71 (m, 2H), 1.48-1.45 (m, 2H), 1.42 (s, 9H), 1.37-1.30 (m, 4H); $^{13}$C NMR (100 MHz, $CDCl_3$): δ 160.3 (C), 157.0 (C), 140.7 (C), 139.9 (2C), 138.5 (C), 137.6 (C), 131.1 (CH), 129.9 (2CH), 128.8 (2CH), 127.5 (2CH), 127.3 (3CH), 127.0 (CH), 126.4 (2CH), 123.2 (C), 104.8 (CH), 100.0 (CH), 79.0 (C), 68.3 ($OCH_2$), 55.4 ($OCH_3$), 40.5 ($CH_2$), 30.0 ($CH_2$), 29.7 ($CH_2$), 29.0 ($CH_2$), 28.4 (3$CH_3$), 26.4 ($CH_2$), 25.8 ($CH_2$); ATR-FTIR (neat): 3365, 2927, 2857, 1677, 1609, 1515, 1143 cm$^{-1}$; HRMS (ESI) m/z calculated for $C_{36}H_{41}NO_4[M]^+$: 552.3108, found: 552.3101.

tert-butyl(6-((4-methoxy-4'-((4-methoxybenzyl)oxy)-[1,1'-biphenyl]-2-yl)oxy)hexyl)carbamate (3j)

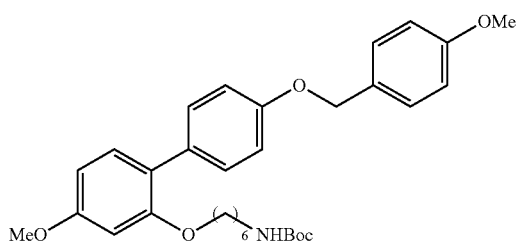

General procedure III was followed by using 120 mg of 2d (0.357 mmol), 263 mg 1b (0.714 mmol), 119 mg of KI (0.714 mmol), and 0.42 mL of KOt-Bu solution in 4.8 mL THF. Purification by flash column chromatography (100:0→85:15 hexanes:EtOAc) on $SiO_2$ afforded 3j (149 mg, 78%) as a white solid, mp=71-72° C. $^1$H NMR (400 MHz, $CDCl_3$): $^1$H NMR (400 MHz, $CDCl_3$): δ 7.43 (d, J=8.2 Hz, 2H), 7.39 (d, J=8.2 Hz, 2H), 7.22 (d, J=8.1 Hz, 2H), 6.99 (d, J=8.2 Hz, 2H), 6.93 (d, J=8.2 Hz, 2H), 6.58-6.51 (m, 2H), 5.02 (s, 1H), 4.50 (br s, 1H), 3.93 (t, J=6.3 Hz, 2H), 3.83 (s, 3H), 3.82 (s, 3H), 3.08 (q, J=6.7 Hz, 2H), 1.72 (pen, J=6.8 Hz, 2H), 1.50-1.45 (m, 2H), 1.44 (s, 9H), 1.43-1.35 (m, 4H) 1.65-1.55 (m, 2H), 1.42-1.12 (m, 6H); $^{13}$C NMR (100 MHz, $CDCl_3$): δ 159.8 (C), 159.4 (C), 157.5 (C), 156.8 (C), 156.0 (C), 131.1 (C), 130.9 (CH), 130.4 (2CH), 129.2 (2CH), 129.2 (C), 123.4 (C), 114.2 (2CH), 114.0 (2CH), 104.7 (CH), 100.0 (CH), 79.0 (C), 69.8 ($OCH_2$), 68.2 ($OCH_2$), 55.3 (2$CH_3$), 40.5 ($CH_2$), 30.0 ($CH_2$), 29.0 ($CH_2$), 28.4 (3$CH_3$), 26.4 ($CH_2$), 25.8 ($CH_2$); ATR-FTIR (neat): 3412, 2999, 2837, 1697, 1607, 1515, 1173 cm$^{-1}$; HRMS (ESI) m/z calculated for $C_{32}H_{41}NO_6[M]^+$: 536.3007, found: 536.3002.

Example 4

General Experimental Procedure for the Synthesis of Mesogenic Organic Ligands (4)

Into a 20 mL vial charged with a PTFE-coated magnetic stir bar were added 1.0 equivalent of 3 in 0.1 M dry DCM. The reaction mixture was placed in an ice bath, and then 15 equivalents of trifluoroacetic acid were added slowly. After 2 hours, the reaction mixture was quenched with saturated sodium bicarbonate and extracted three times with DCM. The organic layer was passed through a pad of anhydrous sodium sulfate and removed under reduced pressure to afford 4a-j as a solid.

12-((4-methoxy-4"-(pentyloxy)-[1,1':4',1"-terphenyl]-2-yl)oxy)dodecan-1-amine (4e)

General procedure IV was followed by using 120 mg of 3a (0.186 mmol), 0.213 mL TFA and 1.9 mL DCM. (95 mg, 94%) of 4e was obtained as a white solid, mp=109-110° C. $^1$H NMR (400 MHz, $CDCl_3$): δ 7.84 (br, (s), 1H), 7.62-7.50 (m, 6H), 7.29 (d, J=8.4 Hz, 1H), 6.96 (d, J=8.4 Hz, 2H), 6.59-6.52 (m, 2H), 3.99 (t, J=6.6 Hz, 2H), 3.94 (t, J=6.5 Hz, 2H), 3.84 (s, 3H), 1.81 (pen, J=7.2 Hz, 2H), 1.74 (pen, J=7.2 Hz, 2H), 1.62 (pen, J=7.4 Hz, 2H), 1.50-1.39 (m, 6H), 1.32-1.20 (m, 14H), 0.94 (t, J=7.1 Hz, 3H); $^{13}$C NMR (100 MHz, $CDCl_3$): δ 160.2 (C), 158.6 (C), 157.0 (C), 138.7 (C), 136.8 (C), 133.4 (C), 131.0 (CH), 129.7 (2CH), 127.9 (2CH), 126.0 (2CH), 123.2 (C), 114.7 (2CH), 104.7 (CH), 99.9 (CH), 68.4 ($CH_2$), 68.1 ($CH_2$), 55.4 ($OCH_3$), 40.0 ($CH_2$), 29.6 ($CH_2$), 29.5 ($CH_2$), 29.4 ($CH_2$), 29.3 ($CH_2$), 29.2 ($CH_2$), 29.1 ($CH_2$), 29.0 ($CH_2$), 28.9 ($CH_2$), 28.2 ($CH_2$), 27.5 ($CH_2$), 26.3 ($CH_2$), 26.1 ($CH_2$), 22.5 ($CH_2$), 14.0 ($CH_3$); ATR-FTIR (neat): 2925, 2855, 1607, 1490, 1202, 1139 cm$^{-1}$; HRMS (ESI) m/z calculated for $C_{36}H_{51}NO_3[M]^+$: 546.3942, found: 546.3924.

6-((4-methoxy-4"-(pentyloxy)-[1,1':4',1"-terphenyl]-2-yl)oxy)hexan-1-amine (4a)

General procedure IV was followed by using 260 mg of 3b (0.463 mmol), 0.53 mL TFA and 4.6 mL DCM. (207 mg, 97%) of 4a was obtained as a white solid, mp=125-126° C. $^1$H NMR (400 MHz, $CDCl_3$): δ 7.59-7.48 (m, 6H), 7.27 (d, J=8.4 Hz, 1H), 6.95 (d, J=8.8 Hz, 2H), 6.58-6.51 (m, 2H), 3.97 (t, J=6.6 Hz, 2H), 3.91 (t, J=6.4 Hz, 2H), 3.82 (s, 3H), 2.75 (t, J=7.4 Hz, 2H), 1.80 (pen, J=6.5 Hz, 2H), 1.71 (pen, J=6.5 Hz, 2H), 1.57-1.24 (m, 12H), 0.93 (t, J=7.1 Hz, 3H); $^{13}$C NMR (100 MHz, $CDCl_3$): δ 160.2 (C), 158.6 (C), 156.9 (C), 138.6 (C), 136.8 (C), 133.2 (C), 131.1 (CH), 129.7 (2CH), 127.9 (2CH), 126.0 (2CH), 123.3 (C), 114.7 (2CH), 104.9 (CH), 99.9 (CH), 68.1 ($CH_2$), 68.0 ($CH_2$), 55.4 ($OCH_3$), 40.5 ($CH_2$), 29.5 ($CH_2$), 29.0 ($CH_2$), 28.8 ($CH_2$), 28.2 ($CH_2$), 26.0 ($CH_2$), 25.6 ($CH_2$), 22.5 ($CH_2$), 14.0 ($CH_3$); ATR-FTIR (neat): 2936.3, 2868.6, 1677.7, 1607.3,

4-((4-methoxy-4"-(pentyloxy)-[1,1':4',1"-terphenyl]-2-yl)oxy)butan-1-amine (4b)

General procedure IV was followed by using 115 mg of 3c (0.215 mmol), 0.25 mL TFA and 2.2 mL DCM. (83 mg, 93%) of 4b was obtained as a white solid, mp=130-131° C. $^1$H NMR (400 MHz, CDCl$_3$): δ 7.58-7.48 (m, 6H), 7.27 (d, J=8.4 Hz, 1H), 6.94 (d, J=8.7 Hz, 2H), 6.56 (dd, J=8.4, 2.4 Hz, 2H), 6.51 (d, J=3.9 Hz, 1H), 3.97 (t, J=6.6 Hz, 2H), 3.92 (t, J=6.1 Hz, 2H), 3.82 (s, 3H), 2.75 (br s, 2H), 1.83-1.61 (m, 6H), 1.49-1.33 (m, 4H), 0.94 (t, J=7.1 Hz, 3H); $^{13}$C NMR (100 MHz, CDCl$_3$): δ 160.1 (C), 158.6 (C), 156.6 (C), 138.7 (C), 136.7 (C), 133.1 (C), 131.2 (CH), 129.7 (2CH), 127.9 (2CH), 126.0 (2CH), 123.3 (C), 114.7 (2CH), 105.1 (CH), 100.0 (CH), 68.0 (CH$_2$), 67.7 (CH$_2$), 55.4 (OCH$_3$), 39.8 (CH$_2$), 29.0 (CH$_2$), 28.2 (CH$_2$), 26.3 (CH$_2$), 26.2 (CH$_2$), 22.5 (CH$_2$), 14.0 (CH$_3$); ATR-FTIR (neat): 2935, 2871, 1607, 1490, 1253, 1201 cm$^{-1}$; HRMS (ESI) m/z calculated for C$_{28}$H$_{35}$NO$_3$[M]$^+$: 434.2690, found: 434.2672.

3-((4-methoxy-4"-(pentyloxy)-[1,1':4,1"-terphenyl]-2-yl)oxy)propan-1-amine (4c)

General procedure IV was followed by using 160 mg of 3d (0.308 mmol), 0.35 mL TFA and 3.1 mL DCM. (125 mg, 97%) of 4c was obtained as a white solid, mp=147-150° C. $^1$H NMR (400 MHz, CDCl$_3$): δ 7.56 (d, J=8.8 Hz, 2H), 7.53 (d, J=8.4 Hz, 1H), 7.32 (br s, 2H), 7.21 (d, J=8.4 Hz, 2H), 6.89 (d, J=8.7 Hz, 2H), 3.96 (t, J=5.6 Hz, 2H), 3.89 (t, J=6.6 Hz, 2H), 3.84 (s, 3H), 2.65 (br s, 2H), 1.89 (pen, J=5.7 Hz, 2H), 1.75 (pen, J=5.8 Hz, 2H), 0.93 (t, J=7.0 Hz, 3H); $^{13}$C NMR (100 MHz, CDCl$_3$): δ 160.3 (C), 158.7 (C), 155.7 (C), 139.0 (C), 136.3 (C), 133.6 (C), 131.0 (CH), 129.8 (2CH), 127.9 (2CH), 126.4 (2CH), 123.2 (C), 114.8 (2CH), 105.6 (CH), 99.5 (CH), 68.1 (CH$_2$), 67.3 (CH$_2$), 55.4 (OCH$_3$), 38.6 (CH$_2$), 29.0 (CH$_2$), 28.2 (CH$_2$), 26.2 (CH$_2$), 22.5 (CH$_2$), 14.0 (CH$_3$); ATR-FTIR (neat): 2934, 2872, 1609, 1492, 1249, 1202, 1137 cm$^{-1}$; HRMS (ESI) m/z calculated for C$_{27}$H$_{33}$NO$_3$[M]$^+$: 420.2533, found: 420.2521.

2-((4-methoxy-4"-(pentyloxy)-[1,1':4',1"-terphenyl]-2-yl)oxy)ethan-1-amine (4d)

General procedure IV was followed by using 60 mg of 3e (0.119 mmol), 0.136 mL TFA and 1.2 mL DCM. (45 mg, 93%) of 4d was obtained as an off-white solid, mp=147-150° C. $^1$H NMR (400 MHz, CDCl$_3$): δ 7.56 (d, J=8.1 Hz, 2H), 7.52 (d, J=8.6 Hz, 2H), 7.27 (d, J=8.7 Hz, 2H), 6.93 (d, J=8.6 Hz, 2H), 6.66 (dd, J=8.5, 2.4 Hz, 1H), 6.54 (d, J=2.4 Hz, 1H), 4.07 (t, J=4.9 Hz, 2H), 3.95 (t, J=6.6 Hz, 2H), 3.82 (s, 3H), 3.13 (t, J=4.8 Hz, 2H), 1.79 (pen, J=6.8 Hz, 3H), 1.48-1.37 (m, 2H), 0.94 (t, J=7.0 Hz, 3H); $^{13}$C NMR (125 MHz, CD$_2$Cl$_2$): δ 160.3 (C), 158.9 (C), 155.3 (C), 139.0 (C), 132.6 (C), 132.5 (C) 131.4 (CH), 129.5 (2CH), 127.7 (2CH), 126.3 (2CH), 123.6 (C), 114.7 (2CH), 107.3 (CH), 101.2 (CH), 68.0 (CH$_2$), 64.9 (CH$_2$), 55.4 (OCH$_3$), 39.5 (CH$_2$), 29.0 (CH$_2$), 28.1 (CH$_2$), 22.5 (CH$_2$), 13.8 (CH$_3$); ATR-FTIR (neat): 2933, 2870, 1608, 1531, 1248, 1141 cm$^{-1}$; HRMS (ESI) m/z calculated for C$_{26}$H$_{31}$NO$_3$[M]$^+$: 420.2533, found: 420.2521.

1490.5, 1201.3 cm$^{-1}$; HRMS (ESI) m/z calculated for C$_{30}$H$_{39}$NO$_3$[M]$^+$: 462.3003, found: 462.3002.

12-((4-butoxy-4"-(pentyloxy)-[1,1':4,1"-terphenyl]-2-yl)oxy)dodecan-1-amine (4h)

General procedure IV was followed by using 100 mg of 3f (0.145 mmol), 0.17 mL TFA and 1.5 mL DCM. (80 mg, 94%) of 4h was obtained as a white solid, mp=70-72° C. $^1$H NMR (400 MHz, CDCl$_3$): δ 7.62-7.53 (m, 6H), 7.29 (d, J=8.4 Hz, 1H), 6.98 (d, J=8.4 Hz, 2H), 6.59-6.53 (m, 2H), 5.16 (br s, 1H), 4.00 (t, J=6.5 Hz, 4H), 3.96 (t, J=6.5 Hz, 2H), 2.79 (t, J=7.4 Hz, 2H), 1.86-1.70 (m, 6H), 1.68-1.27 (m, 2H), 1.58-1.32 (m, 14H), 1.25 (s, 9H), 1.00 (t, J=7.4 Hz, 3H), 0.99 (t, J=7.1 Hz, 3H); $^{13}$C NMR (100 MHz, CDCl$_3$): δ 159.8 (C), 158.6 (C), 157.0 (C), 138.6 (C), 136.9 (C), 133.4 (C), 131.0 (CH), 129.7 (2CH), 127.9 (2CH), 126.0 (2CH), 123.0 (C), 114.7 (2CH), 105.3 (CH), 100.4 (CH), 68.5 (CH$_2$), 68.1 (CH$_2$), 67.8 (CH$_2$), 40.9 (CH$_2$), 31.4 (CH$_2$), 30.3 (CH$_2$), 29.6 (CH$_2$), 29.5 (2CH$_2$), 29.3 (CH$_2$), 29.2 (CH$_2$), 29.1 (CH$_2$), 29.0 (CH$_2$), 28.2 (2CH$_2$), 26.6 (CH$_2$), 26.1 (CH$_2$), 22.5 (CH$_2$), 19.3 (CH$_2$), 14.0 (CH$_3$), 13.9 (CH$_3$); ATR-FTIR (neat): 2926, 2854, 1609, 1491, 1247, 1182 cm$^{-1}$; HRMS (ESI) m/z calculated for C$_{39}$H$_{57}$NO$_3$[M]$^+$: 588.4411, found: 588.4398.

6-((4-butoxy-4"-(pentyloxy)-[1,1':4',1"-terphenyl]-2-yl)oxy)hexan-1-amine (4f)

General procedure IV was followed by using 150 mg of 3g (0.248 mmol), 0.28 mL TFA and 2.5 mL DCM. (120 mg, 96%) of 4f was obtained as a white solid, mp=100-101° C. $^1$H NMR (400 MHz, CDCl$_3$): δ 7.59-7.52 (m, 6H), 7.26 (d, J=8.4 Hz, 1H), 6.95 (d, J=8.4 Hz, 2H), 6.58-6.50 (m, 2H), 4.02-3.95 (m, 4H), 3.91 (t, J=6.4 Hz, 2H), 2.76 (t, J=7.4 Hz, 2H), 1.84-1.75 (m, 4H), 1.75-1.66 (m, 2H), 1.58-1.29 (m, 12H), 0.98 (t, J=7.1 Hz, 3H), 0.93 (t, J=7.1 Hz, 3H); $^{13}$C NMR (100 MHz, CDCl$_3$): δ 159.9 (C), 158.6 (C), 156.9 (C), 139.0 (C), 136.8 (C), 132.2 (C), 131.1 (CH), 129.7 (2CH), 128.0 (2CH), 126.0 (2CH), 123.0 (C), 114.7 (2CH), 105.5 (CH), 100.4 (CH), 68.1 (CH$_2$), 68.0 (CH$_2$), 67.8 (CH$_2$), 40.3 (CH$_2$), 31.4 (CH$_2$), 29.0 (CH$_2$), 28.9 (CH$_2$), 28.8 (CH$_2$), 28.2 (CH$_2$), 26.0 (CH$_2$), 25.6 (CH$_2$), 22.5 (CH$_2$), 19.3 (CH$_2$), 14.0 (CH$_3$), 13.9 (CH$_3$); ATR-FTIR (neat): 2956, 29354, 2871, 1677, 1609, 1530, 1202, 1182 cm$^{-1}$; HRMS (ESI) m/z calculated for C$_{30}$H$_{39}$NO$_3$[M]$^+$: 504.3472, found: 504.3481.

3-((4-butoxy-4"-(pentyloxy)-[1,1':4',1"-terphenyl]-2-yl)oxy)propan-1-amine (4g)

General procedure IV was followed by using 130 mg of 3h (0.231 mmol), 0.26 mL TFA and 2.31 mL DCM. (102 mg, 96%) of 4g was obtained as a white solid, mp=122-123° C. $^1$H NMR (400 MHz, CDCl$_3$): δ 7.60-7.51 (m, 4H), 7.40 (d, J=8.4 Hz, 2H), 7.20 (d, J=8.3 Hz, 1H), 6.89 (d, J=8.4 Hz, 2H), 6.59 (dd, J=8.4, 2.3 Hz, 1H), 6.48 (d, J=2.3 Hz, 1H), 4.03-3.95 (m, 4H), 3.90 (t, J=6.6 Hz, 2H), 2.63 (t, J=5.9 Hz, 2H), 1.92-1.85 (m, 2H), 1.85-1.70 (m, 4H), 1.56-1.47 (m, 4H), 1.00 (t, J=7.4 Hz, 2H), 0.93 (t, J=7.00 Hz, 2H); $^{13}$C NMR (100 MHz, CDCl$_3$): δ 159.9 (C), 158.7 (C), 155.7 (C), 139.0 (C), 136.4 (C), 132.6 (C), 131.0 (CH), 129.8 (2CH), 128.0 (2CH), 126.4 (2CH), 123.0 (C), 114.7 (2CH), 106.2 (CH), 99.8 (CH), 68.0 (CH$_2$), 67.9 (CH$_2$), 67.5 (CH$_2$), 38.7 (CH$_2$), 31.3 (CH$_2$), 29.0 (CH$_2$), 28.2 (CH$_2$), 26.4 (CH$_2$), 22.5 (CH$_2$), 19.3 (CH$_2$), 14.0 (CH$_3$), 13.9 (CH$_3$); ATR-FTIR (neat): 2958, 2935, 2873, 1677, 1609, 1492, 1202 cm$^{-1}$; HRMS (ESI) m/z calculated for C$_{30}$H$_{39}$NO$_3$[M]$^+$: 462.3003, found: 462.3000.

6-((4-methoxy-[1,1':4',1":4",1'''-quaterphenyl]-2-yl)oxy)hexan-1-amine (4i)

General procedure IV was followed by using 52 mg of 3i (0.148 mmol), 0.23 mL TFA (20 equiv.) and 1.5 mL DCM. A mixture of hexanes:EtOAC (4:1) was added to the solid and the product was filtered to afford (20 mg, 47%) of 4i as a light yellow solid, mp=125-126° C. $^1$H NMR (400 MHz, CDCl$_3$): δ 7.73-7.55 (m, 11H), 7.73-7.55 (m, 2H), 7.29 (d, J=8.4 Hz, 1H), 6.57 (dd, J=8.3, 2.4 Hz, 1H), 6.53 (d, J=2.4 Hz, 1H), 3.92 (t, J=6.4 Hz, 2H), 3.83 (s, 3H), 3.38 (br, s, 2H), 2.74 (br, s, 2H), 1.72 (pen, J=6.7 Hz, 2H), 1.59-1.45 (m, 2H), 1.40 (pen, J=7.1 Hz, 2H), 1.31-1.27 (m, 2H); $^{13}$C NMR (100 MHz, CDCl$_3$): δ 160.3 (C), 156.9 (C), 156.9 (C), 140.7 (C), 139.9 (C), 138.4 (C), 137.6 (C), 131.2 (CH), 129.8 (2CH), 128.8 (2CH), 127.5 (2CH), 127.4 (CH), 127.3 (2CH), 127.0 (2CH), 126.4 (2CH), 123.1 (C), 104.9 (CH), 100.0 (CH), 68.1 (CH$_2$), 55.4 (OCH$_3$), 28.8 (CH$_2$), 26.2 (CH$_2$), 25.7 (CH$_2$); ATR-FTIR (neat): 2956, 29354, 2871, 1677, 1609, 1530, 1202, 1182 cm$^{-1}$; HRMS (ESI) m/z calculated for C$_{31}$H$_{33}$NO$_2$[M]$^+$: 452.2584, found: 452.2585.

6-((4-methoxy-4'-((4-methoxybenzyl)oxy)-[1,1'-biphenyl]-2-yl)oxy)hexan-1-amine (4j)

General procedure IV was followed by using 124 mg of 3j (0.231 mmol), 0.27 mL TFA and 2.3 mL DCM. (94 mg, 93%) of 4j was obtained as a white solid, mp=36-37° C. $^1$H NMR (400 MHz, CDCl$_3$): δ 7.29 (d, J=8.3 Hz, 2H), 7.14 (d, J=8.3 Hz, 2H), 7.01 (s, 1H), 6.85-6.76 (m, 5H), 6.50 (s, 1H), 5.22 (s, 1H), 3.86 (s, 3H), 3.81 (s, 3H), 3.76 (t, J=8.6 Hz, 2H), 3.72 (s, 3H), 2.61 (t, J=7.5 Hz, 2H), 1.65-1.55 (m, 2H), 1.42-1.12 (m, 6H); $^{13}$C NMR (100 MHz, CDCl$_3$): δ 157.6 (C), 157.0 (C), 155.5 (C), 155.3 (C), 133.5 (C), 131.7 (CH), 130.8 (2CH), 129.7 (3CH), 123.5 (C), 122.6 (C), 115.2 (2CH), 113.6 (2CH), 98.0 (CH), 69.4 (OCH$_2$), 55.6 (OCH$_3$), 55.2 (OCH$_3$), 40.9 (CH$_2$), 34.4 (CH$_2$), 31.3 (CH$_2$), 29.1 (CH$_2$), 26.1 (CH$_2$), 25.9 (CH$_2$); ATR-FTIR (neat): 2932, 2857, 1609, 1510, 1244, 1175 cm$^{-1}$; HRMS (ESI) m/z calculated for C$_{27}$H$_{33}$NO$_4$[M]$^+$: 436.2482, found: 436.2472.

General Procedure—Organic Ligands with Thiol Tether

Scheme 2

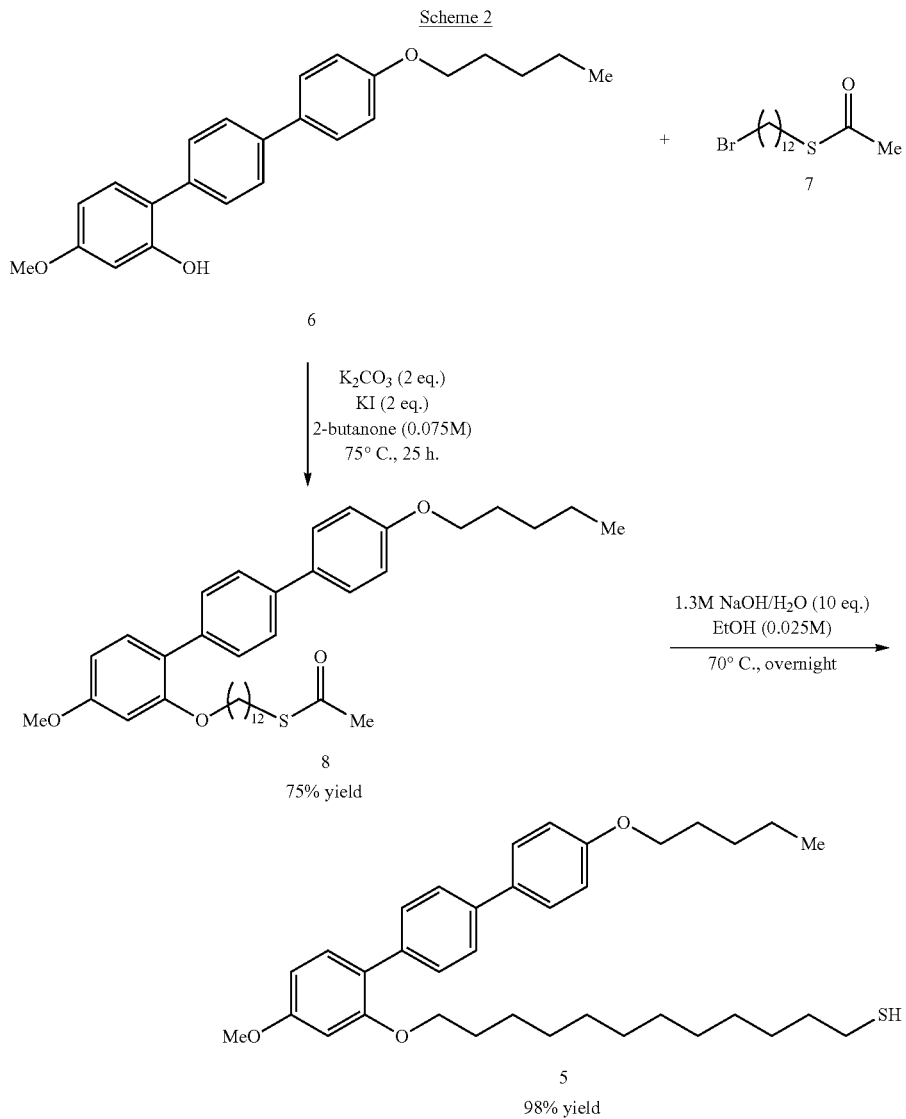

In some embodiments, a subject organic ligand containing a thiol tether (e.g., compound (5)) was synthesized according to the procedure outlined in Scheme 2. With reference to Scheme 2, the sequence of reactions proceeds as follows: after preparation of ligand core 6 (e.g., via a Suzuki coupling between a bromide and a boronic acid as described in Scheme 1). The ortho-functionality was then added via coupling of the phenol 6 with bromothiolate 7. The thiol protecting group of a compound of formula 8 was then removed to yield the organic ligand (5).

Example 5

Exemplary Experimental Procedure for the Synthesis of Thiolate Protected Organic Ligands (e.g., Compound 8)

S-(12-((4-methoxy-4"-(pentyloxy)-[1,1':4',1"-terphenyl]-2-yl)oxy)dodecyl) ethanethioate (8)

Into a 20 mL vial charged with a PTFE-coated magnetic stir bar were added 89.8 mg of 4-methoxy-4"-(pentyloxy)-[1,1':4',1"-terphenyl]-2-ol (6, 0.248 mmol) and 96.2 mg of S-(12-bromododecyl) ethanethioate (7, 0.297 mmol) in 3.3 mL of 2-butanone (0.075 M). 68.6 mg of $K_2CO_3$ (0.496 mmol) and 82.3 mg of KI (0.496 mmol) were added to the reaction mixture. Reaction was heated to 75° C. and stopped after 25 hours. The solvent was evaporated and the crude mixture was extracted with water and EtOAc. The organic layer was passed through a pad of anhydrous sodium sulfate and removed under reduced pressure. Purification by column chromatography (100:0 to 95:5 hexanes:EtOAc) on $SiO_2$ afforded 111.6 mg of the product 8 (75%). $^1H$ NMR (400 MHz, $CDCl_3$): δ 7.60-7.55 (m, 6H), 7.30 (dd, J=7.6, 1.1 Hz, 1H), 6.99-6.96 (m, 2H), 6.59-6.56 (m, 2H), 4.00 (t, J=6.6 Hz, 2H), 3.96 (t, J=6.4 Hz, 2H), 3.85 (s, 3H), 2.85 (t, J=7.2 Hz, 2H), 2.32 (s, 3H), 1.82 (pen, J=6.8 Hz, 2H), 1.75 (pen, J=6.8 Hz, 2H), 1.56-1.24, (m, 22H), 0.95 (t, J=7.2 Hz, 3H); $^{13}C$ NMR (100 MHz, $CDCl_3$): δ 196.2 (CO), 160.3 (C), 158.7 (C), 157.2 (C), 138.8 (C), 136.9 (C), 133.6 (C), 131.2 (CH), 129.9 (2CH), 128.1 (2CH), 126.2 (2CH), 123.5 (C), 114.9 (2CH), 104.8 (CH), 100.1 (CH), 68.6 ($OCH_2$), 68.2 ($OCH_2$), 55.6 ($OCH_3$), 30.8 ($CH_3$), 29.7 (2$CH_2$), 29.7 ($CH_2S$), 29.6 ($CH_2$), 29.6 ($CH_2$), 29.4 ($CH_2$), 29.3 ($CH_2$), 29.3 ($CH_2$), 29.2 ($CH_2$), 29.2 ($CH_2$), 29.0 ($CH_2$), 28.4 ($CH_2$), 26.2 ($CH_2$), 22.6 ($CH_2$), 14.2 ($CH_3$).

Example 6

Exemplary Experimental Procedure for the Synthesis of Organic Ligands with a Thiol Tether (e.g., Compound 5)

12-((4-methoxy-4"-(pentyloxy)-[1,1':4',1"-terphenyl]-2-yl)oxy)dodecane-1-thiol (5)

Into a 20 mL vial charged with a PTFE-coated magnetic stir bar were added 183.9 mg of S-(12-((4-methoxy-4"-(pentyloxy)-[1,1':4',1"-terphenyl]-2-yl)oxy)dodecyl) ethanethioate (8, 0.304 mmol) in 12.2 mL of EtOH. 121.6 mg of NaOH (3.04 mmol) in 2.34 mL of water was added to the reaction mixture. Reaction was heated to 70° C. overnight. The solvent was evaporated and the crude mixture was extracted with DCM. The organic layer was passed through a pad of anhydrous sodium sulfate and removed under reduced pressure to afford 167.5 mg of the product 5 (98%). $^1H$ NMR (400 MHz, $CDCl_3$): δ 7.62-7.49 (m, 6H), 7.30 (d, J=8.4 Hz, 1H), 6.97 (d, J=8.4 Hz, 2H), 6.63-6.53 (m, 2H), 4.00 (t, J=6.6 Hz, 2H), 3.96 (t, J=6.5 Hz, 2H), 3.85 (s, 3H), 2.66 (t, J=7.4 Hz, 2H), 1.82 (pen, J=7.1, 2H), 1.74 (pen, J=7.0, 2H), 1.65 (pen, J=7.3, 2H), 1.51-1.20 (m, 21H), 0.95 (t, J=7.1 Hz, 3H); $^{13}C$ NMR (100 MHz, $CDCl_3$): δ 160.2 (C), 158.6 (C), 157.1 (C), 138.7 (C), 136.8 (C), 133.4 (C), 131.1 (CH), 129.8 (2CH), 128.0 (2CH), 126.1 (2CH), 123.3 (C), 114.7 (2CH), 104.7 (CH), 99.9 (CH), 68.4 ($OCH_2$), 68.1 ($OCH_2$), 55.4 ($OCH_3$), 39.2 ($CH_2$), 29.59 ($CH_2$), 29.57 ($CH_2$), 29.54 ($CH_2$), 29.52 ($CH_2$), 29.3 (2$CH_2$), 29.2 ($CH_2$), 29.1 ($CH_2$), 29.0 ($CH_2$), 28.5 ($CH_2$), 28.2 ($CH_2$), 26.1 ($CH_2$), 22.5 ($CH_2$) 14.1 ($CH_3$); ATR-FTIR (neat): 2959, 2852, 1609, 1490, 1276 $cm^{-1}$; HRMS (ESI) m/z calculated for $C_{36}H_{50}SO_3[M]^+$: 563.3553, found: 563.3531.

Example 7—Differential Scanning Calorimetry of Ligands

Small amounts (6-10 mg) of ligand in the crystal phase were encapsulated in an aluminum pan and cycled through melting and recrystallization at least once before recording a differential scanning calorimetry (DSC) trace. All data was collected on melting with a temperature ramp rate of 10° C./min. An empty pan was used for the reference material. Enthalpies for each transition were calculated as the area under each peak.

Figure 3:
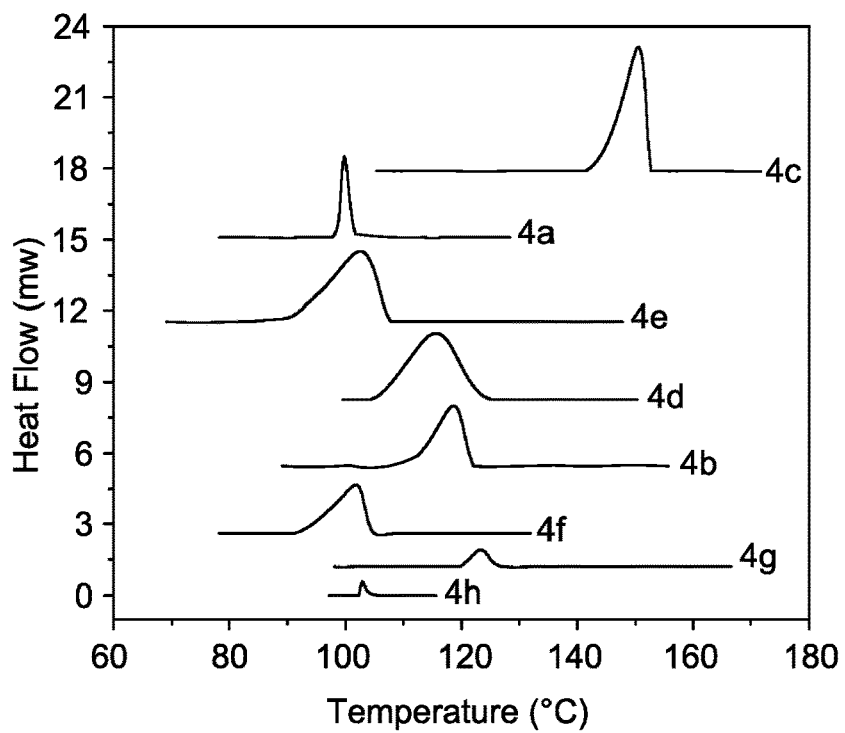
FIG. 3 depicts the differential scanning calorimetry for pure organic ligands (4a-4h) showing baseline corrected heat flow as a function of temperature.

FIG. 3 depicts the differential scanning calorimetry for pure organic ligands 4a-4h showing baseline corrected heat flow as a function of temperature. Each of ligands 4a-4h exhibits a single peak, indicative of a direct phase transition from the crystal to isotropic liquid phase.

Example 8—Nanocapsule Preparation

The subject nanocapsules were prepared according to the procedures outlined in WO 2016/10637, the disclosure of which is incorporated by reference herein.

Nanocapsules were prepared via nematic templating by heating 0.15 et % of functionalized quantum dots in 4-cyano-4'-pentylbiphenyl above the nematic-isotropic transition point (34° C.), then cooling back to the nematic phase in an Eppendorf tube. After gentle centrifugation, the Nanocapsules were inserted into 1.5 mm borage glass x-ray capillaries, and further centrifuged to form a pellet at the bottom of the capillary.

Example 8—Polarized Optical Microscopy Procedure

A thin film of each material was enclosed between a standard glass slide and cover slip, and slowly heated to the isotropic phase. The films were then cooled into the crystal phase and reheated several times on a Linkham microscopy heating stage to identify a reversible phase sequence on the polarized optical microscope.

Figure 4:
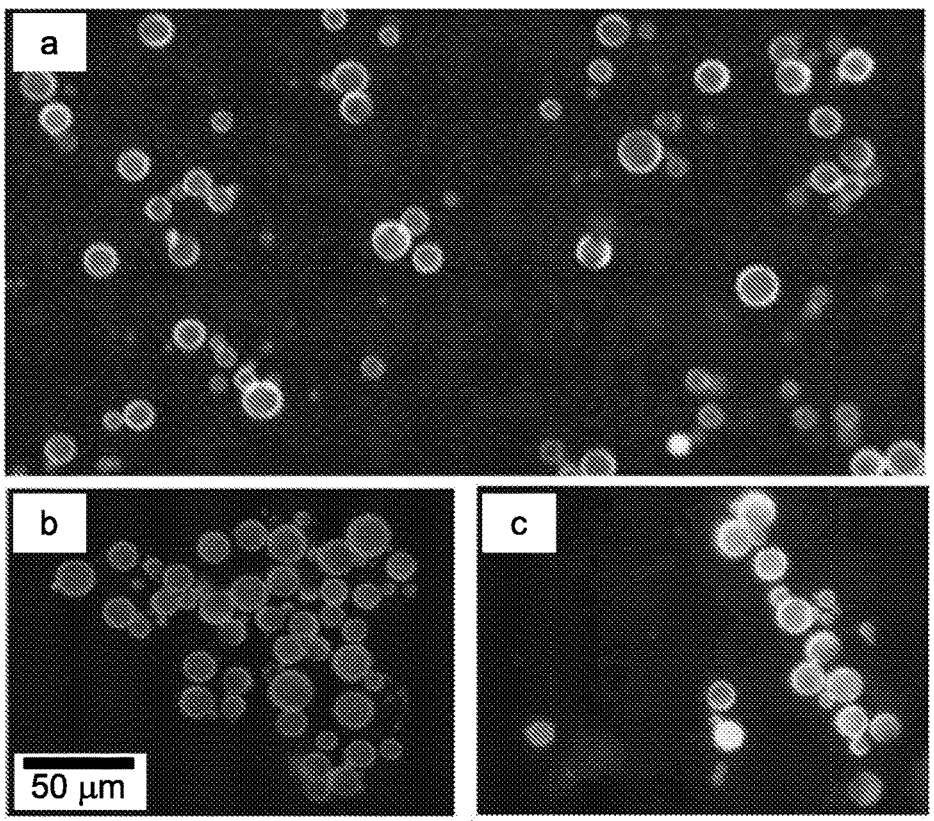
FIG. 4, panels A-C, shows representative fluorescence microscopy images of spherical nanocapsules formed from organic-ligand (4a) functionalized quantum dots (540 nm CdSe/ZnS) following dispersion in 4-cyano-4'-pentylbiphenyl (0.15 wt %). Panel A shows an image of the nanocapsules obtaining after depositing on the slide. Panel B shows an image of the nanocapsules after reheating the slide through the clearing point (34° C.) and re-cooling. Panel C shows an image of the nanocapsules after reheating the slide to 350° C.

FIG. 4, panels A-C, shows representative fluorescence microscopy images of spherical nanocapsules formed from an exemplary organic-ligand (4a) functionalized quantum dots (540 nm CdSe/ZnS) following dispersion in 4-cyano-4'-pentylbiphenyl (0.15 wt %). Panel A shows an image of the nanocapsules obtaining after depositing on the slide. Panel B shows an image of the nanocapsules after reheating the slide through the clearing point (34° C.) and re-cooling. Panel C shows an image of the nanocapsules after reheating the slide to 350° C.

With reference to FIG. 4, panel B, reheating to above the nematic phase clearing point of 34° C. and re-cooling did not destroy the capsules.

With reference to FIG. 4, panel C, heating to a temperature of 350° also did not destroy the capsules. These experiments are indicative of the thermostability of quantum dots functionalized with an exemplary organic ligand and demonstrates their suitability for various materials applications.

Example 9—Ligand Exchange Process and Quantification by $^1$H NMR Spectroscopy For surface modification of quantum dots, the ODA ligands were exchanged with exemplary subject organic ligands (e.g., compound 4a). This exchange involves 1 mL of quantum dots (CdSe/ZnS nanocrystal) solution with an octadecylamine ligand (ODA) attached and mixed with 1 mL of acetone. The free ligand was removed by centrifugation at 7000 rpm for 10 mins. The supernatant was discarded and then the last step was repeated again with the precipitate two times by adding 1 mL of acetone. After washing, the precipitate was dissolved in 1 mL of chloroform and mixed with 1 mL solution of the subject organic ligand in chloroform (0.01 g/mL). ODA ligands were then exchanged with the subject ligand on the quantum dot surface by heating at 40° C. and stirring the solution at 200 rpm for 5 hours. The mixture was then removed from the heating stage and left to cool to room temperature. The free ligand was removed by washing with 1 mL of ethyl acetate and centrifuged for 10 min, then washed again twice with 1 mL of ethyl acetate. Finally, the precipitate was dissolved in 1 mL of toluene.

Figure 5:
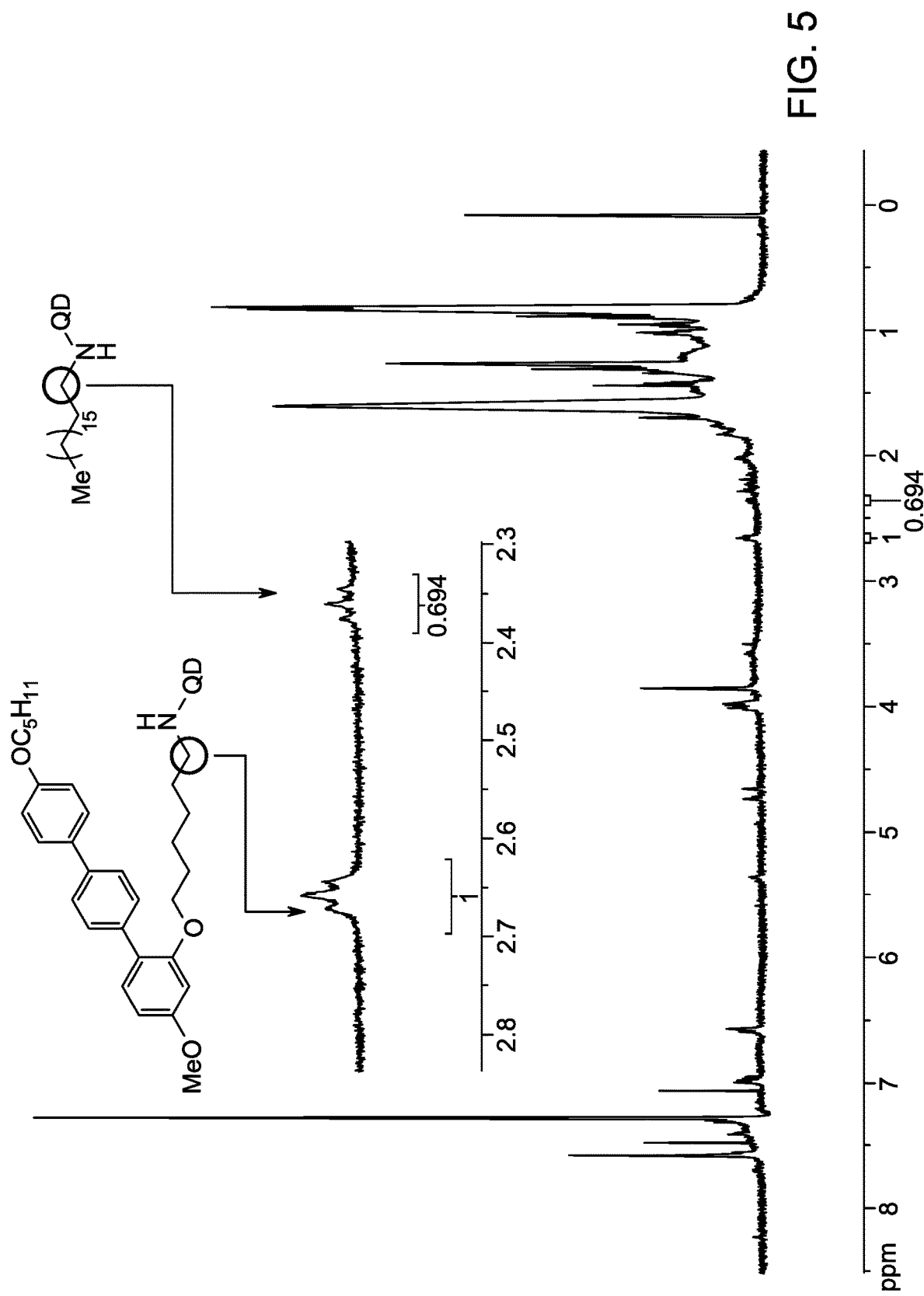
FIG. 5 shows the $^1$H NMR spectrum obtained after modification of quantum dots by exchanging octadecylamine ligands (ODA) ligands with exemplary organic ligand (4a) (500 MHz in $CDCl_3$).

Ligand exchange on the quantum dot was quantified using $^1$H NMR (in CDCl$_3$). See, e.g., FIG. 5 which shows the $^1$H NMR spectrum after ligand exchange of ODA for subject ligand (4a), obtained at 500 MHz in CDCl$_3$. The ratio of organic ligand (4a) attached to the surface of the quantum dot as compared to remaining ODA ligands is 51% to 49%.

Example 10—Preparation for Scanning Electron Microscopy (SEM) Imaging

The subject liquid crystal-functionalized quantum dots mixture (0.2 µL) was pipetted onto a copper grid with 300 mesh carbon film, while holding the composite material at a temperature above the nematic-isotropic phase transition point. The grid was then cooled into the nematic phase, forming Nanocapsules suspended in 5CB directly on the grid. Finally, the 5CB was washed from the grid with acetone by pipetting a droplet onto the grid surface then wicking and evaporating the excess solvent.

Figure 6:
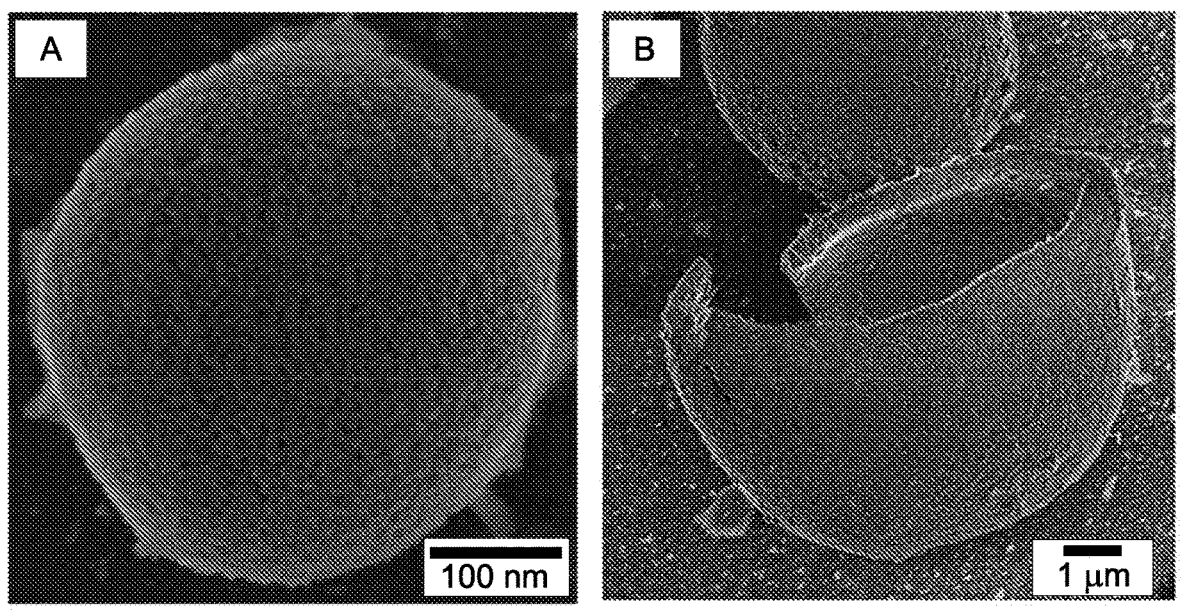
FIG. 6, panels A-B, show scanning electron microscope (SEM) images of intact and fractured nanocapsules composed of densely packed functionalized quantum dots. Panel A, shows a scanning electron microscope image of intact quantum dot nanocapsules formed from 540 nm CdSe/ZnS quantum dots functionalized with exemplary organic ligand (4a). Panel B, shows a scanning electron microscope image of fractured quantum dot nanocapsules formed from 540 nm CdSe/ZnS quantum dots functionalized with exemplary organic ligand (4a).

FIG. 6, panels A-B, show scanning electron microscope (SEM) images of intact and fractured nanocapsules composed of densely packed functionalized quantum dots. Panel A, shows a scanning electron microscope image of intact quantum dot nanocapsules formed from 540 nm CdSe/ZnS quantum dots functionalized with exemplary organic ligand (4a). Panel B, shows a scanning electron microscope image of fractured quantum dot nanocapsules formed from 540 nm CdSe/ZnS quantum dots functionalized with exemplary organic ligand (4a). The image of the fractured nanocapsules confirms that the microcapsules formed were hollow with a relatively think wall.

Example 11—Small-Angle X-Ray Scattering (SAXS) Measurements

Small-angle X-ray scattering (SAX) was used to quantify nanoparticle packing in the nanocapsules.

Figure 7:
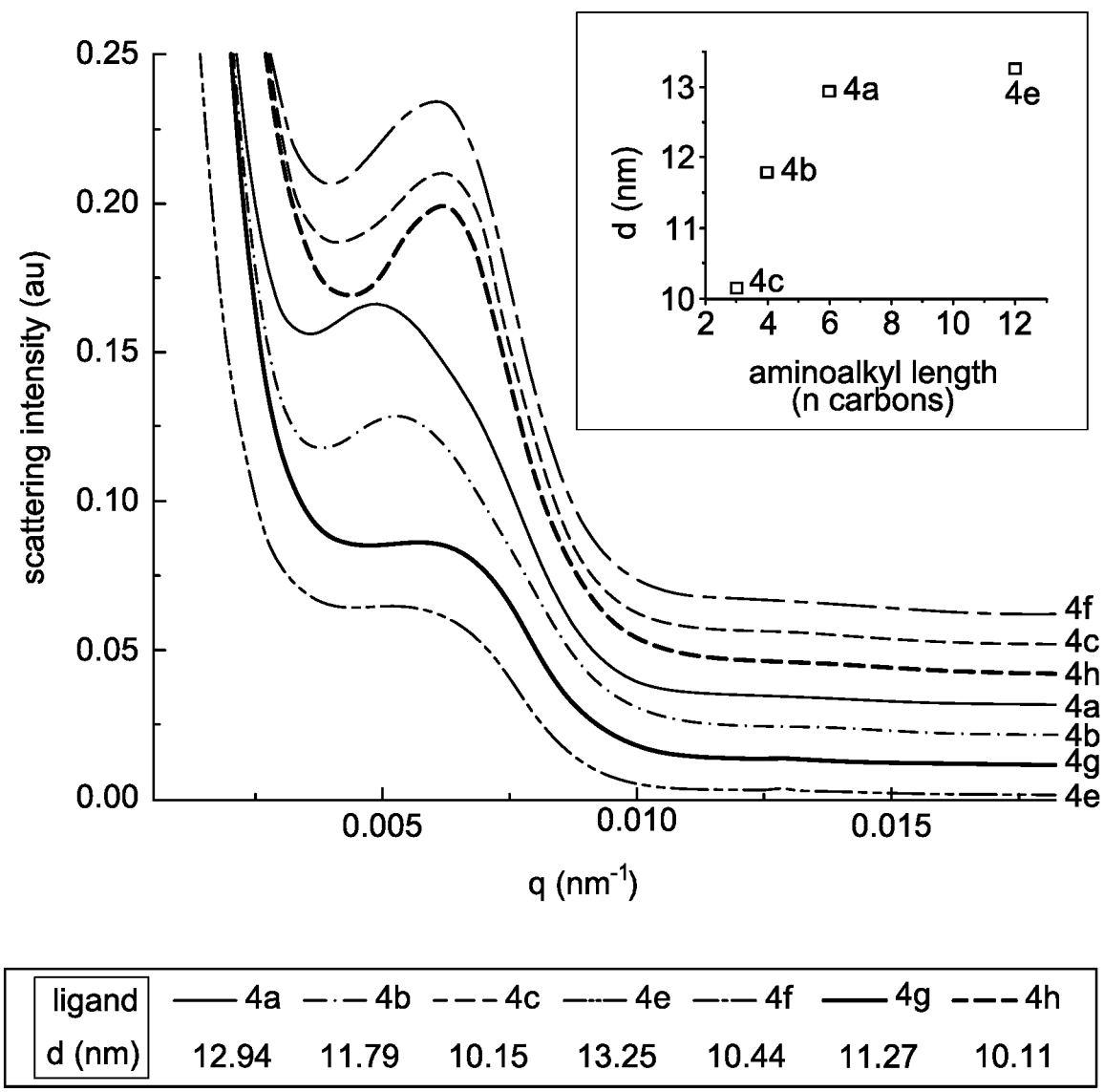
FIG. 7 shows small-angle X-ray scattering (SAXS) data collected at 10 keV with 1 s exposure for exemplary assembled quantum dot nanocapsules suspended in nematic liquid crystal, prepared at 0.15 wt % and plotted as relative intensity as a function of scattering vector, q. The characteristic interparticle spacing, d, was calculated from each peak position as $2\pi/q$.

FIG. 7, shows small-angle x-ray scattering (SAXS) data collected at 10 keV with 1 s exposure for exemplary assembled quantum dot nanocapsules suspended in nematic liquid crystal prepared at 0.15 wt %, and plotted as relative intensity as a function of scattering vector, q. The characteristic interparticle spacing, d, was calculated from each peak position as 2π/q.

FIG. 7 shows scattering intensity as a function of the scattering vector, q, which is related to average quantum dot separation within the shell wall, d, as q=2π/q. For each sample, a broad diffraction peak was observed (the positions of which were determined by subtracting a baseline from the raw data and fitting a Gaussian). As shown in FIG. 7, tether length (e.g., number of carbon atoms in the amine tether of organic ligands 4a-4h) has a significant effect on interparticle separation. The homologous series of ligands 4d, 4c, 4b, and 4a, employing 3-, 4-, 6-, and 12-carbon aminoalkyl tethers, respectively, afforded inter-dot separations of 10.15, 11.79, 12.94, and 13.25 nm—an apparent logarithmin correlation between inter-dot separation and amionalkyl chain length (see, e.g., insert, top right of FIG. 7).

When the ethereal arm meta to the aminoalkyl tether was changed from $CH_3$ (e.g., —$OCH_3$) to $C_4H_3$ (e.g., —$OCH_2CH_2CH_2CH_3$), the amionalkyl chain length appeared to no longer correlate with the interparticle spacing. By way of example, ligand 4h, which of the organic ligands 4a-4h has the most aliphatic carbons, afforded microcapsules with the closest average inter-dot distance (10.11 nm).

Although the foregoing embodiments have been described in some detail by way of illustration and example for purposes of clarity of understanding, it is readily apparent to those of ordinary skill in the art in light of the teachings of the present disclosure that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. An organic ligand of formula (I):

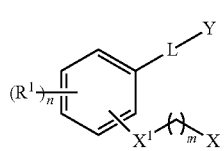

(I)

wherein:
L is selected from biphenyl and substituted biphenyl;
Y is selected from halogen, hydroxyl, azido, phenyl, substituted phenyl, biphenyl, substituted biphenyl, alkoxy, substituted alkoxy, alkyl, substituted alkyl, amino, substituted amino, cycloalkyl, substituted cycloalkyl, heterocycloalkyl, and substituted heterocycloalkyl;
$R^1$ are each independently selected from H, halogen, hydroxyl, azido, alkyl, substituted alkyl, alkenyl, substituted alkenyl, alkynyl, substituted alkynyl, alkoxy, substituted alkoxy, amino, and substituted amino;
X is an amine or a thiol group;
$X^1$ is selected from O, NR', CR'2 and S, wherein each R' is independently selected from H, alkyl, substituted alkyl, alkenyl, substituted alkenyl, aryl, substituted aryl;
n is an integer from 1 to 4; and
m is an integer from 1 to 14.

2. The organic ligand of claim 1, of the formula (II):

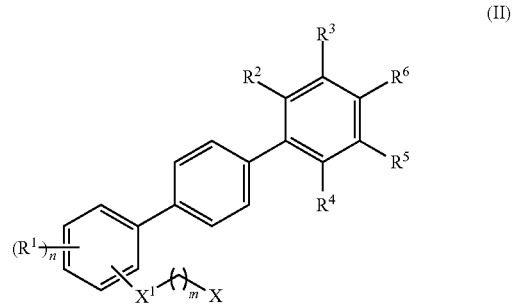

(II)

wherein:
$R^1$ are each independently selected H, halogen, hydroxyl, azido, alkyl, substituted alkyl, alkenyl, substituted alkenyl, alkynyl, substituted alkynyl, alkoxy, substituted alkoxy, amino, and substituted amino;
$R^2$, $R^3$, $R^4$, $R^5$, and $R^6$ are each independently selected from H, halogen, hydroxyl, azido, alkyl, substituted alkyl, alkenyl, substituted alkenyl, alkynyl, substituted alkynyl, alkoxy, substituted alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol, wherein at least one of $R^2$, $R^3$, $R^4$, $R^5$, and $R^6$ is not H;
X is an amine or a thiol group;
$X^1$ is selected from O, NR', CR'2 and S, wherein each R' is independently selected from H, alkyl, substituted alkyl, alkenyl, substituted alkenyl, aryl, substituted aryl;
n is an integer from 1 to 4; and
m is an integer from 1 to 14.

3. The organic ligand of claim 2, of the formula (III):

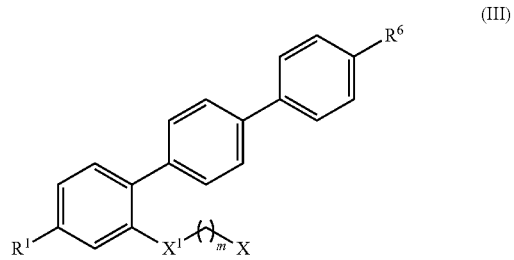

(III)

wherein:
$R^1$ is selected from halogen, hydroxyl, azido, alkyl, substituted alkyl, alkenyl, substituted alkenyl, alkynyl, substituted alkynyl, alkoxy, substituted alkoxy, amino, and substituted amino;
$R^6$ is selected from halogen, hydroxyl, azido, alkyl, substituted alkyl, alkenyl, substituted alkenyl, alkynyl, substituted alkynyl, alkoxy, substituted alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol;

X is an amine or a thiol group;

X$^1$ is selected from O, NR', CR'2 and S, wherein each R' is independently selected from H, alkyl, substituted alkyl, alkenyl, substituted alkenyl, aryl, substituted aryl; and m is an integer from 1 to 14.

4. The organic ligand of claim 3, wherein R$^1$ is alkoxy or substituted alkoxy.

5. The organic ligand of claim 4, wherein R$^1$ is C$_1$-C$_{12}$ alkoxy.

6. The organic ligand of claim 5, wherein R$^1$ is methoxy.

7. The organic ligand of claim 3, wherein R$^6$ is alkoxy or substituted alkoxy.

8. The organic ligand of claim 7, wherein R$^6$ is C$_1$-C$_{12}$ alkoxy.

9. The organic ligand of claim 3, wherein X$^1$ is O.

10. The organic ligand of claim 3, wherein R$^1$ is alkoxy, R$^6$ is alkoxy, and X$^1$ is O.

11. The organic ligand of claim 10, wherein X is an amine group.

12. The organic ligand of claim 10, wherein X is a thiol group.

13. The organic ligand of claim 1, wherein at least one R$^1$ is alkoxy.

14. The organic ligand of claim 11, selected from the group:

15. The organic ligand of claim 12, of the structure (5):
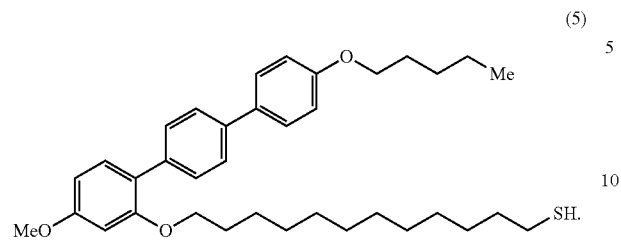
* * * * *